(12) United States Patent
Sodeoka et al.

(10) Patent No.: US 10,338,078 B2
(45) Date of Patent: Jul. 2, 2019

(54) METHOD AND APPARATUS FOR ANALYZING BIOMOLECULES USING RAMAN SPECTROSCOPY

(71) Applicant: Japan Science and Technology Agency, Kawaguchi-Shi (JP)

(72) Inventors: Mikiko Sodeoka, Wako (JP); Jun Ando, Suita (JP); Miwako Asanuma, Wako (JP); Kosuke Dodo, Wako (JP); Katsumasa Fujita, Suita (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 0 days.

(21) Appl. No.: 14/422,055

(22) PCT Filed: Aug. 13, 2013

(86) PCT No.: PCT/JP2013/071844
§ 371 (c)(1),
(2) Date: Feb. 17, 2015

(87) PCT Pub. No.: WO2014/027652
PCT Pub. Date: Feb. 20, 2014

(65) Prior Publication Data
US 2015/0192590 A1 Jul. 9, 2015

(30) Foreign Application Priority Data

Aug. 17, 2012 (JP) .................... 2012-181140

(51) Int. Cl.
*G01N 33/68* (2006.01)
*G01N 21/65* (2006.01)
(Continued)

(52) U.S. Cl.
CPC ....... *G01N 33/6845* (2013.01); *C12N 9/6472* (2013.01); *C12Y 304/22001* (2013.01);
(Continued)

(58) Field of Classification Search
None
See application file for complete search history.

(56) References Cited

U.S. PATENT DOCUMENTS 6,358,692 B1 * 3/2002 Jindal .................. G01N 30/461
435/7.1
7,283,228 B2  10/2007 Zhang et al.
(Continued)

FOREIGN PATENT DOCUMENTS

JP   2004045350 A   2/2004
JP   2004530867 A   10/2004
(Continued)

OTHER PUBLICATIONS

Mills, J.S., et al. Identification of a Ligand Binding Site in the Human Neutrophil Formyl Peptide Receptor Using a Site-specific Fluorescent Photoaffinity Label and Mass Spectrometry, 1998, The Journal of Biological Chemistry, vol. 273(17), pp. 10428-10435.*
(Continued)

*Primary Examiner* — Xiaoyun R Xu
(74) *Attorney, Agent, or Firm* — McCarter & English, LLP

(57) ABSTRACT

The present invention provides an apparatus having a sample separation unit, a Raman spectroscopy unit, and a mass spectrometry unit. The present invention further provides a method for specifying a biomolecule and a method for identifying the binding site of the biomolecule and the low-molecular-weight compound, comprising a combination of Raman spectroscopy and mass spectrometry. The present invention further provides a surface-enhanced Raman spectroscopy method with improved sensitivity.

14 Claims, 44 Drawing Sheets

Specification includes a Sequence Listing.

(51) Int. Cl.

| | | |
|---|---|---|
| *G01N 30/72* | (2006.01) | |
| *G01N 33/58* | (2006.01) | |
| *G01N 27/447* | (2006.01) | |
| *H01J 49/00* | (2006.01) | |
| *C12N 9/64* | (2006.01) | |
| *G01N 30/74* | (2006.01) | |
| *G01N 30/78* | (2006.01) | |
| *H01J 49/04* | (2006.01) | |

(52) U.S. Cl.
CPC ........... *G01N 21/65* (2013.01); *G01N 21/658* (2013.01); *G01N 27/44726* (2013.01); *G01N 30/7233* (2013.01); *G01N 33/587* (2013.01); *H01J 49/004* (2013.01); *G01N 30/74* (2013.01); *G01N 30/78* (2013.01); *G01N 2570/00* (2013.01); *H01J 49/0418* (2013.01)

(56) References Cited

U.S. PATENT DOCUMENTS

| | | |
|---|---|---|
| 2004/0017884 A1 | 1/2004 | Havrilla et al. |
| 2004/0086897 A1 | 5/2004 | Mirkin et al. |
| 2006/0134714 A1 | 6/2006 | Sundararajan et al. |
| 2007/0099256 A1 | 5/2007 | Sundararajan et al. |
| 2007/0134733 A1* | 6/2007 | Haddach ............... G01N 21/65 435/7.2 |
| 2007/0158549 A1 | 7/2007 | Naya et al. |
| 2008/0003576 A1 | 1/2008 | Zhang et al. |
| 2009/0069500 A1 | 3/2009 | Stavrianopoulos et al. |
| 2010/0078552 A1 | 4/2010 | Ikeda et al. |

FOREIGN PATENT DOCUMENTS

| | | |
|---|---|---|
| JP | 2005524849 A | 8/2005 |
| JP | 2006-503268 A | 1/2006 |
| JP | 2007171003 A | 7/2007 |
| JP | 2009-192543 A | 8/2009 |
| JP | 2010-078482 A | 4/2010 |
| WO | WO-2002071013 A1 | 9/2002 |

OTHER PUBLICATIONS

International Search Report for International Application No. PCT/JP2013/071844.
Yamakoshi et al., "Imaging of EdU, an Alkyne-Tagged Cell Proliferation Probe by Raman Microscopy", JACS, 2011, vol. 133, pp. 6102-6105.
Thuaud et al., "Synthetic Analogue of Rocaglaol Displays a Potent and Selective Cytotoxicity in Cancer Cells: Involvement of Apoptosis Inducing Factor and Caspase-12", J. Med. Chem., 2009, vol. 52, pp. 5176-5187.
Hoffstrom et al., "Inhibitors of Protein Disulfide Isomerase Suppress Apoptosis Induced by Misfolded Proteins", Nature Chemical Biology, 2010, vol. 6, pp. 900-906.
Martin et al., "Global Profiling of Dynamic Protein Palmitoylation", Nature Methods, 2012, vol. 9, No. 1, pp. 84-89.
Kho et al., "A Tagging-via-Substrate Technology for Detection and Proteomics of Farnesylated Proteins", Proc Natl Acad Sci U.S.A., 2004, vol. 101, No. 34, pp. 12478-12484.
Fujita, Katsumasa, et al., "Rama Imaging of Alkyne as a Small Tag for Biological Molecules", Medical Imaging 2002: PACS and Integrated Medical Information Systems: Design and Evaluation, Feb. 8, 2012, vol. 8225, pp. 1-4.
Supplementary European Search Report relating to co-pending European Application No. EP13879362, dated Mar. 23, 2016—3 Pages.

* cited by examiner

Fig. 8-1
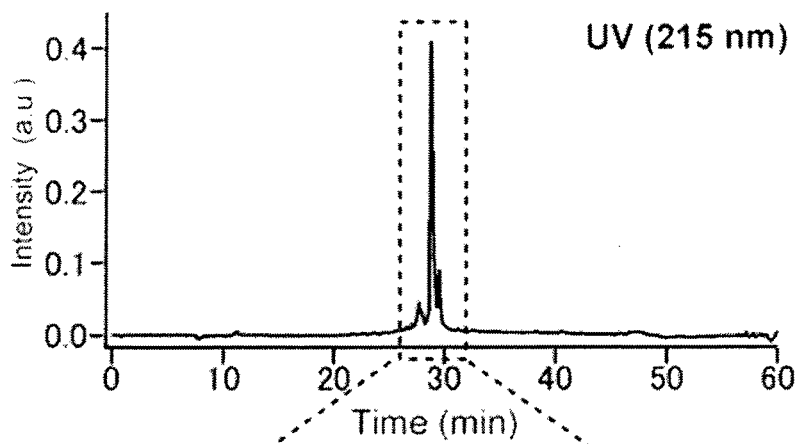
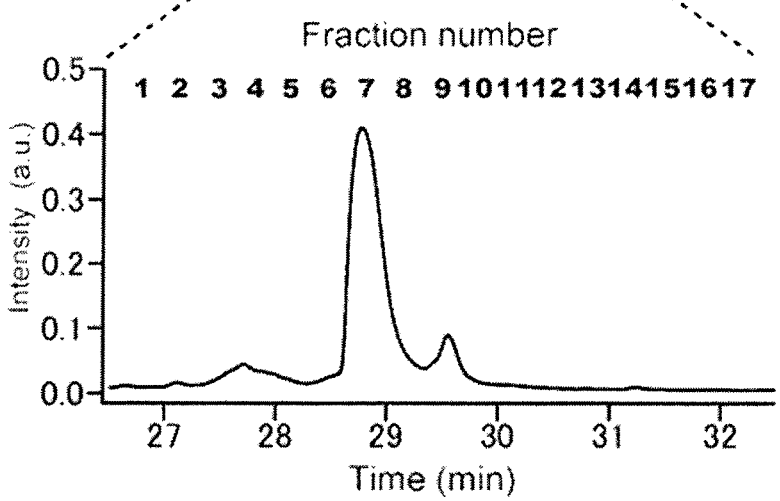
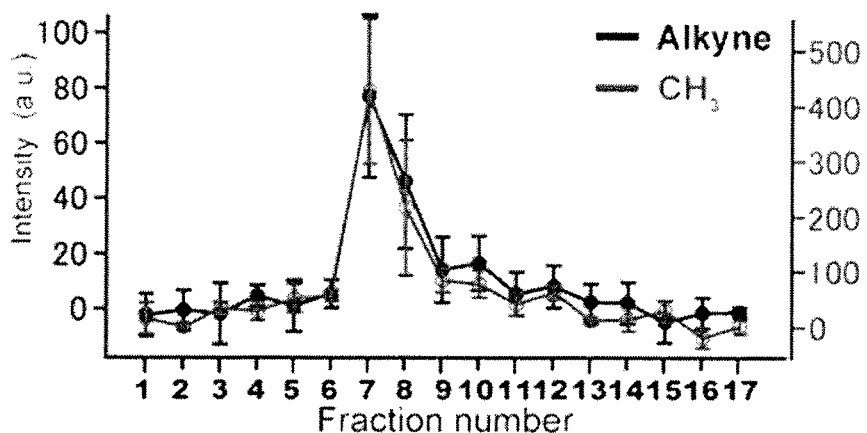

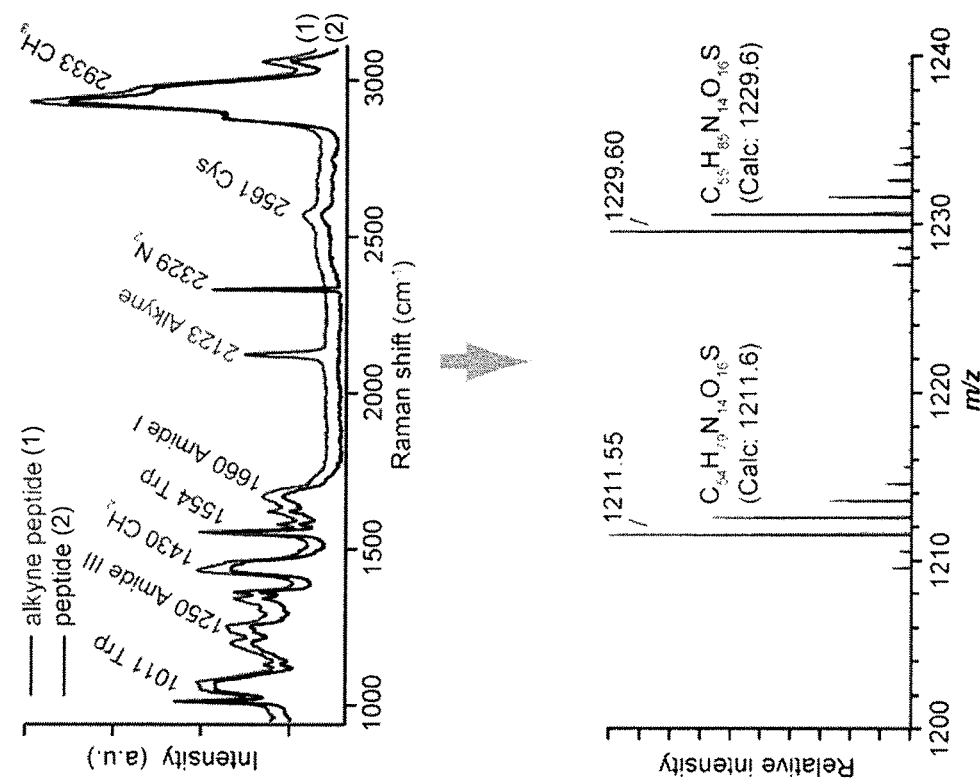
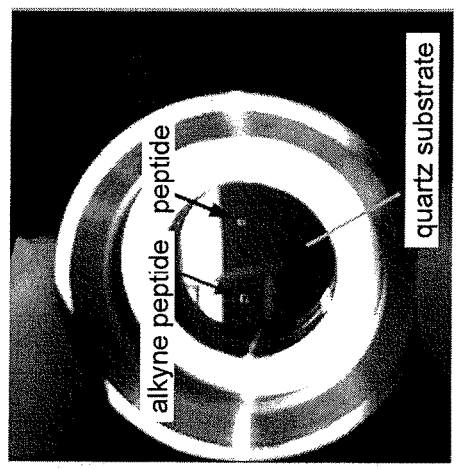
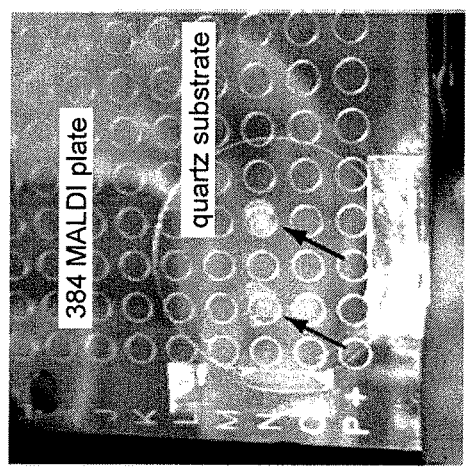
Fig. 16

Fig. 22-2
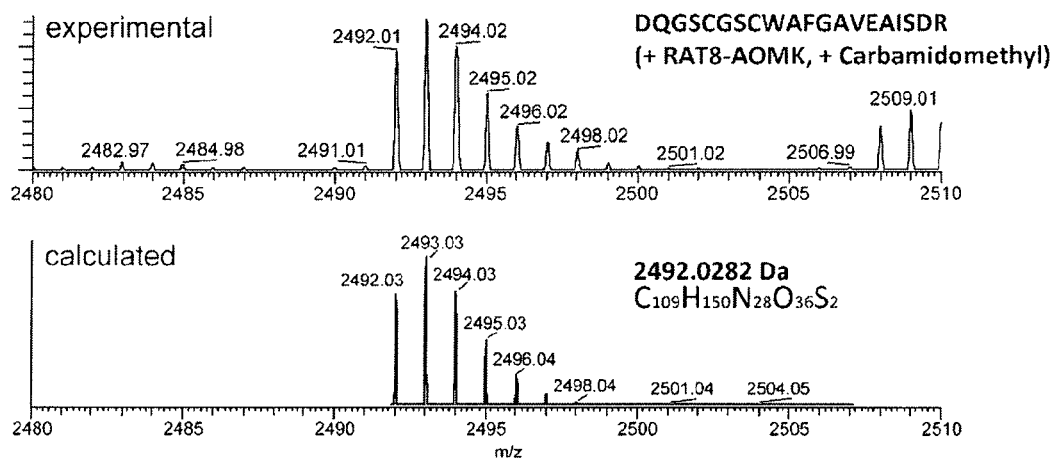
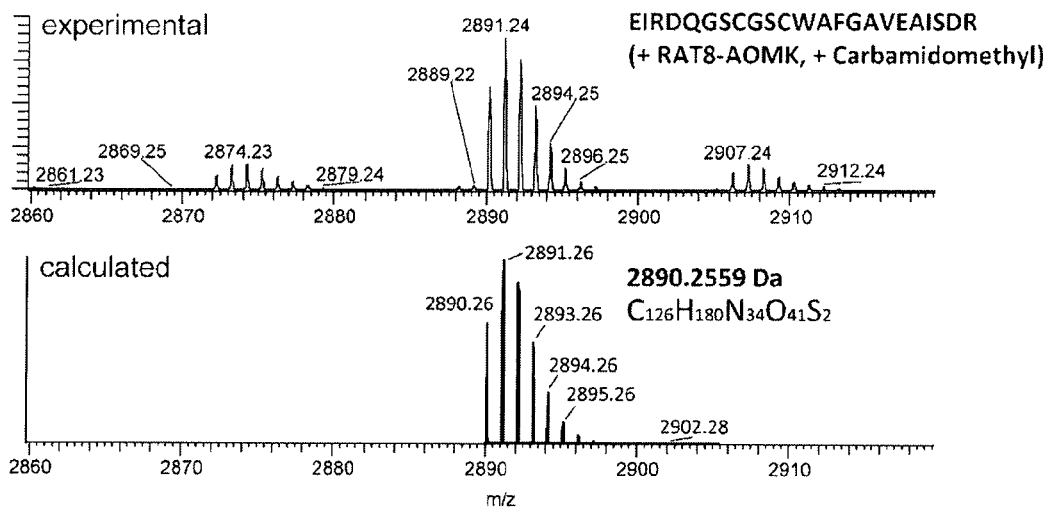
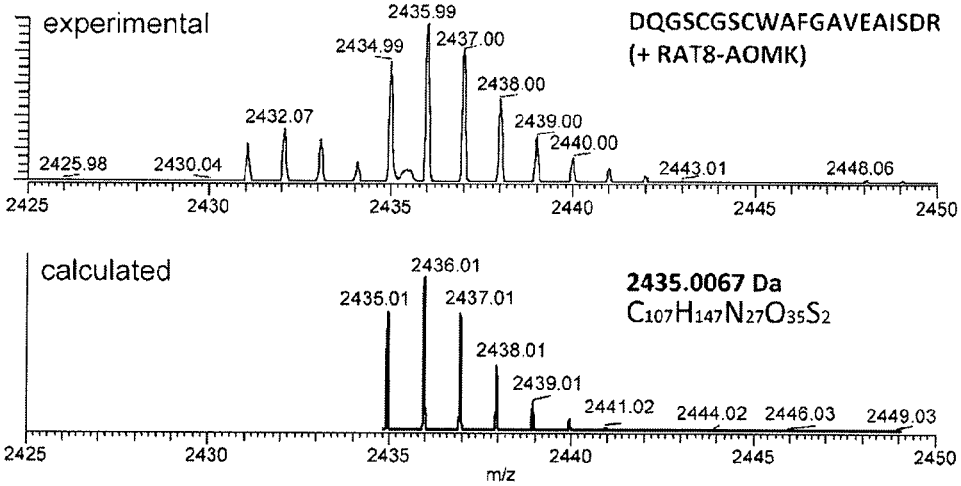

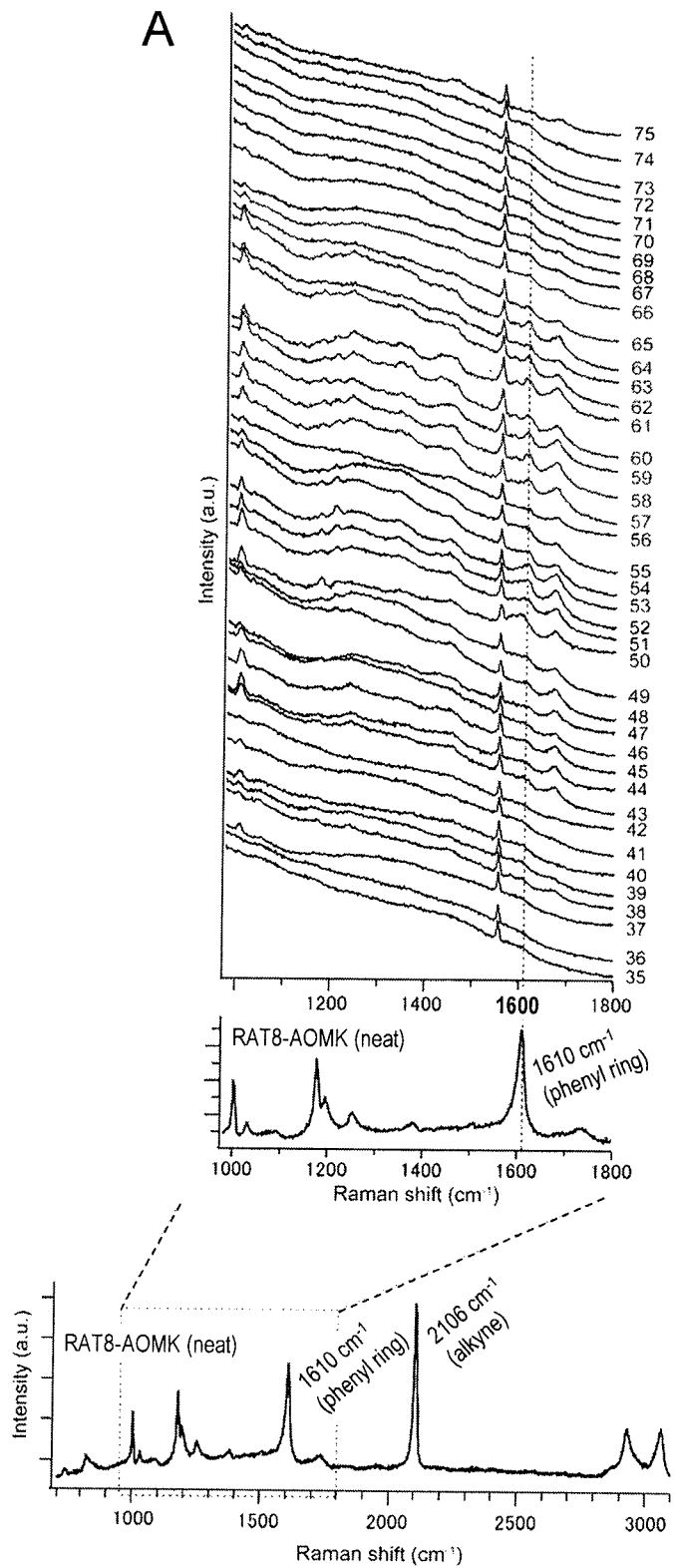

METHOD AND APPARATUS FOR ANALYZING BIOMOLECULES USING RAMAN SPECTROSCOPY

RELATED APPLICATIONS

This application is a national stage application filed under 35 USC 371 of PCT/JP2013/071844, filed Aug. 13, 2013, which claims the benefit of Japanese Patent Application No. 2012-181140, filed Aug. 17, 2012, all of which are incorporated herein, in entirety, by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 119244_00081_Sequence_Listing. The size of the text file is 5 KB, and the text file was created on Feb. 17, 2015.

TECHNICAL FIELD

The present invention relates to an analytical method and apparatus for specifying a biomolecule and in particular an intracellular or extracellular biomolecule that binds to a low-molecular-weight compound, or identifying the binding site of a biomolecule and a low-molecular-weight compound. More specifically, the present invention relates to an apparatus comprising a sample separation unit, a Raman spectroscopy unit, a mass spectrometry unit and a method for specifying a biomolecule through a combination of Raman spectroscopy and mass spectrometry, and a method for identifying the binding site of a biomolecule and a low-molecular-weight compound. The present invention further relates to a surface-enhanced Raman spectroscopy method.

BACKGROUND ART

Low-molecular-weight compounds (e.g., drugs) having toxicity or drug efficacy act in vivo on biomolecules such as proteins to exhibit bioactivity. Examining in vivo or intracellular distribution of target biomolecules on which low-molecular-weight compounds act, specifying the target biomolecules, analyzing specific sites at which low-molecular-weight compounds act, as well as elucidating the mechanism for the expression of bioactivity is extremely important for the development of effective therapeutic methods and remedies and life research that underlies such developments.

Regarding methods for examining the in vivo or intracellular distribution of target biomolecules, molecular imaging using radioactive compounds, phosphorescent compounds or fluorescent compounds, and Raman imaging for detecting scattered light of the biomolecule themselves are known. In vivo or intracellular molecular imaging is an important technique for understanding conditions of the disease status and pharmacokinetics and the like, and has recently been undergoing rapid development. Raman imaging involves detecting Raman scattering light from a sample irradiated by a laser and then imaging the distribution, by using the Raman spectroscopy method. Molecular imaging involves the use of radioactive compounds, phosphorescent compounds, or fluorescent compounds. On the other hand, Raman imaging involves the use of low-molecular-weight compounds that are nonradioactive and have only a slight effect on target molecules, and thus enables convenient direct examination of dynamic cell states. It has been reported that when alkyne or the like having a carbon-carbon triple bond is used as a label, imaging with higher sensitivity can be achieved with a minimal effect on target molecules (Non-patent Document 1). Non-patent Document 1 describes incorporating a nucleic acid analog, 5-ethyl-2'-deoxyuridine (EdU) into cells, and confirming the incorporation thereof to cell nuclei by using Raman microscope imaging (see Non-patent Document 1, page 6103, FIG. 2, and FIG. 4). In Non-patent Document 1, Raman images are obtained with wavenumbers, with which a Raman peak unique to label is obtained. Therefore, the thus obtained image corresponds to the spatial intensity distribution of the Raman peak with specific wavenumber.

Regarding the method of searching a low-molecular-weight compound such as a drug and a biomolecule which is the target of the compound and then identifying the binding site, LC-MS combining a liquid chromatograph with a mass spectrometer is used. A sample is fractionated by LC, and then the fractionated sample is subjected sequentially to MS and MS/MS analysis in an exhaustive manner, so as to specify the target biomolecule or identify the binding site. In MS analysis, the target biomolecule is searched for based on a mass shift resulting from the binding of the low-molecular-weight compound. Further, information such as the amino acid sequence of the peptide can be acquired by MS/MS analysis, and thus the binding site can be identified.

In order to identify a target biomolecule within cells by an analytical method such as LC-MS, the following series of steps are required: (1) incorporate a low-molecular-weight compound into cells and bind the low-molecular-weight compound to an intracellular target biomolecule; (2) disrupt the cells, (3) detect the target biomolecule in the cell disruption solution, and (4) analyze and specify the target biomolecule; or, (1) disrupt the cells, (2) mix the cell disruption solution with a low-molecular-weight compound to bind to a target biomolecule, (3) fractionate the cell disruption solution, and (4) analyze and specify the target biomolecule. Moreover, a method for specifying and/or identifying the binding site of a biomolecule and a low-molecular-weight compound requires the following steps: (1) bind a low-molecular-weight compound to a biomolecule, (2) fragment the biomolecule bound to the low-molecular-weight compound, (3) detect the bound fragment, and (4) analyze the bound fragment to identify the binding site.

However, regarding complex samples obtained via the above steps, an exhaustive search for a biomolecule using LC-MS, sequencing, and specifying the binding site requires tremendous time and also errors are likely to arise. In addition, when the binding mode of a low-molecular-weight compound and a biomolecule is unknown, it is, in principal, impossible to search for the target molecule based on a predicted mass shift. A method (CE-MS) using a capillary electrophoretic device instead of a liquid chromatograph has also been devised. However, as with LC-MS, this method requires exhaustive detection and, therefore, an extremely large number of objects must be analyzed, and prolonged and complicated analysis procedures are required.

As a technique for selectively subjecting an intracellular target molecule to analysis such as mass spectrometry, a method comprising affinity purification using a low-molecular-weight compound bound to a carrier in order to separate and purify the target molecule has been developed and is used widely. Moreover, a method for specifying a bound target biomolecule by: generating a covalent bond using a functional group reactive to the target biomolecule; and examining a radioactive, phosphorescent, or fluorescent compound or the like introduced in advance into the low-molecular-weight compound is used. Regarding a technique for specifying and/or identifying a binding site of a target molecule, a method comprising introducing a fluorophore into the low-molecular-weight compound and observing the same is used widely. For example, regarding a method for specifying and/or identifying the binding site of a labeled drug and a protein, a method using a xanthine dye as a fluorophore (rhodamine, fluorescein, or rodol), a cyanine dye, a coumarin dye, or a composite dye as a label for the drug has been reported (Patent Document 1).

When a radioactive compound is used as the low-molecular-weight compound there is no effect on the activity of the target molecule since radio isotopes basically have identical chemical properties. However, facilities in which the method can be used are limited to those in which radiation can be controlled. Further such method strictly restricts the step of identifying the binding site and is not convenient. Unlike methods using radioactive compounds, there are very few restrictions on carrying out methods that involve direct binding of a phosphorescent compound or a fluorescent compound having a large molecular weight to the target molecule. However, since the molecular weight of a fluorophore becomes relatively higher than that of the low-molecular-weight compound, such method is problematic in that the activity or binding properties of the low-molecular-weight compound can be affected. For example, whereas fluorouracil (5-FU), a type of anticancer agent, has a molecular weight of 130, Rhodamine 6G, a typical fluorophore, has a molecular weight of 479. When 5-FU is labeled with Rhodamine 6G, the bioactivity of the anticancer agent, 5-FU, can be affected by the fluorescent label. Further, flavagline, an anticancer agent extracted from an Aglaia plant, inhibits cell growth in a cancer-cell-specific manner and is not likely to cause side effects. Therefore, attempts have been made to elucidate the in vivo mode of action thereof. However, it is reported that when flavagline is labeled with a fluorophore, the drug activity decreases to ¹⁄₄₀ or less of its previous level. Non-patent Document 2 (page 5180, right column) describes that while the $IC_{50}$ (concentration at which flavagline suppress cell growth by 50%) of flavagline is 3 nM, the $IC_{50}$ of flavagline labeled with fluorescence decreases to 130 nM. Non-patent Document 3 reports that the molecule 16F16, which binds to a target protein, loses its activity when modified with a fluorophore (Non-patent Document 3, page 901, right column, lines 13-17).

A modified version of the above labeling methods has been reported, which involves binding a low-molecular-weight compound (alkyne) containing an alkynyl group as a functional group to a target biomolecule, introducing a fluorophore via a click reaction, and degrading and fragmenting the target biomolecule using an enzyme and the like (see Non-patent Document 3, page 902, FIG. 3). The use of this method leads to decreased detrimental effects such as dissipation of the activity of a target protein. However, this method is problematic in that procedures are complex, nonspecific binding reactions occur, a catalyst such as copper is needed, and there is loss of the target molecule due to reaction procedures. Therefore, when the amount of a sample is insufficient, there are limits to apply this method in practice. Regarding methods for searching for intracellular post-translational modification of a protein, examples using a click reaction include a report of incorporating a palmitoyl lipid into cells, modifying the same with a fluorophore via a click reaction, and then specifying a protein that binds to the lipid using fluorescence analysis (Non-patent Document 4) and a report of introducing a biotin tag into a farnesyl lipid via a click reaction and then detecting the same with streptavidin (Non-patent Document 5). However, these methods also have the problems above associated with click reactions.

Unlike techniques that involve searching a target molecule via a label such as a radioactive substance or a fluorophore, the Raman spectroscopy method can detect a target molecule without using any label by a based on molecular vibration information. There are no limitations on Facilities to carry out Raman spectroscopy and the method does not affect the activity or the binding properties of the low-molecular-weight compound. Thus, the combination of Raman spectroscopy and LC-MS may constitute a new detection technique that overcomes the various problems described above. To date, an example of analyzing lysozyme using a combination of a Raman spectroscopic apparatus and a matrix assisted laser desorption/ionization mass spectrometer has been reported (Patent Document 2, column 27, FIG. 31 and claim 21). However, the object to be achieved by the invention described in Patent Document 2 is to increase the sensitivity of Raman spectroscopy, and Patent Document 2 discloses a technique for aggregating a sample in an isolated state. The reason a mass spectrometer is used in Patent Document 2 is to re-confirm the results confirmed by Raman spectroscopy using a different method. Therefore, the method of Patent Document 2 is substantially different from that of the present invention for specifying a biomolecule that binds to a low-molecular-weight compound and identifying the binding site.

CITATION LIST

Patent Documents

Patent Document 1: JP Patent Publication (Kokai) No. 2009-192543A. Patent Document 2: U.S. Pat. No. 7,283, 228
Non-patent Documents. Non-patent Document 1: H. Yamakoshi et al., JACS, 133, 6102 (2011). Non-patent Document 2: F. Thuaud et al., J. Med. Chem. 52, 5176 (2009). Non-patent Document 3: B. G. Hoffstrom et al., Nature Chemical Biology, 6, 900 (2010). Non-patent Document 4: Brent R Martin et al., Nature Methods 9, 84-89, (2012). Non-patent Document 5: Yoonjung Kho et al., Proc Natl Acad Sci U.S.A. 2004; 101(34): pp. 12479-12484

SUMMARY OF INVENTION

Technical Problem

Although specifying a target molecule that binds to a biomolecule among a variety of biomolecules contained in in vivo cells, and identifying the binding site are extremely important techniques for development of effective remedies for various diseases, and the like, practical and convenient methods therefor and analyzers for the same are not known.

The conventional techniques of LC-MS and CE-MS are established techniques; however, they consume tremendous time and are prone to errors since these techniques involve exhaustive search for biomolecules, sequencing, and specifying binding sites.

Regarding in silico mass spectrum data analysis of biomolecules and target molecules, for example, in situations where it has been revealed that a certain drug acts on a certain protein, but the type of amino acid residue in said protein to which said drug binds (or upon which it acts) is not specified, it is very difficult to specify and identify the protein binding site using existing search engines (e.g., Mascot. Matrix Science Inc. www.matrixscience.com or Electrophoresis, 20, (18), 3551-67 (1999)).

Moreover, when a molecule containing a radio isotope or a molecule bound to a phosphorescent compound or a fluorescent compound is used as a labeled drug, this can be problematic in that the activity (binding capacity) of the target molecule can decrease or dissipate due to the introduction of a fluorophore having a large molecular weight. In addition, such molecule bound to a phosphorescent compound or a fluorescent compound can firmly bind nonspecifically to a column in the course of chromatography processes and may be difficult to isolate and collect, for example.

Therefore, an object of the present invention is to provide a method and an apparatus to specifying a target molecule that binds to a biomolecule in a practical and convenient manner, thus allowing identification of the binding site.

Another object of the present invention is to provide a surface-enhanced Raman spectroscopy (SERS) method with enhanced sensitivity.

Means for Solving the Problem

As a result of intensive studies to address the above problems with conventional techniques, the present inventors have found that a biomolecule binding to a low-molecular-weight compound can be specified by subjecting a fractionated sample to Raman spectroscopy and then to mass spectrometry, and the binding site of the low-molecular-weight compound and the biomolecule can be specified. Thus, they have completed the present invention. The present inventors have further discovered that SERS sensitivity can be enhanced with the use of an aggregation-accelerating agent, and thus, they have completed the present invention. Specifically, the present invention is as follows.

[1] An apparatus for specifying a biomolecule that binds to a low-molecular-weight compound, or, an apparatus for identifying the binding site of a low-molecular-weight compound and a biomolecule, wherein the apparatus comprises a sample separation unit, a Raman spectroscopy unit, and a mass spectrometry unit, and wherein the sample separation unit, the Raman spectroscopy unit, and the mass spectrometry unit are connected in this order.

[2] The apparatus according to [1], wherein the sample separation unit is a liquid chromatographic device or a capillary electrophoretic device.

[3] The apparatus according to [2], wherein the liquid chromatography is any one type of high performance liquid chromatography selected from the group consisting of normal phase, reverse phase, molecular sieve, and ion exchange chromatography.

[4] The apparatus according to any one of [1] to [3], wherein the Raman spectroscopy unit is a linear or non-linear Raman spectroscopic device having a laser unit for irradiating a Raman excitation laser beam and a spectral analysis unit for spectral analysis of Raman scattering light.

[5] The apparatus according to any one of [1] to [4], wherein the mass spectrometry unit comprises a mass spectrometer that uses matrix-assisted laser desorption ionization, electrospray ionization, or atmospheric pressure chemical ionization as an ionization method.

[6] The apparatus according to any one of [1] to [5], wherein the low-molecular-weight compound exhibits a Raman peak distinguishable from those of biomolecules.

[7] The apparatus according to any one of [1] to [6], wherein the low-molecular-weight compound contains within the molecule at least 1 type of substituent selected from the group consisting of an alkynyl group, a nitrile group, a diazonio group, an isocyanate ester group, an isonitrile group, a ketene group, a carbodiimide group, a thiocyanate ester group, an azide group, a diazo group, an alkynediyl group, and deuterium having a scattering spectrum in a silent region of the Raman spectrum.

[8] The apparatus according to any one of [1] to [7], wherein the biomolecule is at least 1 type of biomolecule selected from the group consisting of a protein, a peptide, a nucleic acid, a sugar and a lipid.

[9] A plate having a cleaned surface to be used for the apparatus of [1].

[10] The plate according to [9], wherein the cleaned surface contains a water-repellent surface.

[11] The plate according to [9] or [10], which is made of metal, glass, quartz, calcium fluoride, or magnesium fluoride.

[12] A method for identifying the binding site of a biomolecule and a low-molecular-weight compound, comprising the following steps of (1) subjecting a fractionated fragment of a biomolecule bound to a low-molecular-weight compound to Raman spectroscopy, and (2) subjecting all or some fractions which were subjected to Raman spectroscopy to mass spectrometry, whereby the binding site of the low-molecular-weight compound within the biomolecule is identified by detecting a fraction having a Raman peak derived from the low-molecular-weight compound bound to a fragment of the biomolecule via Raman spectroscopy, obtaining the mass spectrometric results for a fraction having a Raman peak derived from the low-molecular-weight compound, and comparing the results with the mass information of the biomolecule.

[13] The method according to [12], comprising fragmenting a biomolecule bound to a low-molecular-weight compound, and fractionating the fragment, thereby preparing the fractionated fragment of the biomolecule bound to the low-molecular-weight compound.

[14] The method according to [12] or [13], wherein the biomolecule bound to the low-molecular-weight compound is obtained by mixing the low-molecular-weight compound with the biomolecule under acellular conditions.

[15] The method according to [13], wherein the biomolecule is fragmented by an enzyme selected from the group consisting of protease, peptidase, nuclease, glycolytic enzyme, and lipase, or chemical degradation.

[16] A screening method for specifying a biomolecule that binds to a low-molecular-weight compound, comprising the following steps of (1) subjecting a fraction containing a biomolecule bound to a low-molecular-weight compound to Raman spectroscopy, and (2) subjecting all or some of the fractions subjected to Raman spectroscopy to mass spectrometry, whereby a biomolecule that binds to the low-molecular-weight compound is specified by detecting a fraction having a Raman peak derived from the low-molecular-weight compound by Raman spectroscopy, obtaining the mass spectrometric results for the fraction having a Raman peak derived from the low-molecular-weight compound, and comparing the results with the mass information of the biomolecule.

[17] The method according to [16], comprising fractionating a sample containing a biomolecule bound to a low-molecular-weight compound, and then preparing a fraction containing the biomolecule bound to the low-molecular-weight compound.

[18] The method according to [17], wherein the sample containing the biomolecule bound to the low-molecular-weight compound is prepared by: (A) causing cells to incorporate the low-molecular-weight compound, so that the compound binds to the intracellular biomolecule, and disrupting the cells; or (B) disrupting cells and adding the low-molecular-weight compound to the cell disruption solution, so that the compound binds to the intracellular biomolecule.

[19] The method according to any one of [12] to [18], wherein the low-molecular-weight compound exhibits a Raman peak distinguishable from that of the biomolecule.

[20] The method according to any one of [12] to [19], wherein the low-molecular-weight compound contains within the molecule, at least 1 type of substituent selected from the group consisting of an alkynyl group, a nitrile group, a diazonio group, an isocyanate ester group, an isonitrile group, a ketene group, a carbodiimide group, a thiocyanate ester group, an azide group, a diazo group, an alkynediyl group, and deuterium having a scattering spectrum in a silent region of the Raman spectrum.

[21] The method according to any one of [12] to [20], wherein the biomolecule is at least 1 type of biomolecule selected from the group consisting of a protein, a peptide, a nucleic acid, a sugar, and a lipid.

[22] The method according to [13] or [17], wherein fractionation is performed by liquid chromatography or capillary electrophoresis.

[23] The method according to any one of [12] to [22], comprising directly using the fractionated fraction as droplets or mixing the fractionated fraction with a solvent to prepare droplets, arranging the droplets on a plate having a cleaned surface, vaporizing the solvent contained in the droplets, and thus preparing spots to be subjected to Raman spectroscopy.

[24] The method according to [23], wherein the cleaned surface of the plate comprises a water-repellent surface.

[25] The method according to [23] or [24], wherein the plate is made of metal, glass, quartz, calcium fluoride, or magnesium fluoride.

[26] The method according to any one of [23] to [25], wherein a metal nanoparticle or a metal nanostructure selected from the group consisting of gold, silver, platinum, palladium, aluminum, titanium and copper is used for the plate.

[27] The method according to [23], wherein the fractionated fraction is mixed with a solution containing a metal nanoparticle or a metal nanostructure, and subjected directly to Raman spectroscopy.

[28] The method of [26] or [27], comprising adding an organic acid which accelerates the formation of homogeneous aggregates of the metal nanoparticle or metal nanostructure, and
the biomolecule and the biomolecule bound to the low-molecular-weight compound,
to the fractionated fraction.

[29] The method of [28], wherein the organic acid is selected from the group consisting of trifluoroacetic acid, difluoroacetic acid, monofluoroacetic acid, trifluoromethanesulfonic acid, difluoromethanesulfonic acid, 3,3,3-trifluoropropionic acid, trichloroacetic acid, dichloroacetic acid, monochloroacetic acid, trichloromethanesulfonic acid, dichloromethanesulfonic acid, 3,3,3-trichloropropionic acid, formic acid, acetic acid, propionic acid, methanesulfonic acid, and a combination thereof.

[30] The method according to any one of [26] to [29], wherein the low-molecular-weight compound that binds to a biomolecule contains within the molecule at least one type of substituent selected from the group consisting of an alkynyl group, a nitrile group, a diazonio group, an isocyanate ester group, an isonitrile group, a ketene group, a carbodiimide group, a thiocyanate ester group, an azide group, a diazo group, an alkynediyl group, and deuterium having a scattering spectrum in a silent region of the Raman spectrum.

[31] A surface-enhanced Raman spectroscopy method, comprising the steps of
(1) adding a metal nanoparticle or a metal nanostructure to a solution containing a target molecule and an organic acid, and aggregating the thus formed complex of the target molecule and the metal nanoparticle or the metal nanostructure, and
(2) performing surface-enhanced Raman spectroscopic (SERS) analysis on the aggregate.

[32] A surface-enhanced Raman spectroscopy method, comprising the steps of
(1) adding a metal nanoparticle or a metal nanostructure to a solution containing an organic acid for aggregation of the metal nanoparticle or the metal nanostructure,
(2) adding a solution containing a target molecule to the aggregate,
(3) performing surface-enhanced Raman spectroscopic (SERS) analysis of the complex of the metal nanoparticle or the metal nanostructure and the target molecule, which is obtained by step (2).

[33] The method according to [31] or [32], wherein the target molecule is a biomolecule, a fragment of a biomolecule, a biomolecule bound to a low-molecular-weight compound having a Raman peak in a silent region, or a fragment of a biomolecule bound to a low-molecular-weight compound having a Raman peak in a silent region.

[34] The method according to [33], wherein the biomolecule is at least 1 type of biomolecule selected from the group consisting of a protein, a peptide, a nucleic acid, a sugar, and a lipid.

[35] The method according to any one of [31] to [34], wherein the organic acid is selected from the group consisting of trifluoroacetic acid, difluoroacetic acid, monofluoroacetic acid, trifluoromethanesulfonic acid, difluoromethanesulfonic acid, 3,3,3-trifluoropropionic acid, trichloroacetic acid, dichloroacetic acid, monochloroacetic acid, trichloromethanesulfonic acid, dichloromethane sulfonic acid, 3,3,3-trichloropropionic acid, formic acid, acetic acid, propionic acid, methanesulfonic acid, and a combination of any thereof.

[36] The method according to any one of [33] to [35], wherein a low-molecular-weight compound that binds to a biomolecule contains within the molecule at least type of substituent selected from the group consisting of an alkynyl group, a nitrile group, diazonio group, an isocyanate ester group, an isonitrile group, a ketene group, a carbodiimide group, a thiocyanate ester group, an azide group, a diazo group, an alkynediyl group and deuterium having a scattering spectrum in a silent region of the Raman spectrum.

[37] The method according to any one of [31] to [36], wherein the solution containing a target molecule is a fraction fractionated by liquid chromatography or capillary electrophoresis.

[38] The method according to any one of [31] to [37], comprising, before carrying out surface-enhanced Raman spectroscopic (SERS) analysis, arranging droplets of the solution containing the aggregate on a plate having a cleaned surface, vaporizing the solvent contained in the droplets, and thus preparing spots to be subjected to surface-enhanced Raman spectroscopy.

[39] An analytical method, comprising further subjecting the whole or a portion of a solution or all or some fractions subjected to the surface-enhanced Raman spectroscopic (SERS) analysis method according to any one of [31] to [38], to mass spectrometry.

This description includes part or all of the contents as disclosed in the description and/or drawings of Japanese Patent Application No. 2012-181140 which is a priority document of the present application.

Effect of the Invention

The liquid chromatography-Raman spectroscopy-mass spectrometry (LC-R-MS) or capillary electrophoresis-Raman spectroscopy-mass spectrometry (CE-R-MS) apparatus according to the present invention is a novel apparatus for analyzing biomolecules not known in convention, which can shorten processing time and is a highly accurate excellent analyzer, compared with conventional liquid chromatography-mass spectrometry (LC-MS), and capillary electrophoresis-mass spectrometry (CE-MS) apparatuses, and the like, which involve searching exhaustively for biomolecules, performing sequencing, and specifying the binding site. The use of the method according to the present invention enables one to obtain complementary information concerning the subject being measured by Raman spectroscopy and mass spectrometry, and can specify target biomolecules more rapidly and precisely. Furthermore, the SERS method of the present invention, which involves the use of an aggregation-accelerating agent, is characterized by higher measurement sensitivity and improved detection limit. The SERS method of the present invention, which involves the use of an aggregation-accelerating agent, is further characterized by improved correlation between the amount of a sample to be measured and SERS signal intensity, and reduced variation of measurement results.

The Raman spectroscopy unit according to the present invention enables nondestructive and noncontact measurement using a Raman spectroscopic device without modifying the sample. The present invention enables selective and highly sensitive detection of a low-molecular-weight compound using a Raman label having a characteristic Raman peak. For example, compounds having triple bonds, such as alkyne molecules, or deuterium (heavy hydrogen) are almost nonexistent in living bodies. Therefore, when alkyne or deuterium is used as the Raman label, a target biomolecule bound to such low-molecular-weight compound can be specified from a complex mixture such as a cell disruption solution. This similarly applies to other types of Raman labels having Raman peaks in the silent region.

When the Raman spectroscopy according to the present invention is performed, not only a low-molecular-weight compound, but also molecular vibration information from the biomolecule can be obtained and this has the advantage such that co-existence of the low-molecular-weight compound and the biomolecule can be confirmed. In the case of conventional fluorescent labeling methods, the presence or the absence of a low-molecular-weight compound is confirmed based on a single-channel fluorescence intensity. On the other hand, in the case of the Raman spectroscopy method according to the present invention, multidimensional vibrational spectroscopic information is obtained, and, therefore, the presence or the absence of the co-existence of a low-molecular-weight compound and a biomolecule can be confirmed on the basis of a plurality of scattering peak intensities, and, furthermore, information concerning skeletal structures or side chains can also be obtained on the basis of spectral shapes in the case of peptides or the like.

The method according to the present invention enables the direct use of a low-molecular-weight compound, or it enables keeping the molecular weight of the tag to be added to the compound low. Therefore, unlike conventional fluorescent labeling methods which use high-molecular-weight fluorophores, a target biomolecule can be specifically identified and/or detected and specified by the method according to the present invention without altering the biochemical properties of the relevant low-molecular-weight compound. That is, when the Raman label of the present invention is used, the artifact resulting from modification is lower than that when using a fluorophore. Furthermore, mass spectra of a protein or peptide are obtained in the mass spectrometry unit, and then the binding site of a low-molecular-weight compound and a target biomolecule can be identified based on the results. Moreover, the amino acid sequence of a protein or a peptide can also be determined by mass spectrometry using an MS/MS analytical method. Further, post-translational modification of a protein can also be analyzed.

A method that involves the use of a combination of a conventional alkyne tag and a click reaction (e.g., Non-patent Document 2) is problematic due to the loss of a target compound in association with the operation of a click reaction and the occurrence of a nonspecific reaction. In contrast, the method according to the present invention addresses the problems associated with such conventional methods, since the compound to be analyzed is directly used as the low-molecular-weight compound for the Raman spectroscopy method, or an alkyne tag is added to the compound to analyze and a low-molecular-weight compound is prepared, and then the low-molecular-weight compound is subjected to the Raman spectroscopy method.

BRIEF DESCRIPTION OF DRAWINGS

FIG. 2 shows a microscopic Raman spectroscopic device.

FIG. 8-1 shows the detection of an alkyne-labeled peptide.

FIG. 8-2 shows the Raman spectrum of each fraction corresponding to FIG. 8-1C.

FIG. 9-1 shows the separation of an alkyne-labeled peptide and an unlabeled peptide, Raman spectroscopy, and mass spectrometry. FIG. 9-1B is an enlarged view of the UV chromatogram of FIG. 9-1A. FIG. 9-1C shows the alkyne peak obtained from the Raman spectrum (FIG. 9-3G) of each fraction.

FIG. 9-2D shows the mass spectrum of fraction No. 4 and FIG. 9-2E shows the mass spectrum of fraction No. 12. FIG. 9-2F shows the intensities at 1211.5 m/z and 1229/6 m/z of fraction Nos. 1 to 16.

FIG. 9-3 shows the Raman spectrum of each fraction corresponding to FIG. 9-1C.

FIG. 10A shows the online Raman detection method, and FIG. 10B shows the offline Raman detection method.

FIG. 15-1 shows the mass spectrometric device according to the present invention. The left shows MALDI-LTQ-Orbitrap. A sample screened by the Raman spectroscopy method can be directly analyzed using a MALDI ion source-coupled mass spectrometer.

FIG. 15-2 shows the alkyne intensity distribution of spots arranged on a 384-well plate.

FIG. 16 shows that a quartz substrate advantageous for Raman measurement can be directly used for MALDI-MS measurement.

FIG. 19-1 shows the analysis of the binding of cathepsin B to RAT8-AOMK.

FIG. 19-2 shows the alkyne intensity distribution of spots arranged on a 384-well plate.

FIG. 20A shows in the upper section the UV chromatogram. FIG. 20B shows in the lower right section the Raman chromatogram wherein the fraction numbers correspond to those in the upper section. FIG. 20C shows in the lower left section the order of spotting onto the plate.

FIG. 22-1 shows the results of mass spectrometry performed for spots after Raman spectroscopy. Peptides bound to low-molecular-weight compounds having Raman labels were detected from spots for which Raman peaks had been obtained. FIG. 22-1A shows the result of fraction No. 62, B shows the result of fraction No. 60, and C shows the result of fraction No. 57.

FIG. 22-2A shows experimental values and calculated values corresponding to fraction No. 62. FIG. 22-2B shows experimental values and calculated values corresponding to fraction No 0.60. FIG. 22-2C shows experimental values and calculated values corresponding to fraction No. 57.

FIG. 23-1A shows a comparison of the Raman spectrum of RAT8-AOMK itself and the spectra of fraction Nos. 35-75.

FIG. 23-2B shows the Raman spectra of fractions Nos. 51-67.

FIG. 23-2C shows Raman peak intensities at 1609 cm$^{-1}$ and 2107 cm$^{-1}$. The dotted line indicates phenyl ring-derived intensity at 1609 cm$^{-1}$ and the solid line indicates alkyne-derived intensity at 2107 cm$^{-1}$.

EMBODIMENTS FOR CARRYING OUT THE INVENTION

The present invention is described in detail as follows with reference to the drawings.

1. Apparatus According to the Present Invention

Figure 1:
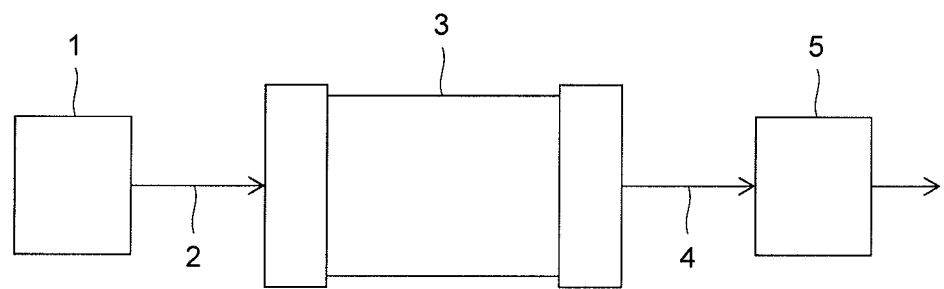
FIG. 1 shows an example of the sample separation unit according to the present invention.
Figure 2:
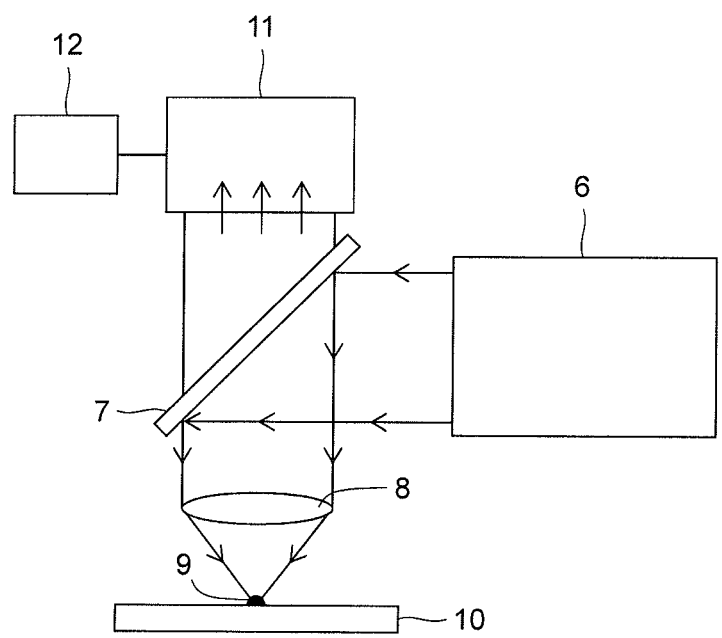
FIG. 2 shows an example of the Raman spectroscopy unit according to the present invention.
Figure 3:
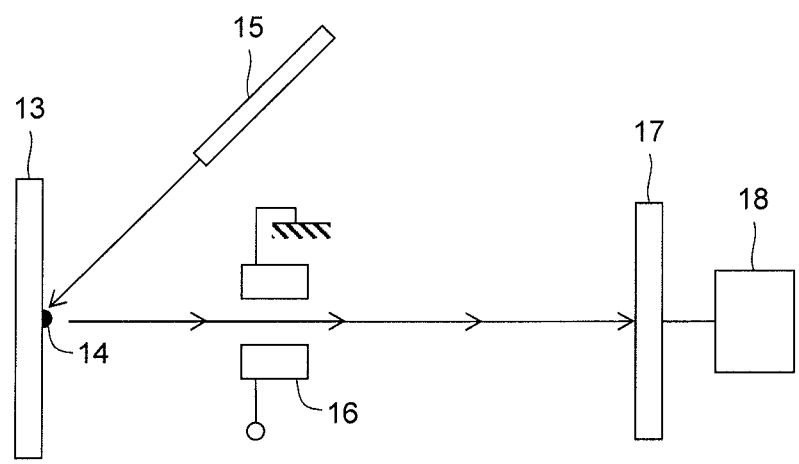
FIG. 3 shows an example of the mass spectrometry unit according to the present invention.

The apparatus according to the present invention comprises a sample separation unit, a Raman spectroscopy unit, and a mass spectrometry unit. The sample separation unit, the Raman spectroscopy unit and the mass spectrometry unit are connected in this order. An example of the sample separation unit is shown in FIG. 1, an example of the Raman spectroscopy unit is shown in FIG. 2, and an example of the mass spectrometry unit is shown in FIG. 3. These units are each described as follows.

1.1 Sample Separation Unit

The sample separation unit according to the present invention is capable of separating various molecules individually in a sample. Specific examples of the sample separation unit include, but are not limited to, a liquid chromatographic device and a capillary electrophoretic device. The sample separation unit can also be an isoelectric focusing device. The term "sample" refers to a sample that may contain a compound of interest being measured. An example of the sample separation unit according to the present invention is shown in FIG. 1. First, a sample is fed from a sample injection unit 1 to a fractionation unit 3 via a liquid-feeding line 2. Subsequently, fractionation is performed in the fractionation unit 3. The fractionation unit 3 can have various chromatography columns, liquid chromatography columns, and capillaries for electrophoresis, but examples thereof are not limited thereto. Next, the fractionated fraction is fed through a liquid-feeding line 4 to a detection unit 5. The detection unit 5 can be an ultraviolet (UV) light detector, for example. The detection means of the detection unit 5 is preferably non-destructive inspection. In FIG. 1, arrows pointing to the right indicate that the separated fraction is subsequently fed to the next Raman spectroscopy unit. In the case of the apparatus according to the present invention, a sample fractionated in the sample separation unit can also be detected by Raman spectroscopy and, therefore, the detection unit 5 in FIG. 1 can also be omitted. That is, FIG. 1 is merely an example and the detection unit 5 is not an essential feature of the sample separation unit.

1.1.1 Liquid Chromatography

The term "liquid chromatography" refers to chromatography that involves the use of a liquid as a mobile phase. In liquid chromatography, substances contained in a mobile phase are eluted at different rates based on differences in the degree of interaction with a solid-phase carrier from a column filled with the solid-phase carrier. A specific substance contained in the mobile phase is separated from other substances using the difference in elution rate. Liquid chromatography separation may be performed based on any principle, and examples thereof include partition, adsorption, molecular exclusion, molecular sieve, and ion exchange. Both normal-phase chromatography and reverse phase chromatography may be used. Preferably, liquid chromatography is high performance liquid chromatography (HPLC) using a liquid pressurized to high pressure as a mobile phase. In liquid chromatography, any solvent can be used as a mobile phase, so long as the solute can be dissolved therein. Examples thereof include water, aqueous solutions, aqueous solutions containing salts, organic solvents, alcohols such as methanol, ethanol, isopropanol, and n-propanol, acetonitrile, dichloromethane, trichloromethane, acetic acid, trifluoroacetic acid, trichloroacetic acid, acetone, cyclohexanone, methylethyl ketone, ethyl acetate, dimethyl carbonate, diethyl carbonate, isooctane, n-hexane, n-heptane, diethyl ether, cyclohexane, toluene, tetrahydrofuran, benzene, dioxane, dimethyl formamide, dimethyl sulfoxide, and appropriate combinations thereof.

When an aqueous solution containing water as a major ingredient is used as the mobile phase for liquid chromatography, basic compounds contained in the aqueous solution can be adsorbed to silanol remaining in the column, causing peak tailing in the chromatogram. To prevent this, separation may be performed by adding an acid such as trifluoroacetic acid. As described below, the solvent used for separation operation is removed after liquid chromatography, so that such acid can be eliminated from the sample to be subjected to the next step.

According to the present invention, Raman measurement can be performed regardless of the presence or the absence of a solvent. However, when Raman measurement of the biological component is performed under a dry condition where the solvent has been removed (offline Raman measurement), the solvent to be used before Raman measurement, such as a low-boiling-point polar solvent is desirably used as the major ingredient of the solvent of a mobile phase for chromatogram. This is because such low-boiling-point polar solvent can readily be removed by vaporization. The term "low-boiling-point polar solvent" refers to a solvent having a low boiling point and polarity, and examples thereof include acetonitrile, methanol, dichloromethane, and trichloromethane and the like. Therefore, as the mobile phase for liquid chromatography, a low-boiling-point polar solvent is preferable. A plurality of types of solvent having different physicochemical properties may be combined to form a mobile phase, and the mixing ratio is varied to provide a concentration gradient for the separation solution, so that the separation capacity for a sample can be also be increased. After liquid chromatography, the solvent used for separation operation is vaporized, and thus the solvent used for liquid chromatography can be removed from the sample to be subjected to Raman measurement. Persons skilled in the art can appropriately set conditions of a separation solvent, a concentration gradient to be applied, and the like depending on the sample to be separated.

1.1.2 Capillary Electrophoresis

The term "capillary electrophoresis" refers to a method that involves performing electrophoresis within sufficiently thin capillaries, and then separating substances contained in a sample. The use of capillaries can suppress the occurrence of convection, and can enhance separation capacity for a substance to a degree higher than that of general electrophoresis. A capillary electrophoretic device typically has capillaries and a voltage applying unit. In general, one part of the capillaries is a sample injection unit and the other part is a sample elution unit. For example, if this is explained in reference to the sample separation unit in FIG. 1, a sample is injected from the sample injection unit 1, separated by the capillaries of the fractionation unit 3, and then fed to the detection unit 5. The sample elution unit may appropriately be connected to a detection unit and/or a fraction collector. Examples of capillary electrophoresis include capillary zone electrophoresis (CZE), micellar electrokinetic chromatography (MEKC), capillary gel electrophoresis (CGE), and capillary isoelectric focusing (cIEF). Persons skilled in the art can appropriately set operational conditions such as the type of solvent and capillary to be used for capillary electrophoresis, as well as the voltage to be applied. Fractions fractionated by capillary electrophoresis can be subjected in a dry state after vaporization of the solvent to the next step in a manner similar to the above liquid chromatography.

1.2 Raman Spectroscopy Unit

The term "Raman spectroscopy unit" as used herein refers to a linear or non-linear Raman spectroscopic device comprising a laser unit for irradiation of a Raman excitation laser beam and a spectral analysis unit for performing spectral analysis of Raman scattering light. FIG. 2 shows microscopic Raman spectroscopic device as an example of the Raman spectroscopy unit according to the present invention. A sample 9 is placed on a sample stand 10, and is analyzed using a Raman microscopic device. Raman excitation laser beam is irradiated from a laser unit 6, reflected by a dichroic filter 7, focused by an objective lens 8, and then irradiated to the sample 9. Raman scattering light is separated by a chromator 11, and then detected at a detection unit 12 by a detection mechanism such as a charge-coupled device (CCD). The spectral analysis unit has a chromator 11 for obtaining Raman scattering spectra in FIG. 2, a detection unit 12, and arbitrary electronic computing unit. In FIG. 2, Raman scattering light that is condensed is indicated with arrows pointing to top/toward the chromator 11. An entrance slit and a lens can be appropriately used for light-condensing. FIG. 2 is merely an example. Examples of the Raman spectroscopy unit according to the present invention further include, not only a Raman microscope (spectroscopic device), but also all known Raman spectroscopic devices such as a dispersive laser Raman spectroscopic device, and a FT-Raman spectroscopic device. For example, a spectral analysis unit contained in the Raman spectroscopy unit according to the present invention may be provided with an instrument for detecting Raman scattering light with an interferometer instead of a chromator. In another possible configuration, a filter with a limited transmission waveband is used for the detection unit for detecting Raman scattering light, and then scattered light that has transmitted through the filter may be directly detected by a detection mechanism such as CCD, without the use of a chromator or the like. In this case, the use of a wavelength tunable filter makes it possible to obtain a Raman spectrum by scanning the transmission waveband. In another possible configuration, a wavelength-tunable laser beam source is used for a Raman excitation laser, and then the wavelength of the excitation laser beam is scanned so as to obtain a Raman spectrum. With any configuration that involves the use of a chromator, an interferometer, a filter, and/or scanning of an excitation laser beam, the intensity of a specific Raman peak and the information of the Raman spectrum of a target sample can be obtained by detecting Raman scattering light. Moreover, as shown in FIG. 2, in another configuration (differing from a configuration in which a sample is placed on a sample stand), a sample is fed through a liquid-feeding line, and then measurement can also be performed namely, "online". Persons skilled in the art can appropriately analyze the presence/absence of a target molecule in a sample on the basis of the pattern (profile) of the thus obtained Raman spectrum. Analysis can also be performed manually or with the aid of an electronic calculator. As the Raman excitation laser, it is possible to use, without limitation, a semiconductor laser, a diode-pumped solid-state (DPSS) laser, a gas laser, a liquid laser, or the like.

1.2.1 Raman Spectroscopy

Figure 4:
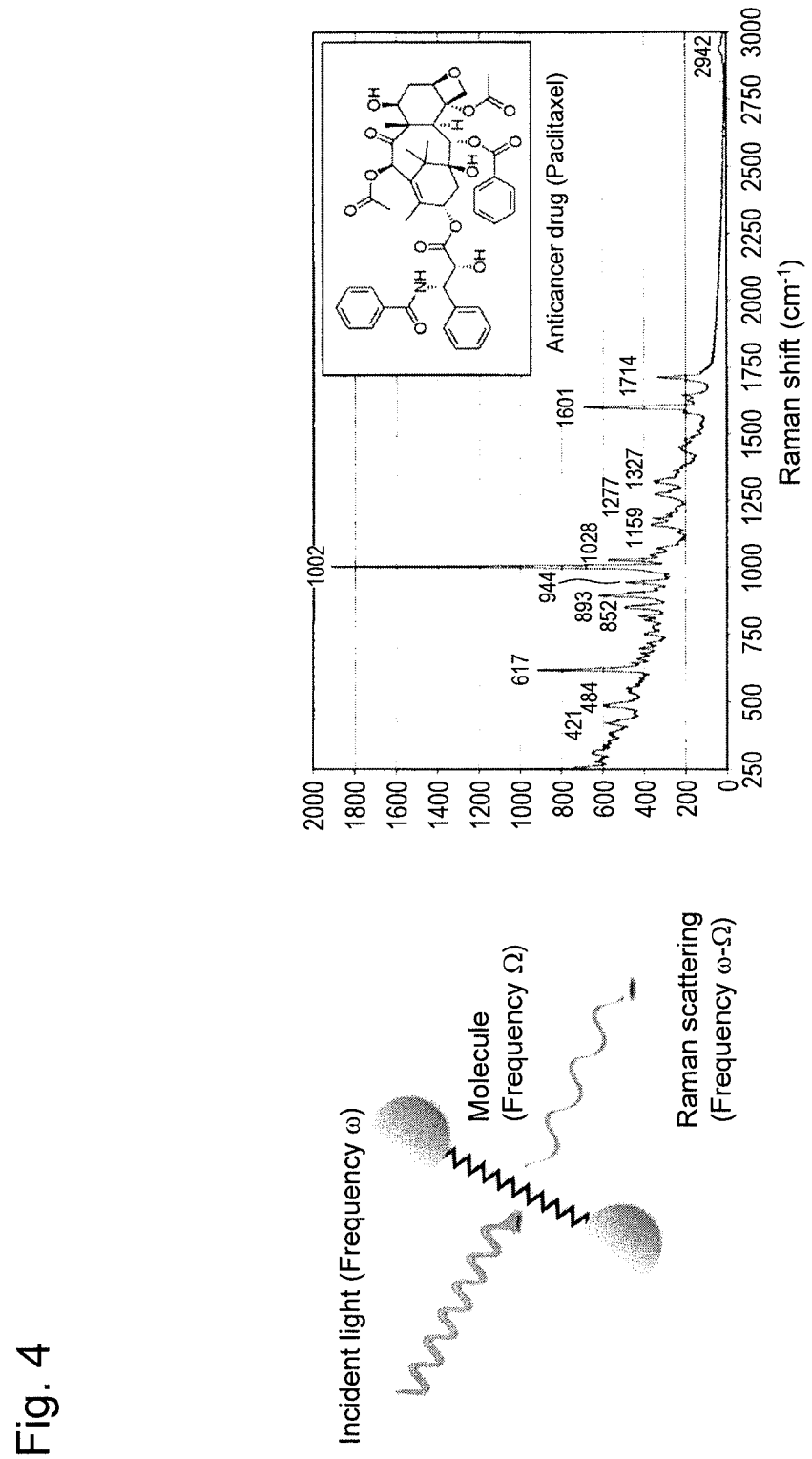
FIG. 4 shows the Raman spectrum of a drug, as obtained by the Raman spectroscopy method. The molecular vibration of the low-molecular-weight compound (paclitaxel) itself is detected as a peak.

Raman spectroscopy is a well-known technique in the technical field. For example, the principle thereof is explained in "Raman Spectroscopy Method" (Edited by Hiroo Hamaguchi and Akiko Hirakawa, Published by The Spectroscopical Society of Japan, Measurement Method Series 17 (*Sokutei-ho* Series 17)). This is briefly explained as follows. The Raman spectroscopy method is a spectral analysis method that is carried out utilizing so-called "Raman effect" such that light with a wavelength differing from that of incident light in scattered light is generated, when light such as a laser beam enters a chemical substance. A difference between the frequency of Raman scattering light and the frequency of incident light is referred to as Raman shift. Since Raman shift is specific to the structure of a molecule, information concerning molecular structures can be obtained by measuring Raman shift. Furthermore, the Raman spectrum of a molecule, the chemical structure of which has been elucidated, can be measured in advance so as to obtain its profile, and then whether or not the molecule is present in a sample can be detected by comparing the Raman spectral pattern of the sample with the afore-mentioned profile. The term "detection" as used herein refers to confirmation of the presence of a compound in a sample. The Raman spectroscopy method has an advantage of being a non-destructive analysis method. The term "linear Raman spectroscopy" also refers to Raman scattering spectroscopy having intensity proportional to the intensity of incident light, which is also referred to as "spontaneous Raman scattering spectroscopy". The term "nonlinear Raman spectroscopy" refers to Raman scattering spectroscopy due to a higher-order nonlinear optical effects, which has intensity proportional to 2nd or higher orders of incident light intensity. Examples of the Raman spectroscopy method include nonlinear Raman spectroscopy methods such as induction Raman scattering, hyper Raman scattering, and coherent anti-Stokes Raman scattering. An example of a Raman spectrum is shown in FIG. 4. As shown in FIG. 4, the molecular vibration of paclitaxel itself is detected as a peak. Raman spectroscopy in this example is described in J. Ling et al., Applied Optic, 41, (28), 6006 (2002). Measurement was performed using a Renishaw Model 2000 Raman Spectroscopic System (Ti: sapphire laser). Specifically, samples used herein were powdery material and measurement was performed with a 20× lens and an exposure time of 30 seconds.

1.2.2 Surface-Enhanced Raman Spectroscopy (SERS)

Figure 12:
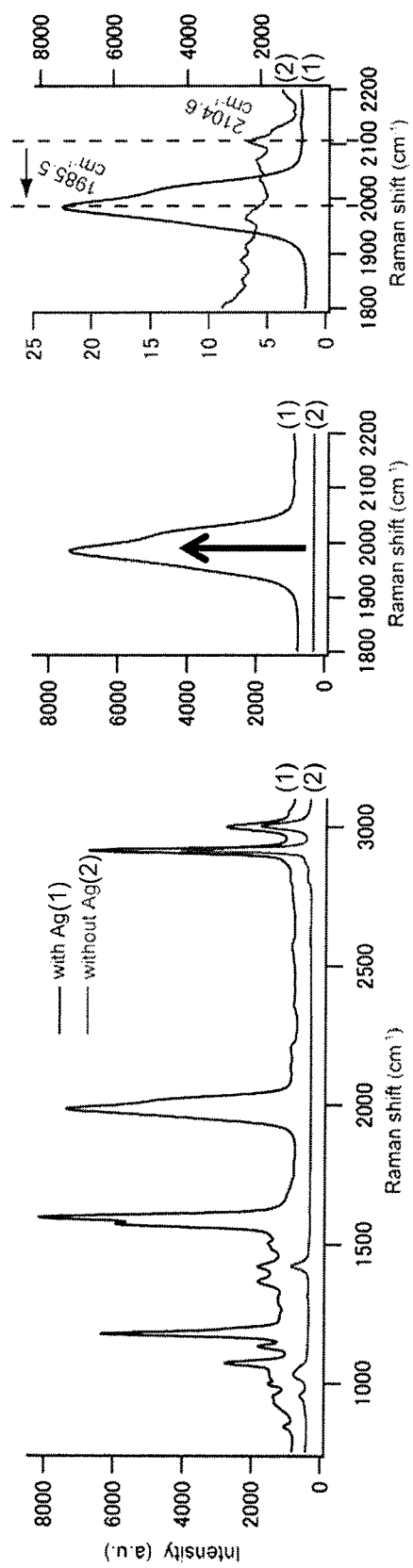
FIG. 12 shows SERS effects. As shown in the SERS and Raman spectrum (exposure time: 10 seconds) of RAT8-AOMK, the Raman intensity of RAT8-AOMK was found to increase by $10^3$ or more when silver nanoparticles with a diameter of 40 nm was used.
Figure 34:
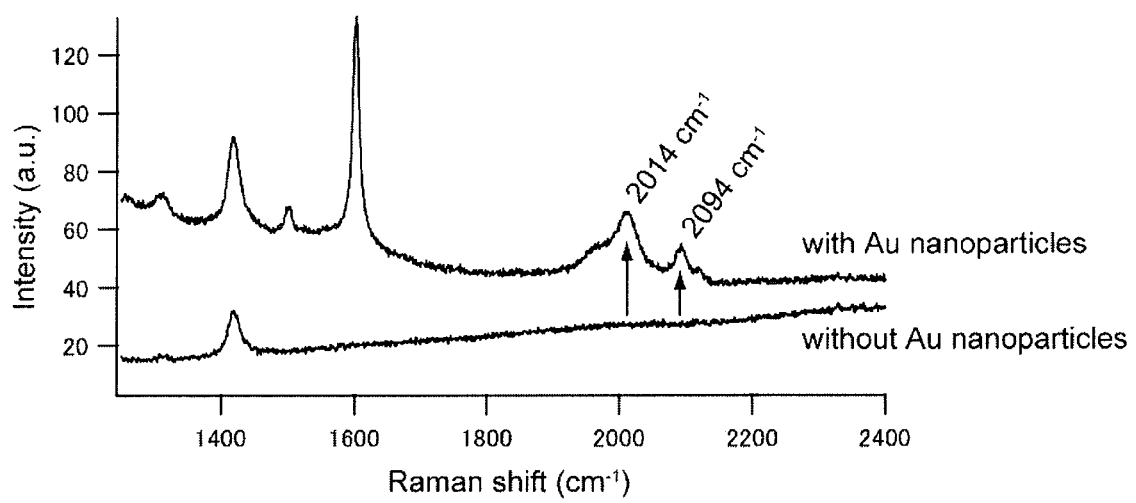
FIG. 34 shows the SERS spectrum of RAT8-AOMK when gold nanoparticles were used. Excitation wavelength used herein was 660 nm. The upper spectrum indicates the result obtained with gold nanoparticles, and the lower spectrum indicates the result obtained without gold nanoparticles.

The present invention provides, in an embodiment, a Raman spectroscopy method using surface-enhanced Raman spectroscopy (SERS). In an embodiment, the surface-enhanced Raman spectroscopy (SERS) of the present invention can be used for the apparatus or the method according to the present invention. A Raman spectroscopy method may generally need prolonged measurement because of weak scattered light. However, SERS can enhance Raman signals and enable rapid measurement. SERS is known as a Raman spectroscopy method by which Raman spectroscopy is performed using metal particulate colloids or substrate containing metal. At this time, metal surface plasmon is excited by a laser, and as a result, an electromagnetic field surrounding the metal increases, thereby enhancing Raman signals generated in proportion to the electromagnetic field. Moreover, chemical interaction including electron transfer takes place between molecules in the vicinity of the metal surface and the metal, thereby enhancing the Raman signal. Either the above electromagnetic or chemical enhancement mechanism, or both mechanisms act to significantly enhance the Raman signal(s) being measured. Examples of metal to be used for SERS include, but are not limited to, iron, cobalt, nickel, tin, indium, germanium, copper, silver, gold, platinum, palladium, aluminum, titanium, and ruthenium. The metal may be in the form of metal nanoparticles, metal nanostructures, or metal nanostructural products. Furthermore, a sample may be coated with a metal membrane. This coating treatment can be performed individually, or a treatment chamber for the above coating treatment may be provided as a part of the Raman spectroscopy unit according to the present invention. An example of SERS effect is shown in FIG. 12. FIG. 12 shows that the Raman peak intensity of RAT8-AOMK was increased by $10^3$ or more when silver nanoparticles having a diameter of 40 nm had been used. The exposure time was 10 seconds. On the left in FIG. 12, the lower spectrum was obtained without using silver particles and the upper spectrum was obtained using silver particles. This similarly applies to the spectra in the center of FIG. 12. As another example, FIG. 34 shows the SERS spectrum obtained when gold nanoparticles were used. In FIG. 34, the lower spectrum was obtained without using gold nanoparticles and the upper spectrum was obtained using gold nanoparticles. As described above, the SERS effect of the present invention is not limited to silver nanoparticles and it is thought that Raman signals are enhanced when metal nanoparticles such as gold nanoparticles are used. The SERS sample can be prepared by: spotting commercially available silver nanoparticles dispersed in an aqueous solution on a cleaned substrate, drying the substrate, and then superimposing a sample thereon, or mixing a sample solution with silver nanoparticles dispersed in an aqueous solution; or spotting a mixed sample and then drying the sample. Moreover, the surface of the substrate can be coated with silver nanoparticles dispersed in an aqueous solution by a mechanical coating method such as a spin-coating method, and then dried. The diameter of the metal nanoparticle is not particularly limited, although a lower diameter is preferred. The term "diameter (size) of the particle(s)" refers to a length that is the same as the diameter of a sphere having the same volume as that of the particle. Also, the term "particles having a diameter of 40 nm" means that an average diameter (obtained as described above) of many particles is 40 nm. Metal nanostructures can vary in shape such as nanorods, nanowires, nanocubes, nanoprisms, and shell structures. The smaller size thereof is again preferable. The size of a metal nanostructure is the longitudinal length of the structure. Further, the phrase, "the size of a metal nanostructure is 40 nm" means that an average size of various metal nanostructures is 40 nm. The size of metal particles, metal nanostructures, or metal nanostructural products is preferably the same as or smaller than the mean free path of electrons vibrating in metal due to light. In particular, in the case of metal particles, the diameter of the particles, and in the case of metal nanostructures or metal nanostructural products, the length of the nanostructure is 200 nm or less, more preferably 100 nm or less, and further preferably 50 nm or less.

As described, Raman spectral signals can be enhanced by the SERS effect, and thus signals can be detected with sensitivity at a practical level.

1.2.2.1 Aggregation-Accelerating Agent

When SERS measurement is performed, an organic acid can be added in order to accelerate the formation of homogeneous aggregates of metal nanoparticles or metal nanostructures, and biomolecules and biomolecules bound to low-molecular-weight compounds. When homogeneously distributed aggregates are formed as a result of the addition of an organic acid, the SERS effect is enhanced, and the operation of setting a laser focal point to be used for Raman spectroscopic measurement is facilitated, so that the time for measurement can be significantly reduced. This is extremely advantageous for automatic measurement. In the present specification, such "acid" to be added to enhance the SERS effect may also be conveniently referred to as "aggregation-accelerating agent" or "additive".

As aggregation-accelerating agents (organic acid) to be used for the present invention, a halogenated organic acid containing a fluorine or chlorine atom within the molecule can be used. Examples thereof include: fluorine-containing organic acids such as trifluoroacetic acid, difluoroacetic acid, monofluoroacetic acid, trifluoromethanesulfonic acid, difluoromethanesulfonic acid, or 3,3,3-trifluoropropionic acid; chlorine-containing organic acids such as trichloroacetic acid, dichloroacetic acid, monochloroacetic acid, trichloromethanesulfonic acid, dichloromethane sulfonic acid, or 3,3,3-trichloropropionic acid; and hydrocarbon-based organic acids such as formic acid, acetic acid, methanesulfonic acid, and propionic acid. Of these, trifluoroacetic acid, difluoroacetic acid, trifluoromethanesulfonic acid, difluoromethanesulfonic acid, 3,3,3-trifluoropropionic acid, formic acid, acetic acid, propionic acid, or methanesulfonic acid is preferred. An organic acid containing a bromine or iodine atom within the molecule has degradability higher than that of a fluorine- or chlorine-containing compound, and is not preferred since it is considered to have almost no effect or rather have an inhibitory effect on SERS because of a reaction between its degradation product and an alkynyl group or the like. In addition, the amount of the aggregation-accelerating agent (organic acid) of the present invention to be added may be any amount as long as the formation of homogeneous aggregates is accelerated, and ranges from 0.001 to 10 mol %, 0.01 to 1 mol %, and preferably ranges from 0.05 to 0.5 mol %, for example.

Persons skilled in the art can readily confirm the formation or the homogeneity of aggregates by preparing a plurality of solutions containing various organic acids with a target molecule or a plurality of solutions containing organic acids with various concentrations with a target molecule, mixing the solutions with metal nanoparticles, arranging the solutions on a plate as droplets, and then microscopically observing the light-field images. By this, organic acids that can be used for the present invention can be confirmed. The appropriate amount(s) of organic acid(s) to add can also be determined. Such screening can be performed with a high throughput by preparing multiple spots on a plate with only routine operation and automated apparatuses, for example.

The aggregation-accelerating agent of the present invention can be used as follows. In an embodiment, an aqueous solution containing the aggregation-accelerating agent of the present invention and a target molecule is mixed with metal nanoparticles, and then target molecule-metal nanoparticle complexes are aggregated. In another embodiment, an aqueous solution containing the aggregation-accelerating agent of the present invention, but containing no target molecule is mixed with metal nanoparticles, and then metal nanoparticles are aggregated. Subsequently, a target molecule is added so that the target molecule interacts with aggregated metal nanoparticles. The present inventors have confirmed that the aggregation-accelerating agent of the present invention has an effect of enhancing not only the detection limit of SERS measurement, but also the correlation between the injection amount of a sample generating SERS signals and SERS signal intensity. Specifically, the aggregation-accelerating agent of the present invention has an effect of stabilizing SERS measurement.

Without wishing to be bound to any particular theory, the effect of the aggregation-accelerating agent of the present invention is thought to be based on the following mechanism. It is thought that when metal nanoparticles are added to and mixed with a solution containing the aggregation-accelerating agent (organic acid) of the present invention and a target molecule, target molecule-metal nanoparticle complexes are formed, and then metal nanoparticles are aggregated together with the target molecule. This mechanism is supported by the fact that aggregate formation is observed even when the aggregation-accelerating agent (organic acid) of the present invention is not used, although the distribution of aggregates is not homogenous and the results of SERS measurement vary. On the other hand, when the aggregation-accelerating agent (organic acid) of the present invention was used, homogeneously distributed aggregates were formed and the SERS effect increased (see Example 12). There is another result that when an excessive amount of a peptide as a target molecule was present, this surpassed the aggregation effect of the aggregation-accelerating agent (organic acid) of the present invention so that no aggregate formation was observed.

1.2.2.2 Surface-Enhanced Raman Spectroscopy (SERS) Using the Aggregation-Accelerating Agent of the Present Invention The aggregation-accelerating agent of the present invention can be used for any sample, as long as SERS measurement can be performed. Specifically, the aggregation-accelerating agent of the present invention can be used not only for a sample that can contain biomolecules, and a sample separated by liquid chromatography or capillary electrophoresis, but also for all other samples for which SERS measurement can be performed. Specifically, SERS measurement using the aggregation-accelerating agent of the present invention can be performed not only for a case of using the apparatus of 1 above, but also for all surface-enhanced Raman spectroscopy (SERS) methods. However, target molecules to be analyzed must be those which can generate a SERS signal. In addition, a target molecule to be preferably used herein is aggregated when mixed together with metal nanoparticles, or interacts with metal nanoparticles aggregated in advance. In this case, a target molecule can be a biomolecule generating SERS signals, a fragment of a biomolecule generating SERS signals, a biomolecule bound to a low-molecular-weight compound generating SERS signals, or a fragment of a biomolecule bound to a low-molecular-weight compound generating SERS signals. A target molecule can be contained in advance in a fraction fractionated by the sample separation unit of 1.1 above through liquid chromatography or capillary electrophoresis, for example.

RAT8-AOMK is explained in 2.2.4 below.

1.2.3 Online Raman Detection and Offline Raman Detection

Figure 10:
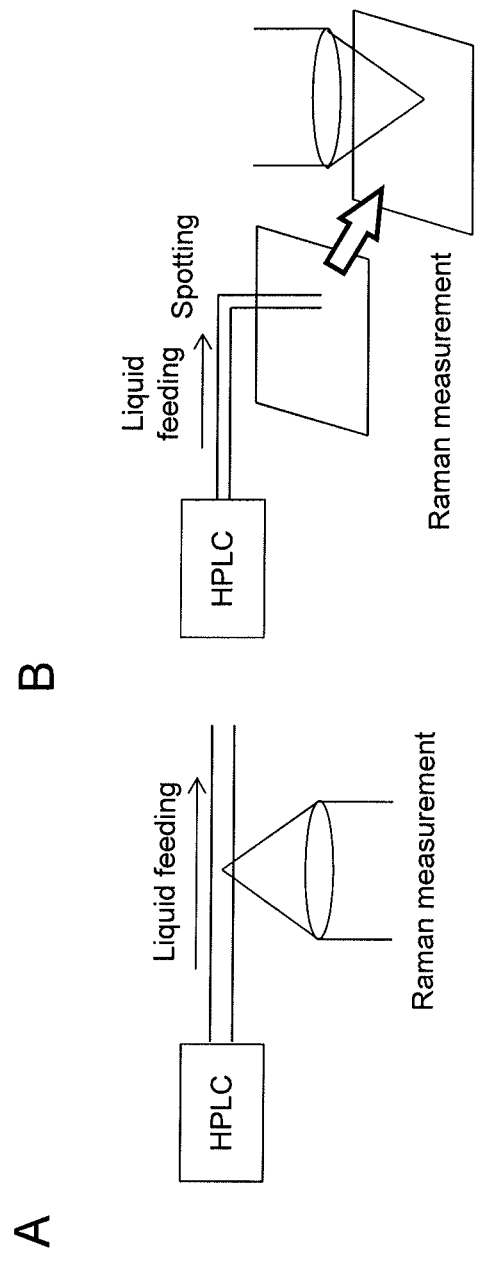
FIG. 10 shows a comparison between online Raman measurement and offline Raman measurement.

The Raman spectroscopy method according to the present invention can be performed as "online" analysis, where measurement is performed while feeding a sample from the sample separation unit. Furthermore, the Raman spectroscopy method according to the present invention can be performed "offline", where measurement is performed by feeding a sample from the sample separation unit, spotting the sample onto a plate, and then performing measurement for the spots. FIG. 10 shows a comparison of the features of online Raman detection method (A) and the features of offline Raman detection method (B). FIG. 10 (A) on the left shows online detection, by which a fed solution (sample) is directly subjected to Raman measurement, and FIG. 10 (B) on the right shows offline detection, by which a fed solution (sample) is once spotted onto a plate, and then spots are subjected to Raman measurement. For example, in the case of online measurement, when Raman peak intensity is insufficient, offline measurement may be performed. Generally, in the case of online measurement, the measurement sensitivity of the Raman spectroscopy method is represented using the unit of mM. However, in the case of offline measurement, the sensitivity is represented using the unit of μM (several picomoles (pmol) in the case of peptide). Whereas online measurement has the problem of contamination of the background light of the solvent, offline measurement can avoid such problem associated with background light by drying and vaporizing the solvent of the spots on the plate. Online measurement is advantageous in that it requires no spotting onto a plate, and thus the configuration of an apparatus may be simple. Persons skilled in the art can appropriately determine that a Raman spectrum should be measured online or offline depending on the concentration of a sample or measurement conditions. Further, the configuration of an apparatus can be appropriately varied depending on the determination.

Figure 11:
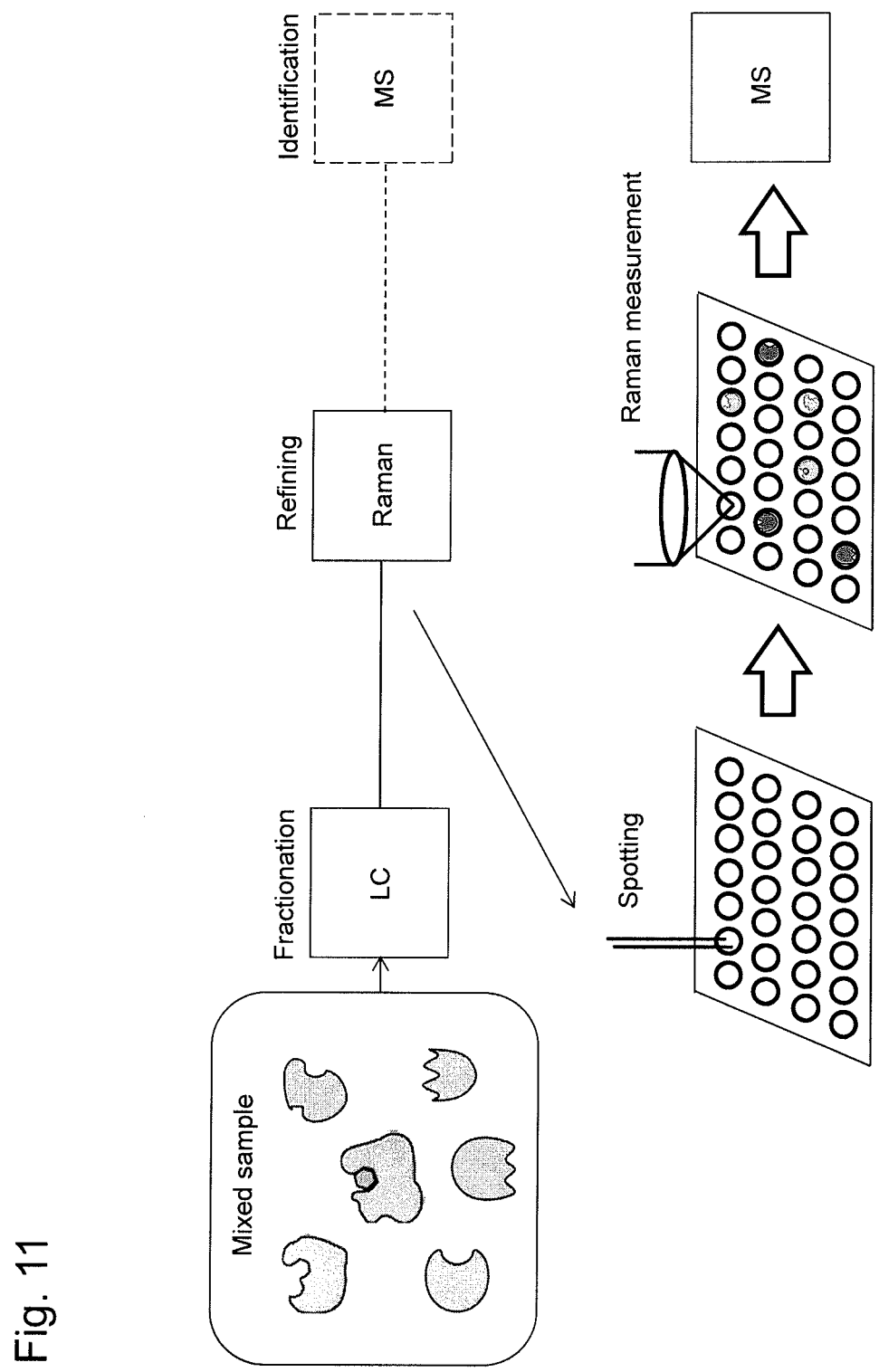
FIG. 11 shows an apparatus according to an embodiment of the present invention.

An embodiment of the apparatus according to the present invention is illustrated in FIG. 11. In this embodiment, a mixed sample is introduced into the sample separation unit, fractionation is performed by liquid chromatography in the sample separation unit, and then the thus obtained fraction is spotted onto a plate. Each spot is dried on the plate for the aggregation of the sample, to improve the measurement sensitivity of Raman spectroscopy. The resulting measurement sensitivity is improved by at least about triple digits, compared with a case where no drying and no aggregation are performed (dissolution state). Furthermore, since Raman spectroscopy is performed offline, measurement can be performed without affection by the background light of a solvent to be used for liquid chromatography and without limitation due to the rate of feeding a sample solution. After Raman spectroscopy, some or all spots showing Raman peaks are subjected to mass spectrometry (MS).

1.2.4 Silent Region

When a cell disruption solution is directly subjected to Raman spectroscopy without fractionation, a region, from which peaks can be detected, and a region, from which no peak or almost no peak is detected, appear. Such region, from which no or almost no Raman peak is detected, when a cell disruption solution is subjected to Raman spectroscopy is referred to as a "silent region" in the present specification (Description). For example, Raman peaks of proteins are mainly observed in the vicinity of 800-1800 $cm^{-1}$ and 2800-3000 $cm^{-1}$, and are almost never detected between 1800 and 2800 $cm^{-1}$. These Raman peaks are all attributed to specific amino acid residues. For example, a tryptophan-derived peak appears in the vicinity of 1011 $cm^{-1}$ and 1554 $cm^{-1}$, an amide-derived peak appears in the vicinity of 1250 $cm^{-1}$ and 1660 $cm^{-1}$, a $CH_2$-derived peak appears in the vicinity of 1430 $cm^{-1}$, and a $CH_3$-derived peak appears in the vicinity of 2933 $cm^{-1}$ (see FIG. 6). However, in a wavelength region of 1800-2800 $cm^{-1}$, almost no biomolecule-derived Raman peak is observed. Therefore, the term "silent region" as used herein may be 1800-2800 $cm^{-1}$. Furthermore, Raman spectroscopy can be performed in a region of 500 $cm^{-1}$ or more, 700 $cm^{-1}$ or more, 1000 $cm^{-1}$ or more, 1200 $cm^{-1}$ or more, 1400 $cm^{-1}$ or more, 1600 $cm^{-1}$ or more, or 1800 $cm^{-1}$ or more, less than 3000 $cm^{-1}$, less than 2900 $cm^{-1}$, less than 2800 $cm^{-1}$, less than 2700 $cm^{-1}$, or less than 2600 $cm^{-1}$. Silent regions are basically the same regardless of the biomaterial(s) being used.

1.3 Mass Spectrometry Unit

The term "mass spectrometry unit" refers to a device for ionizing a molecule contained in a sample by an appropriate ionization method and then measuring the mass spectrum of the molecule. FIG. 3 shows an example of the mass spectrometry unit according to the present invention. A mass spectrometer comprising a combination of a sample unit, a separation unit, and an analysis unit composes the mass spectrometry unit according to the present invention. In the sample unit, first a sample 14 is placed on a sample stage 13. Next, the sample is ionized by an appropriate ionization means, and is then caused to fly within the apparatus by electrostatic force. FIG. 3 illustrates a laser unit 15 as an ionization means. Ions that are caused to fly in an accelerated manner by an acceleration electrode 16 are separated depending on mass-charge ratios in the separation unit by an electric or magnetic effect, for example. Subsequently, the resultants are detected by an ion detector 17 in the analysis unit, so that a mass spectrum can be obtained. The ion detector 17 is preferably connected to a signal processing unit 18. The thus obtained signals are processed by preferably an electronic calculator. In the present specification, the ion detector 17, the signal processing unit 18, and an arbitrary electronic calculator are collectively referred to as the "analysis unit" of a mass spectrometer. A mass spectrum obtained by processing signals in the analysis unit are generally represented by plotting mass-charge ratios (m/z) along the horizontal axis, and detection intensities along the vertical axis. Examples of an ionization method for mass spectrometry include matrix assisted laser desorption/ionization (MALDI), electrospray ionization (ESI), atmospheric pressure chemical ionization (ACPI), electron ionization (EI), and chemical ionization (CI). Persons skilled in the art can appropriately change and optimize the configuration of a mass spectrometric device depending on these ionization means. For example, the MALDI method involves mixing a sample in a matrix such as an aromatic organic compound to prepare crystal, and then irradiating a laser thereto for ionization. Examples of a matrix to be used herein include, but are not particularly limited to, α-cyano-4-hydroxycinnamic acid (CHCA), sinapinic acid (SA), trans-4-hydroxy-3-methoxycinnamic acid (ferulic acid), 3-hydroxypicolinic acid (HPA), 1,8-dihydroxy-9,10-dihydroanthracene-9-one (dithranol), and 2,5-dihydroxybenzoic acid (DHB). The MALDI method is advantageous in that even a macromolecular compound such as a protein can be stably ionized without disrupting the molecule.

1.3.1 Mass Separation Unit

An ionized sample is separated in the separation unit to be used for mass spectrometry. Examples of the type of the separation unit include time-of-flight, magnetic deflection, quadrupole, ion trap, and Fourier transform. Mass spectrometry performed with a time-of-flight (TOF) separation unit involves accelerating an ionized sample in a pulsatile fashion, and then detecting a time difference in time for ions to reach a detector. Mass can be calculated from the time difference. In this case, an acceleration electrode 16 shown in FIG. 3 is disposed only in a portion of the space within which ions fly, so that acceleration is performed in a pulsatile fashion. At this time, neither electric field nor magnetic field is applied to most of the space in which the ions fly. Such separation unit may be combined with any one of the above ionization methods, and a combination of MALDI and TOF is particularly preferable. Such configuration may also be referred to as a MALDI-TOF mass spectrometer.

1.3.2 MS/MS Analysis

In an embodiment of the present invention, mass spectrometry can be MS/MS analysis. MS/MS analysis involves performing mass spectrometry in tandem. This method involves extracting only specific ions in the first separation unit, splitting them, and then analyzing the thus generated fragment ions in the second separation unit. Fragment ions can be analyzed with a single device, or two different devices. For example, when a protein is digested with protease to obtain peptides, and MS/MS analysis is performed for the peptide fragments, peaks resulting from sequential fragmentation of peptides are detected, and the amino acid sequences of the peptides can be determined based on the mass information of the peaks. MS/MS analysis is a well-known technique in the technical field. For example, see A. K. Shukla et. al., J. Mass Spectrum. 35, 1069 (2000).

1.4 Configuration of the Apparatus According to the Present Invention

Figure 5:
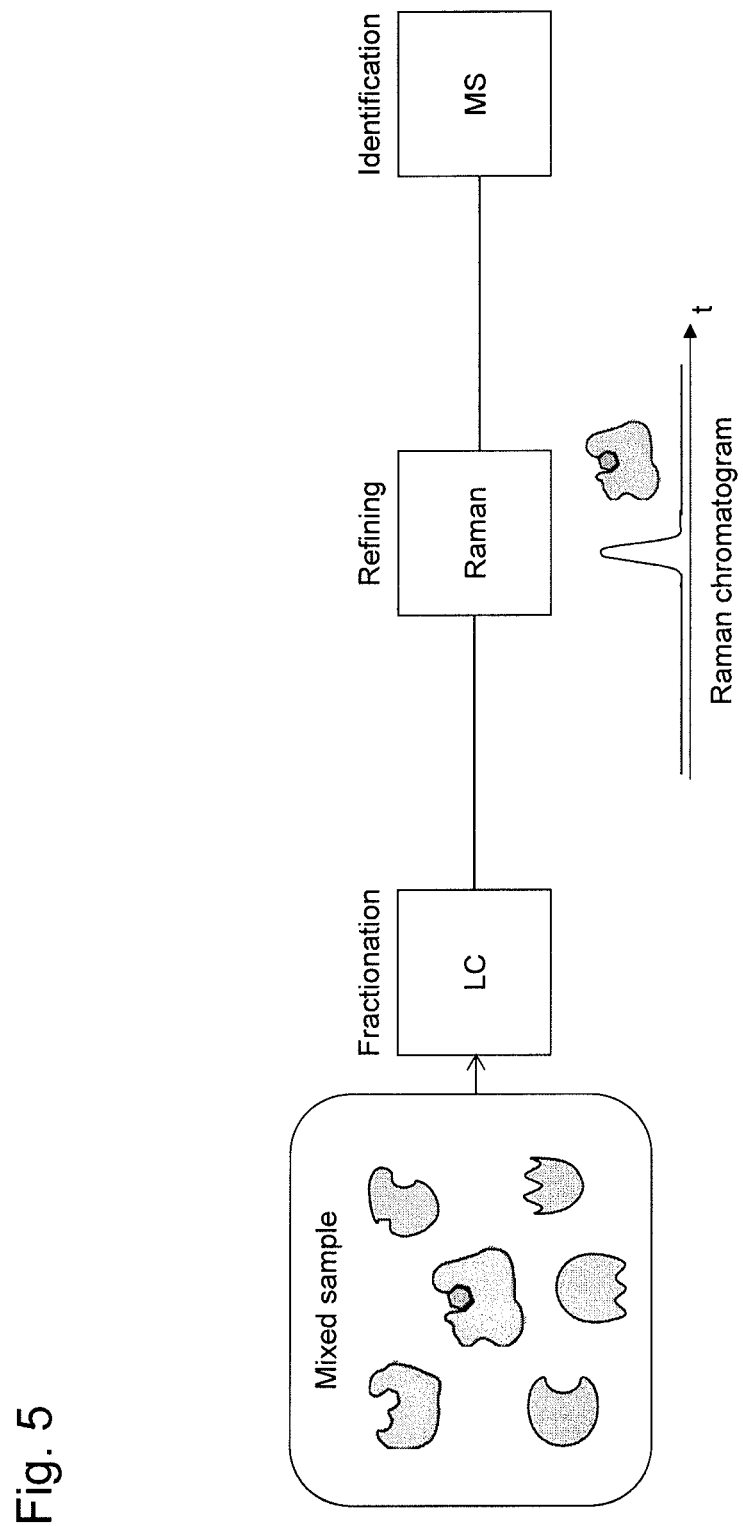
FIG. 5 shows an LC-R-MS device according to the present invention.

In an embodiment, the apparatus according to the present invention has a liquid chromatographic device, a Raman spectroscopic device, and a mass spectrometer (LC-R-MS). An example thereof is shown in FIG. 5. A mixed sample is fractionated by liquid chromatography (LC), and fractions in which a low-molecular-weight compound (drug) is present are refined using the Raman spectroscopy method. Furthermore, fractions exhibiting Raman peaks can be analyzed by a mass spectrometer (MS), and a biomolecule that binds to the low-molecular-weight compound can be specified. In another embodiment, the apparatus according to the present invention has a capillary electrophoretic device, a Raman spectroscopic device, and a mass spectrometer (CE-R-MS). This case is also similar to the case of LC-R-MS and shares the same basic principle of the present invention, except for separating a sample using a capillary electrophoretic device (CE). Furthermore, liquid phase isoelectric focusing or the like can also be used as the sample separation unit. This similarly applies to a case where the sample separation unit is based on another separation means.

The apparatus according to the present invention comprises the sample separation unit, the Raman spectroscopy unit, and the mass spectrometry unit connected in this order. The term "connection (connected)" as used herein means that instruments of the apparatus are connected to each other so that a sample can be transferred. The expression, "the sample separation unit, the Raman spectroscopy unit, and the mass spectrometry unit are connected in this order" means that specifically, the apparatus is configured, so that a sample is transferred in the following order, namely, a sample separated in the sample separation unit is introduced into the Raman spectroscopy unit, and then the sample subjected to Raman spectroscopy is introduced into the mass spectrometry unit. The sample can be transferred from the sample separation unit to the Raman spectroscopy unit, and from the Raman spectroscopy unit to the mass spectrometry unit manually or using an automated device. The sample can be transferred continuously via a liquid-feeding line, or the sample can also be intermittently transferred by spotting the sample once on a plate or the like, and then performing separation using a fraction collector into individual fractions.

Therefore, the sample separation unit, the Raman spectroscopy unit, and the mass spectrometry unit may be physically individual devices. A system, wherein a separated sample (fraction) is introduced manually or by an automated device from the sample separation unit into the Raman spectroscopy unit, and then the analyzed sample (fraction) from the Raman spectroscopy unit is introduced manually or by an automated device into the mass spectrometry unit, is also included in the apparatus or the method according to the present invention. Alternatively, the apparatus according to the present invention can also be an integrated apparatus in which the sample separation unit, the Raman spectroscopy unit, and the mass spectrometry unit are incorporated. The apparatus according to the present invention having such configuration can overcome the problems of prior art.

2. Method According to the Present Invention

The present invention provides a method for specifying a biomolecule, and a method for identifying the binding site of a biomolecule and a low-molecular-weight compound using the apparatus according to the present invention.

That is, according to a method of the present invention, a biomolecule or fragment(s) thereof bound to a low-molecular-weight compound distinguishable by the Raman spectroscopy method can be fractionated by the sample separation unit, each fractionated fraction (e.g., droplets) can be arranged on a plate, and then dried and the aggregated biomolecule or fragment(s) thereof can be directly measured in the Raman spectroscopy unit, without the need of any complicated pretreatment and the like. Subsequently, all fractions or some fractions specified as having Raman peaks can be directly analyzed by the mass spectrometry unit without special treatment.

2.1 Biomolecule

The apparatus or the method according to the present invention analyzes biomolecules. The term "biomolecule(s)" as used herein refers to a protein, a peptide, a nucleic acid, a sugar, or a lipid that exists extracellularly or intracellularly. The term "biomolecule(s)" as used herein may be derived from any living body or organism, such as viruses, prokaryotes, eukaryotes, fungi, plants, higher plants, animals, insects, higher animals, mammals, rodents (e.g., mice and rats), primates (e.g., monkeys and chimpanzees), and humans, or cultured cells or cultured tissues thereof. The terms "protein" and "peptide" included in the biomolecules as used herein refer to a macromolecular compound in which natural and/or synthetic amino acids are bound via a peptide bond(s). The term "nucleic acid" included in the biomolecule(s) as used herein refers to a single-stranded or double-stranded nucleic acid(s) containing at least 10, preferably 50, 300, 500, or 1000 or more nucleotides, and preferably interacts with a specific low-molecular-weight compound. A nucleic acid may be DNA or RNA. Examples of RNA include tRNA and ribosome RNA, and ribozyme. A nucleic acid can contain a promoter region, an enhancer region, a silencer region, and a terminator region. These examples preferably bind to a specific transcriptional regulatory factor, a transcription initiation factor, and the like. Examples of a sugar included in the biomolecule(s) as used herein include polysaccharides that preferably interact with specific low-molecular-weight compounds. Examples of such sugar include proteoglycans or derivatives thereof such as hyaluronic acid, chitin, heparan sulfate, keratan sulfate, dermatan sulfate, sialic acid, and chondroitin sulfate. Examples of the term "lipid" included in the biomolecule(s) as used herein include lipids that are contained in the above illustrated organisms, and preferably interact with specific low-molecular-weight compounds. Examples of such lipid include phospholipids such as a sphingophospholipid and a glycerophospholipid, glycolipids such as a sphingoglycolipid and a glyceroglycolipid, and conjugated lipids that form extracellular or cell membranes, such as a lipoprotein lipid, a sulpholipid and a galactolipid.

2.2 Low-Molecular-Weight Compound

The term "low-molecular-weight compound according to the present invention" refers to a candidate compound that has a low molecular weight and binds to or can bind to a specific biomolecule. In an embodiment, the low-molecular-weight compound according to the present invention has a molecular weight lower than that of a biomolecule. When a low-molecular-weight compound binds to a specific biomolecule, such biomolecule may be referred to as the "target" of the low-molecular-weight compound. Examples of a low-molecular-weight compound or a compound serving as a base for a low-molecular-weight compound (also referred to as an analyte compound) include drugs, drug candidate compounds, biologically active substances, metabolites, vitamins, hormones, ligands that bind to specific receptor proteins, protein agonists, protein antagonists, and compounds that bind to proteins through a post-translational modification mechanism of a protein. These examples further include compounds existing in the nature and analogs having chemical structures analogous to those thereof. The low-molecular-weight compound according to the present invention may be any compound, as long as it exhibits a scattering peak distinguishable from that of a biomolecule, as measured by Raman spectroscopy, or it exhibits a scattering peak distinguishable from that of a biomolecule, as measured by Raman spectroscopy using a Raman label.

2.2.1 Raman Peak of Low-Molecular-Weight Compound

A compound having a characteristic Raman peak or a Raman peak distinguishable from that of a biomolecule co-existing therewith within cells or a mixture, and particularly a biomolecule targeted by a low-molecular-weight compound, can be directly used as a low-molecular-weight compound in the present invention. Such low-molecular-weight compound can be directly detected by Raman spectroscopy, and thus has the advantage of not requiring any modification with a fluorophore or the like. Incidentally, a region of 500-1800 $cm^{-1}$, where a compound-derived Raman peak is observed, may also be referred to as "finger print region".

2.2.2 Raman Label

Furthermore, in the case of compounds which do not have any characteristic Raman peaks, a substituent having an extremely small effect on binding with a biomolecule even when introduced into the compound can be introduced into the compound and then the resultant compound can be used as the low-molecular-weight compound according to the present invention. Such substituent may also be referred to as a Raman label. The substituent or the Raman label preferably has a scattering spectrum in the silent region. The term "silent region" refers to, as explained above, a wavenumber region where almost no or no signals are observed in the Raman spectrum derived from biomolecules. The above substituent or Raman label has a relatively strong Raman scattering light, and exhibits a peak characteristic to a wavenumber region different from those of biomolecule-derived Raman peaks when the target low-molecular-weight compound is detected. Therefore, the above substituent or Raman label are convenient for selectively detecting a target low-molecular-weight compound with high sensitivity, and can be directly detected by the Raman spectroscopy method without the need of modification with a fluorophore or the like. Examples of substituents having a scattering spectrum in the silent region include, but are not limited to, compounds containing an alkynyl group, a nitrile group (—C≡N), deuterium (C-D, C-D$_2$, C-D$_3$), a diazonio group (—N+≡N), an isocyanate ester group (—N═C═O), an isonitrile group (—N$^+$≡C$^-$), a ketene group (>C═C═O), a carbodiimide group (—N═C═N—), a thiocyanate ester group (—N═C═S), an azide group (—N═N$^+$═N$^-$), a diazo group (>C$^+$═N$^-$═N), an alkynediyl group, an ethynylene group (—C≡C—), 1,3-butadienylene (—C≡CC≡C—), and the like (also see, Edited by Hiroo Hamaguchi and Akiko Hirakawa., Raman spectroscopy method (The Spectroscopical Society of Japan, Measurement Method Series 17 (*Sokutei-ho* series 17)). Examples of an alkynyl group include, but are not limited to, an ethynyl group (CH≡C—), a propargyl group (CH≡CCH$_2$—, also referred to as a 2-propynyl group), a buta-3-yne-1-yl group (HC≡CCH$_2$CH$_2$—), and a buta-2-yne-1-yl group (CH$_3$—C≡CCH$_2$—). These examples can all be used as Raman labels in the present invention. The low-molecular-weight compound according to the present invention preferably has an alkynyl group, a nitrile group, or deuterium.

2.2.3 Spacer

The Raman label may be directly introduced into a target compound, or bound to a target compound via an appropriate spacer molecule. For example, when an alkynyl group is introduced into a target compound, the alkynyl group may be directly introduced, or an alkynyl group (ethynylphenyl group) bound to a phenyl group can be introduced. In this case, the spacer molecule is a phenyl group. Therefore, a compound that binds to a specific biomolecule, but has no characteristic Raman peak or no Raman peak distinguishable from those of biomolecules is Raman-labeled by introducing the above substituent, and thus can be used for the apparatus or the method according to the present invention. Persons skilled in the art can label a compound with a Raman label using an appropriate spacer molecule. Examples of a spacer molecule include, but are not limited to, a methylene group (—CH$_2$—), an ethylene group (—CH$_2$CH$_2$—), a propane-1,3-diyl group (—CH$_2$CH$_2$CH$_2$—), a phenylene group (—C$_6$H$_4$—), an oxyethylene group (—OCH$_2$CH$_2$—), and an oxypropylene group (—OCH$_2$CH(CH$_3$)—).

2.2.4 Raman Label Method

Figure 24:
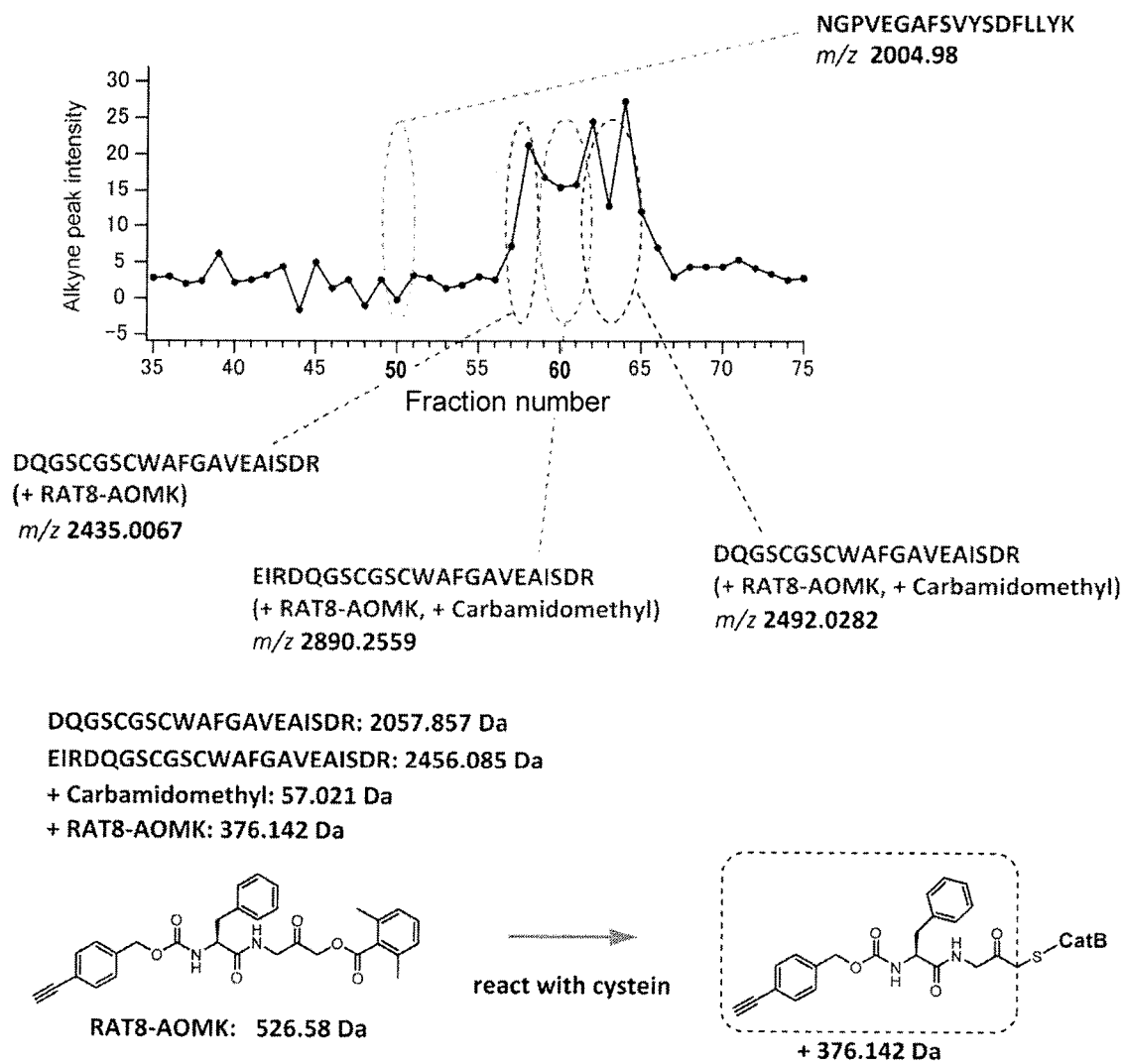
FIG. 24 shows the distribution of a RAT8-AOMK-labeled peptide and an unlabeled peptide. The lower section of FIG. 24 shows the structures and the molecular weights of RAT8-AOMK before and after binding to cathepsin B.

Persons skilled in the art can appropriately select the position to introduce the Raman label as well as the type of Raman label to introduce by considering the structure of the compound. Moreover, persons skilled in the art having general techniques in the field of organic synthesis can appropriately synthesize a Raman-labeled compound as the low-molecular-weight compound according to the present invention. This is explained with a specific example as follows. Persons skilled in the art can synthesize an AOMK derivative (hereinafter, also referred to as RAT8-AOMK) by Raman-labeling acyloxymethyl ketone (AOMK) (an inhibitor of cathepsin B) with alkyne using general techniques in the field of organic synthesis. The RAT8-AOMK binds to cathepsin B, so as to inhibit its enzyme activity. The activity of RAT8-AOMK to inhibit cathepsin B is represented by IC$_{50}$=0.3 μM. RAT8-AOMK can be synthesized and obtained by reacting N-Boc-AOMK (IC$_{50}$=0.05 μM) with 4-nitrophenyl-4-ethynylbenzyl carbonate. Acyloxymethyl ketone (AOMK) is known as a cysteine protease inhibitor. The principle thereof is that a cysteine residue of the active center of an enzyme protein is modified by AOMK, and thus activity as protease is diminished (see FIG. 24).

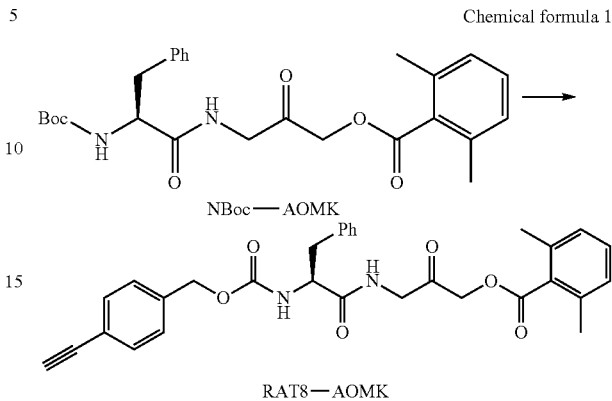

Chemical formula 1

NBoc—AOMK

RAT8—AOMK

Persons skilled in the art can determine the position to introduce the Raman label by considering that introduction of a Raman label into a site distant from the methylketone group within an AOMK compound would have almost no effect on the cysteine residue modification reaction. Furthermore, a "Raman-labeled compound library" can be constructed by exhaustively introducing Raman labels into arbitrary positions within a compound, the Raman-labeled compound library can be screened for the presence or the absence of predetermined biomolecule binding activity, such as protein inhibitory activity, compounds having Raman labels introduced therein and binding to a target protein can be selected from among various candidate compounds, and thus these compounds can be used as the low-molecular-weight compound(s) according to the present invention.

2.2.5 Examples of a Low-Molecular-Weight Compound

When the biomolecule is a protein or a peptide, examples of the low-molecular-weight compound according to the present invention include those binding to such protein or peptide, drugs, drug candidate compounds, antibiotics, biologically active substances such as an agricultural chemical, metabolites, vitamins such as a coenzyme, hormones, ligands binding to specific receptor proteins, protein agonists, protein antagonists, and compounds that bind to proteins via a post-translational modification mechanism of a protein. Such low-molecular-weight compound is preferably Raman-labeled, or has a characteristic Raman spectrum distinguishable from the spectrum of other biomolecules. As an example, regarding compound N-Boc-AOMK which is a compound that binds to the protein cathepsin B, an alkyne group can be introduced into the compound as a type of Raman label with the use of 4-nitrophenyl-4-ethynylbenzyl carbonate, thereby preparing the low-molecular-weight compound according to the present invention, RAT8-AOMK.

When the biomolecule is a nucleic acid, examples of the low-molecular-weight compound according to the present invention include intercalating drugs for double-stranded nucleic acids such as proflavine and actinomycin D, group binding drugs such as netropsin and distamycin, and DNA cleaving drugs such as calichemicin, which bind to such nucleic acids. These low-molecular-weight compounds are preferably Raman-labeled, or have characteristic Raman spectra distinguishable from the spectra of other biomolecules.

When the biomolecule is a sugar, examples of a low-molecular-weight compound include low-molecular-weight antibiotics exhibiting lectin-like activity, such as pradimicin A, B, C, D, E, FA-1, FA-2, and benanomicin A.

These low-molecular-weight compounds are preferably Raman-labeled, or have characteristic Raman spectra distinguishable from the spectra of other biomolecules.

Examples of the substance according to the present invention, which do not necessarily have a low molecular weight, but binds to such sugar, include lectins comprising R-type lectins, C-type lectins such as calnexin, calreticulin, selectin, and colectin, galectin, leguminous lectin, L-type lectins, P-type lectins, and I-type lectins such as annexin and siglec, and specific antibodies of sugar chains. These substances also bind to biomolecules, and, therefore, are encompassed in the examples of the low-molecular-weight compound of the present invention. An alkyne group can be introduced into a specific antibody that binds to a sugar by incorporating an amino acid modified with alkyne into the protein using genetic engineering techniques.

When the biomolecule is a lipid, examples of the low-molecular-weight compound according to the present invention include polyether-based antibiotics such as monensin, lasalocid, and salinomycin, anesthetics such as isoflurane, sevoflurane, desflurane, and fat-soluble vitamins such as vitamin A (retinoid), vitamin D, vitamin E, and vitamin K, which act on such lipid. These low-molecular-weight compounds are preferably Raman-labeled, or have characteristic Raman spectra distinguishable from the same of other biomolecules.

Figure 6:
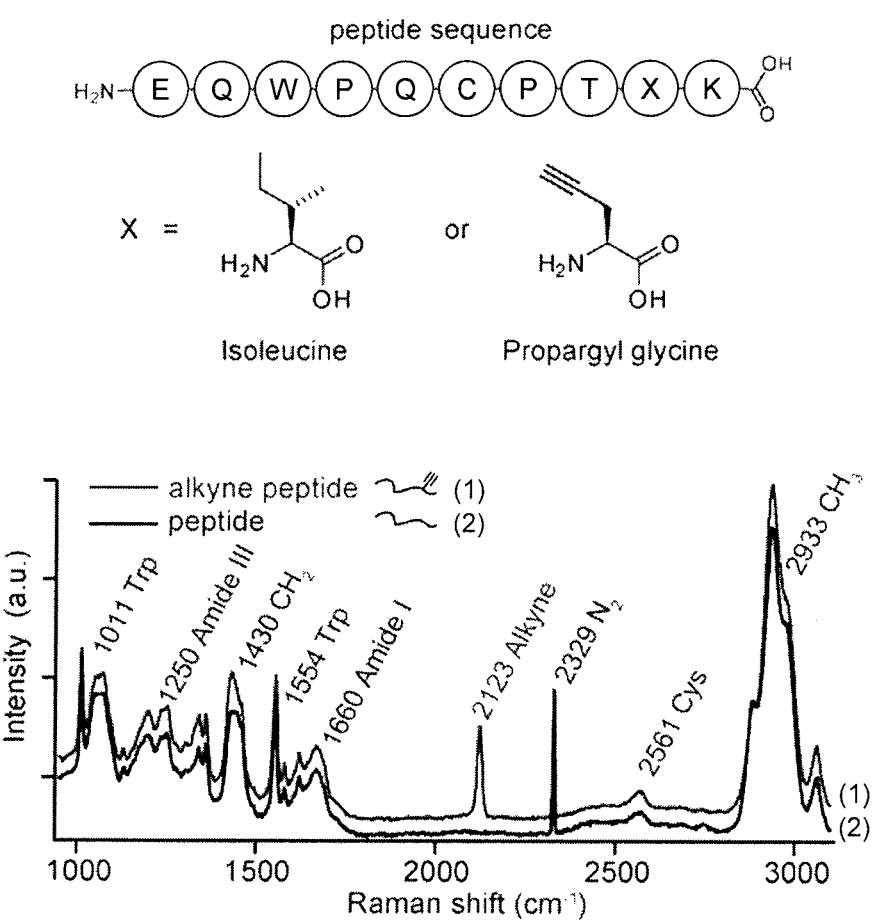
FIG. 6 shows the Raman spectra of an alkyne-labeled peptide and an unlabeled peptide. The spectra show the attribution of the peptide-derived Raman peaks. (1) indicates the alkyne-labeled peptide and (2) indicates the unlabeled peptide.

In one embodiment, the low-molecular-weight compound according to the present invention is a Raman-labeled amino acid. In another embodiment, the low-molecular-weight compound according to the present invention is a low-molecular-weight peptide having a Raman-labeled amino acid. FIG. 6 shows an example of an alkyne-labeled peptide and its Raman spectrum. Specifically, FIG. 6 shows the Raman spectra of a peptide in which X is isoleucine (hereinafter, referred to as peptide 1. In FIG. 6, (2).) and a peptide in which X is propargyl glycine (hereinafter, referred to as alkyne peptide 1. In FIG. 6, (1).) in the amino acid sequence of EQWPQCPTXK (SEQ ID NO: 4). While a Raman peak unique to alkyne was observed at 2123 $cm^{-1}$ in the spectrum of the alkyne-labeled peptide, no such Raman peak was observed within the region in the case of the unlabeled peptide. As such, both peptides can clearly be distinguished from each other by the Raman spectroscopy unit according to the present invention. The use of this principle enables the following embodiment. Focusing on a low-molecular-weight peptide with bioactivity, Raman-label one or more amino acids thereof, or prepare a peptide substituted with a Raman-labeled amino acid(s). With the use of the Raman-labeled low-molecular-weight peptide, a biomolecule that binds to the peptide can be specified by the apparatus or the method according to the present invention. Moreover, the binding site of the peptide and the biomolecule can be identified. Specifically, a target of a low-molecular-weight peptide (e.g., a peptide hormone) having bioactivity can be searched for and the site of action can be identified. An alkyne-labeled peptide can be prepared by a solid phase synthesis (Fmoc) method. This is explained with reference to the above example. The amino acid, propargyl glycine (X), is added following lysine (K) by a solid phase synthesis method, and then the amino acid sequence, TPCQPWQE, is added sequentially in order from the C-terminus, and as a result, an alkyne-labeled peptide can be obtained. In another example, the peptide is synthesized in advance by a solid phase synthesis method, and an arbitrary side-chain functional group may be alkyne-labeled in the peptide thereafter.

2.3 Binding of a Low-Molecular-Weight Compound and a Biomolecule

When a low-molecular-weight compound is "bound" to a biomolecule in the present specification, examples of "binding (bond)" include a covalent bond, a coordinate bond, and interaction. The term "bound (to)" refers to binding of a low-molecular-weight compound to a specific site in a biomolecule. The term "covalent bond" refers to a chemical bond formed by a plurality of atoms sharing their electrons. The term "coordinate bond" refers to a chemical bond wherein an electron(s) is provided from only one of atoms participating in binding. The term "interaction" refers to the effect based on intermolecular force between two molecules, and examples thereof include ion-to-ion interaction, action by a hydrogen bond, dipole-dipole interaction, hydrophobic interaction, and combinations thereof.

3. Method for Identifying the Binding Site of a Biomolecule and a Low-Molecular-Weight Compound The term "identifying" the binding site of a biomolecule and a low-molecular-weight compound means to determine the site of the biomolecule to which the low-molecular-weight compound binds or interacts. The binding site of a biomolecules and a low-molecular-weight compound can be identified using the apparatus according to the present invention.

The method for identifying the binding site of a biomolecule and a low-molecular-weight compound comprises the following steps of:

(1) subjecting fractionated fragments of a biomolecule bound to a low-molecular-weight compound, to Raman spectroscopy; and (2) subjecting all or some fractions subjected to Raman spectroscopy, to mass spectrometry.

This method comprises detecting fractions having the Raman peak derived from the low-molecular-weight compound bound to a fragment of the biomolecule by Raman spectroscopy, obtaining the mass spectrometric results of fractions having the low-molecular-weight-compound-derived Raman peak, comparing the results with the mass information of the biomolecule, and thus identifying the binding site of the low-molecular-weight compound within the biomolecule.

As a step prior to this method, first a low-molecular-weight compound can be bound to a biomolecule, the biomolecule bound to the low-molecular-weight compound can be fragmented, and then fragments can be fractionated. These fractions can be used for the above step (1). For binding of a low-molecular-weight compound to a biomolecule, the low-molecular-weight compound and the biomolecule are preferably mixed under acellular conditions, for example.

3.1 Fragments of a Biomolecule

The term "fragments of a biomolecule" as used herein refers to fragments prepared by cleaving the bond(s) of a biomolecule (a macromolecular compound) at one or more positions into units having molecular weights lower than that of the biomolecule. For example, when the biomolecule is a protein, this is subjected to protease treatment, so that fragments (peptides) can be obtained as a result of cleavage of peptide bonds. Examples of protease include, but are not limited to, serine protease, aspartic acid protease, metalloprotease, and cysteine protease. Furthermore, the biomolecule can also be chemically degraded using cyanogen bromide, N-bromosuccinimide, hydroxylamine, or the like. This similarly applies to a case when the biomolecule is a peptide. When the biomolecule contains a triglyceride lipid, this is subjected to treatment with a lipid-degrading enzyme such as lipase, so that the degraded fragments (fatty acids) can be obtained. Examples of lipase include, but are not limited to, triacylglyceride lipase, phospholipase, lipoprotein lipase, and esterase. This similarly applies to other types of biomolecule. When the biomolecule is a sugar, a sugar-degrading enzyme can be used, and examples thereof include, but are not limited to, α-amylase, β-amylase, glucoamylase, isoamylase, pullulanase, maltotriohydrolase, α-glucosidase, cyclodextrin, glucanotransferase, amyloglucosidase, dextranase, β-galactosidase, sialidase, cellulase, α-mannosidase, and β-mannosidase. When the biomolecule is a nucleic acid, this is treated with nucleases such as deoxyribonuclease (e.g., a restriction enzyme that specifically cleaves double-stranded DNA) or ribonuclease (a single-stranded RNA-cleaving enzyme), and thus nucleic acid fragments can be obtained. Fragmentation refers to degrading the biomolecule into fragments having lower molecular weights by using an appropriate degradation enzyme or physical or chemical treatment. Fragmentation can be performed by the above-described enzymatic treatment or chemical treatment. Persons skilled in the art can appropriately select enzymes, compounds, and the like to use herein and determine treatment conditions.

Figure 18:
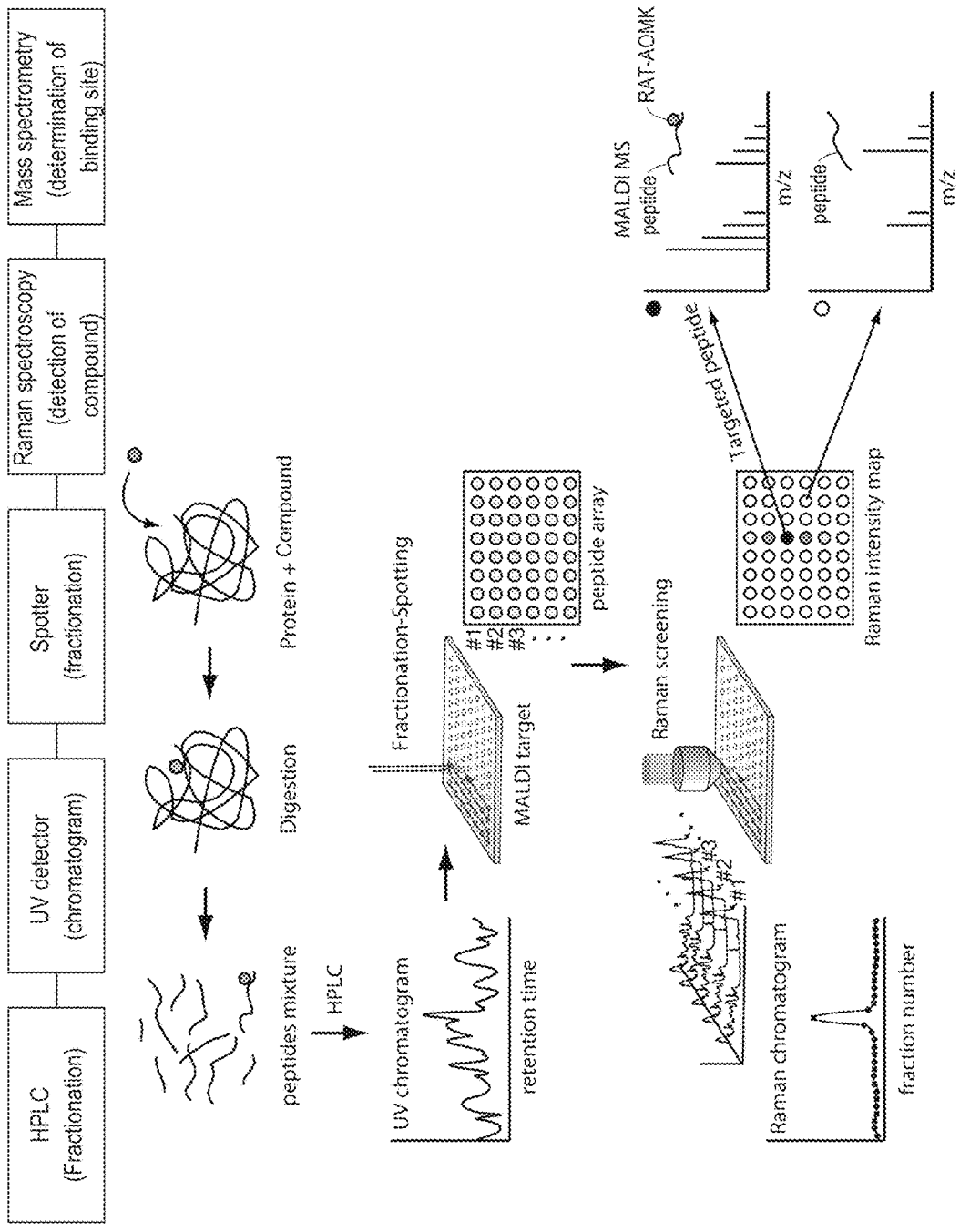
FIG. 18 shows the configuration of the apparatus according to the present invention.

3.2 Configuration for Identifying the Binding Site of a Biomolecule and a Low-Molecular-Weight Compound An example of an apparatus for identifying the binding site of a biomolecule and a low-molecular-weight compound is shown in FIG. 18. In the configuration of the apparatus, HPLC is connected to a UV detector, the UV detector is connected to a spotter, next, the spotter is connected the Raman spectroscopy unit, and then the unit is connected to the mass spectrometry unit. This apparatus can be used for the method for identifying the binding site of a biomolecule and a low-molecular-weight compound according to the present invention. This method is explained with reference to FIG. 18, as follows. First, a biomolecule (e.g., a protein) is bound to a low-molecular-weight compound. Next the biomolecule bound to the low-molecular-weight compound is fragmented (digested) with appropriate protease treatment. A mixture of the thus obtained fragments (peptides) is subjected to HPLC fractionation in the sample separation unit, and detection is performed with a UV detector, thereby obtaining a UV chromatogram. Next, each fraction is spotted onto a MALDI plate. The thus arranged peptide array is subjected to Raman spectroscopy, followed by mapping based on Raman intensities. Fractions exhibiting Raman signals are subjected to MALDI-MS to perform mass spectrometry, so that peptides with low-molecular-weight compounds bound thereto can be specified and thus the binding site of the low-molecular-weight compound and the biomolecule can be identified.

3.2.1 Analysis of the Binding of Cathepsin B and RAT8-AOMK

Figures 1, 19:
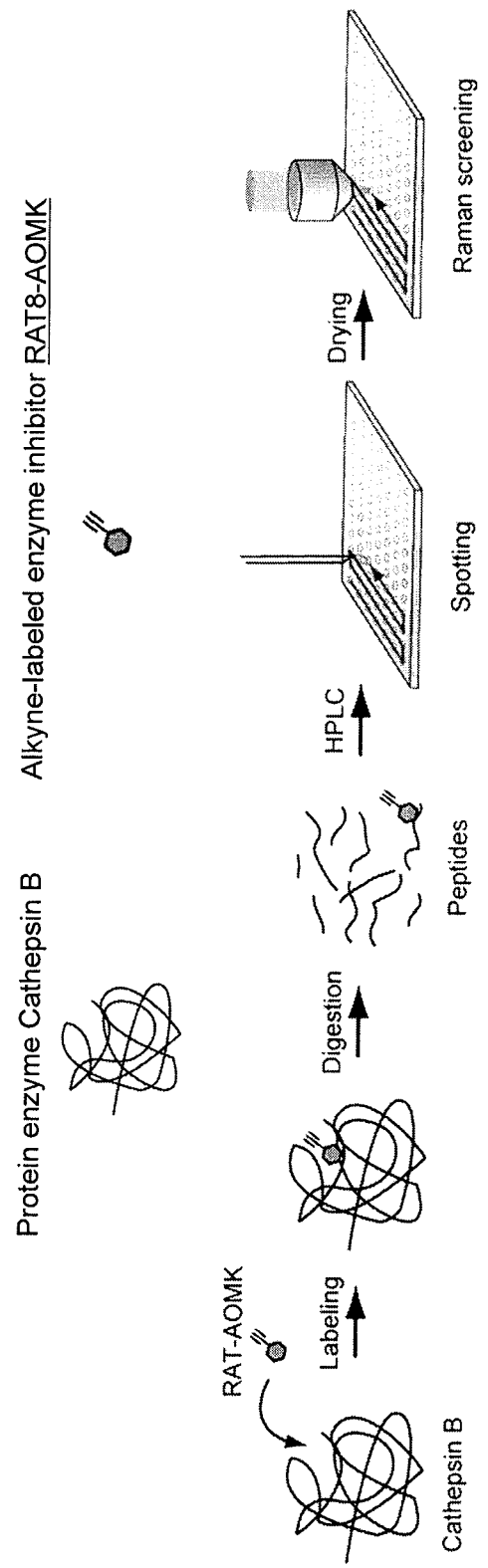
Figures 2, 19:
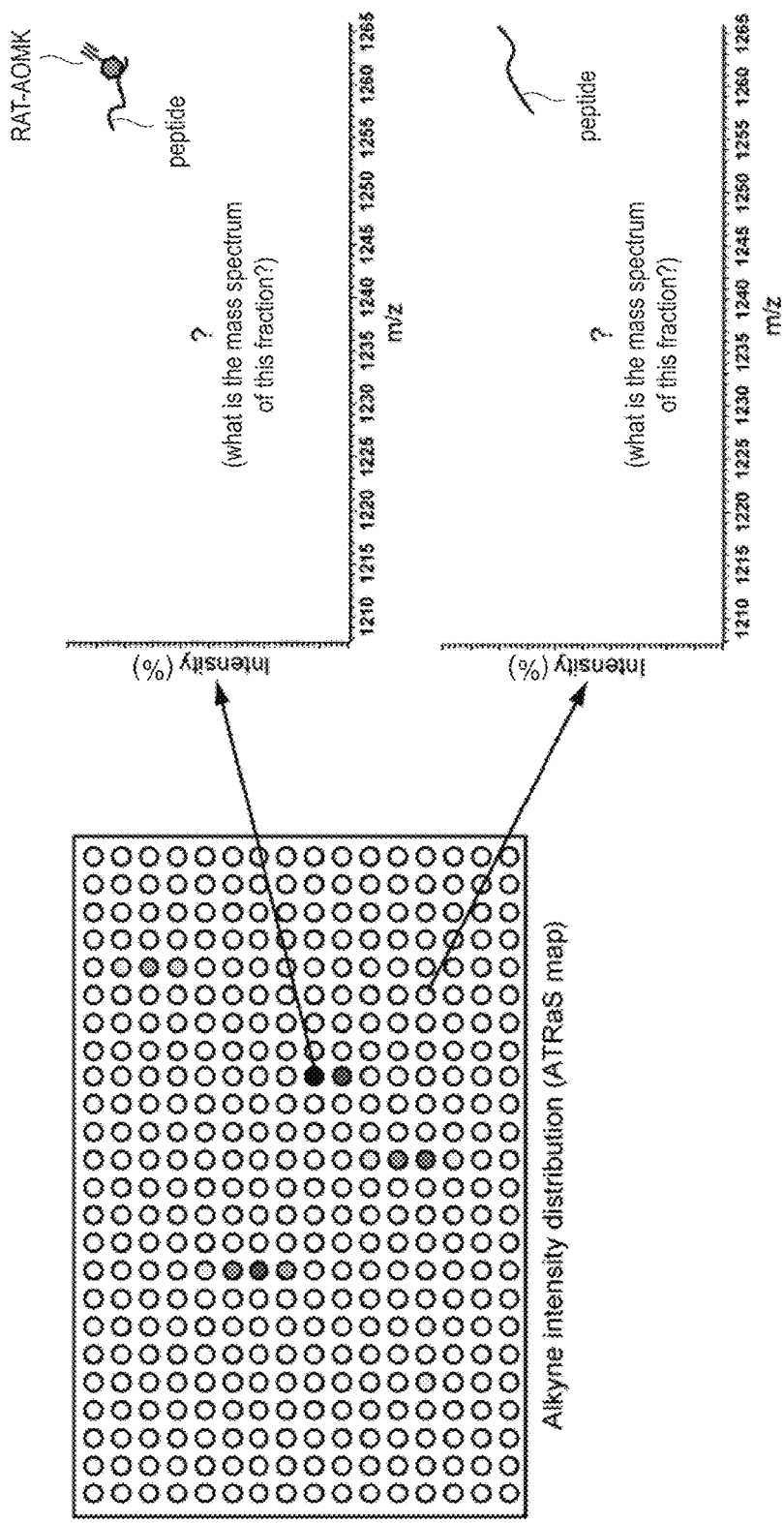

Identification of a binding site is explained as follows using a specific example. The present inventors have analyzed the binding site of the biomolecule cathepsin B, and a low-molecular-weight compound, RAT8-AOMK, using the method of 3. RAT8-AOMK is an alkyne-labeled cathepsin B inhibitor. FIG. 19-1 schematically shows in the upper section the procedures for the analysis of binding. As shown in the upper section of FIG. 19-1, first, RAT8-AOMK is bound to cathepsin B, and then this is fragmented (digested) by protease treatment. Through HPLC fractionation, fractions are spotted onto a plate, spots are dried, and then Raman spectroscopy is performed. FIG. 19-2 schematically shows on the left the distribution of alkyne intensities. Fractions with high intensities are subjected to mass spectrometry. The mass spectra of various peptides can be obtained by mass spectrometry. Through analysis thereof, peptide fragments with RAT8-AOMK bound thereto can be specified. Thus, the site(s) at which RAT8-AOMK is bound to cathepsin B can be identified.

Moreover, screening can also be performed with the Raman peak of the low-molecular-weight compound itself. Screening with the Raman peak of the low-molecular-weight compound itself can be performed by the apparatus or the method according to the present invention. Therefore, fractions containing the low-molecular-weight compound can be detected. Therefore, in addition to FIG. 18, the Description and Drawings illustrate a configuration in which the sample separation unit has a UV detector, for the sake of convenience. However, the UV detector of the sample separation unit is not essential for the apparatus or the method according to the present invention. A low-molecular-weight compound can also be detected by the Raman spectroscopy unit.

3.3 Comparing Mass Spectrometric Results with the Mass Information of Biomolecules In the present specification, obtaining mass spectrometric results, and "comparing" the results with the mass information of biomolecules, and then identifying the binding site(s) (within the biomolecule) of the low-molecular-weight compound refers to, with reference to a protein as an example, determining whether or not the obtained mass spectral results of peptide fragments are consistent with the calculated mass of a region corresponding to a portion of the protein from which the peptide is derived, thereby identifying the binding site in the protein, to which the low-molecular-weight compound binds. Persons skilled in the art can obtain the information concerning biomolecules such as proteins, peptides, nucleic acids, lipids and sugars, as necessary, from appropriate known databases including DDBJ/NIG, EMBL/EBI, GenBank/NCBI, NIAS DNA Bank, PIR, SWISS-PROT & TrEMBL, GenPept, PRF, Japan Consortium for Glycobiology and Glycotechnology DataBase (JCGGDB), and LipidBank. Moreover, whether or not amino acid sequences match can be determined using software such as Mascot (Matrix Science Inc.). Furthermore, the amino acid(s) bound to a low-molecular-weight compound can also be confirmed by MS/MS analysis.

4. Screening Method for Specifying a Biomolecule that Binds to a Low-Molecular-Weight Compound With the use of the apparatus according to the present invention, a biomolecule that binds to a low-molecular-weight compound can be specified. The screening method for specifying a biomolecule that binds to the low-molecular-weight compound, according to the present invention, comprises the following steps of:

(1) subjecting fractions containing a biomolecule bound to a low-molecular-weight compound to Raman spectroscopy, and then detecting fractions containing the biomolecule bound to the low-molecular-weight compound; and (2) subjecting all or some fractions subjected to Raman spectroscopy, to mass spectrometry.

This method comprises detecting by Raman spectroscopy fractions having a low-molecular-weight-compound-derived Raman peak, obtaining the mass spectrometric results of fractions having the low-molecular-weight-compound-derived Raman peak, comparing the results with the mass information of the biomolecule, and then specifying the biomolecule that binds to the low-molecular-weight compound.

As a step prior to step (1), for example, a low-molecular-weight compound is added to a mixture containing a target biomolecule, so as to bind the low-molecular-weight compound to the biomolecule, and then the resultant can be fractionated by a sample separation means. The thus separated fractions can be used in step (1).

4.1 Biomolecules

The screening method and the method for identifying binding sites according to the present invention can be used for various biomolecules including proteins, peptides, nucleic acids, sugars, and lipids.

4.1.1 Proteins

The screening method according to the present invention can be used for screening for a protein. For example, the method is performed to screen an organism or a virus, the nucleotide sequence of the entire genome of which has been decoded, for a protein in the organism or the virus, to which a low-molecular-weight compound having drug activity binds and exhibits its effect. As a result, the mass spectrometric result of the protein that binds to the low-molecular-weight compound can be obtained. Furthermore, a protein that binds to the low-molecular-weight compound is digested by protease treatment, fragmented into peptides, and then subjected to mass spectrometry, so that the mass information of the peptide fragments can be obtained. Furthermore, the peptide fragments are subjected to MS/MS analysis, and thus the amino acid sequences of the peptides can be determined. The thus obtained amino acid sequences are compared with the sequence information of all proteins coded in the decoded full genome sequence, and then a protein that binds to the low-molecular-weight compound can be specified. This similarly applies to peptides. Moreover, with the use of the above "3. Method for identifying the binding site of a biomolecule and a low-molecular-weight compound", the binding site can also be identified. This similarly applies to other biomolecules, such as nucleic acids, sugars, or lipids. When exhaustive mass information of various nucleic acids, sugars, or lipids contained in a sample is available, the above method according to the present invention can be performed and as a result, the mass spectrometric results of a nucleic acid, a sugar, or a lipid that binds to a low-molecular-weight compound can be obtained, and the results can be compared with the above exhaustive mass information, and thus a nucleic acid, a sugar, or a lipid that binds to the low-molecular-weight compound can be specified. This is explained as follows.

4.1.2. Nucleic Acids

The method according to the present invention can also be used for nucleic acids. For example, when the information of various nucleic acid molecules of a type of cells is available, the method according to the present invention is performed to determine a nucleic acid molecule to be bound to a low-molecular-weight compound. Thus, the mass information of such nucleic acid molecule that binds to the low-molecular-weight compound can be obtained. Moreover, MS/MS analysis can be performed, so that the mass spectra of nucleic acids that are degraded sequentially can also be obtained. The results can be compared with the above mass information, so that the nucleic acid molecule to be bound to the low-molecular-weight compound can be specified. In addition, after specification of the bound nucleic acid, the method according to the present invention can be performed, so that the binding site can also be determined.

4.1.3 Sugars

The method according to the present invention can also be used for sugars. For example, when the structures of a plurality of capsular polysaccharides of a pathogenic bacterium have been elucidated and when it is ought to determine which capsular polysaccharide a given low molecular weight compound binds, the method according to the present invention can be performed to determine the capsular polysaccharide which the low-molecular-weight compound binds and as a result, the mass information of the capsular polysaccharide that binds to the low-molecular-weight compound can be obtained. Moreover, MS/MS analysis can be performed, so that the mass spectra of polysaccharides that are degraded sequentially can also be obtained. The results are compared with the above mass information, so that the capsular polysaccharide to be bound to the low-molecular-weight compound can be specified. In addition, after specifying the bound capsular polysaccharide, the method according to the present invention can be performed to determine the binding site as well.

4.1.4 Lipids

The method according to the present invention can also be used for lipids. For example, when the exhaustive information concerning molecules composing a cellular lipid bilayer membrane is available, the method according to the present invention can be performed to determine a lipid molecule to be bound to a low-molecular-weight compound and as a result, the mass spectrum of a lipid molecule that binds to the low-molecular-weight compound can be obtained. The result can be compared with the exhaustive information concerning the above lipid, and thus the lipid molecule which binds to the low-molecular-weight compound can be specified. In addition, after specifying the bound lipid molecule, the method according to the present invention can be performed to determine the binding site as well.

Figure 32:
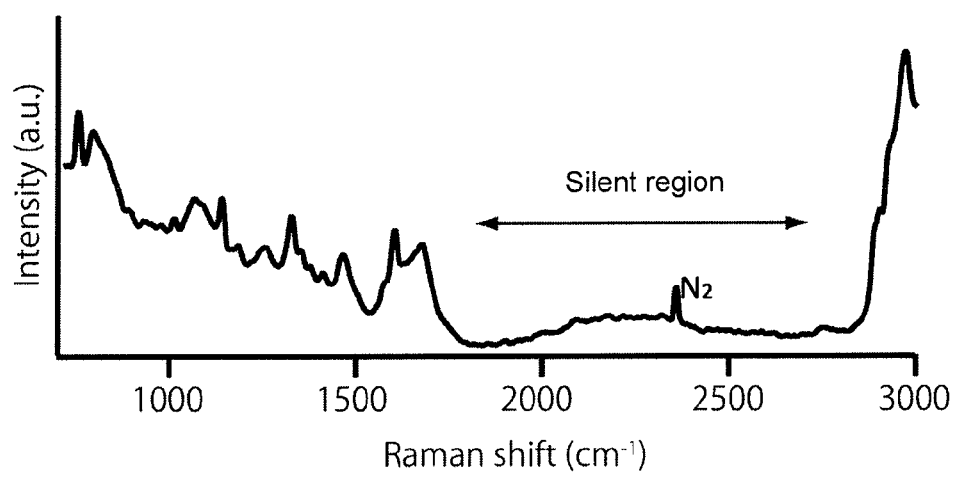
FIG. 32 shows the Raman spectrum of HeLa cells. A silent region was observed at 1800-2800 cm$^{-1}$ Excitation wavelength used herein was 532 nm.

In the present specification, a system using RAT8-AOMK as the low-molecular-weight compound and the protein cathepsin B as the biomolecule is described as a typical example. However, biomolecules, to which the apparatus and the method according to the present invention can be applied, are not limited to proteins, in principle. This is because other cellular components, nucleic acids, sugars, and lipids basically have the same silent region. Therefore, with the use of an appropriate Raman label for a low-molecular-weight compound, in principle, a nucleic acid, a sugar, or a lipid bound to a low-molecular-weight compound can be distinguished by Raman spectroscopy from a mixture of nucleic acids, sugars, and lipids having the silent region. Here, the Raman spectrum of HeLa cells is shown in FIG. 32. No Raman peak is particularly observed in a region of 1800-2800 $cm^{-1}$, and the range of the silent region is the same as that of the cell disruption solution, as shown in FIG. 32. See Non-patent Document 1.

This is more specifically explained as follows. Almost no carbon-carbon triple bond is present in vivo and, therefore, the Raman peak of alkyne, which appears in the silent region, can be detected for any measurement object(s), as long as the sample is derived from a living body. Therefore, the apparatus and the method according to the present invention can also be applied to a biomolecule such as a nucleic acid, a sugar, and a lipid using a group that has a peak in the silent region, such as that of alkyne, as a Raman label.

4.2 Preparation of a Biomolecule Bound to a Low-Molecular-Weight Compound to be Analyzed A solution containing a biomolecule bound to a low-molecular-weight compound can be prepared by causing cells to incorporate the low-molecular-weight compound to bind to the biomolecule within cells, and then disrupting the cells. Moreover, a solution containing a biomolecule bound to a low-molecular-weight compound can also be prepared by disrupting cells, then adding the low-molecular-weight compound to the cell disruption solution for the compound to bind to the biomolecule within cells.

4.3 Fractionation Using Liquid Chromatography

A sample to use for the method according to the present invention may be prepared by fractionation via liquid chromatography using a low-boiling-point polar solvent and water as separation solvents. The low-boiling-point polar solvent is as described in 1.1.1.

4.4 Preparation of Spots Using a Plate and Spotting Effects

Figure 13:
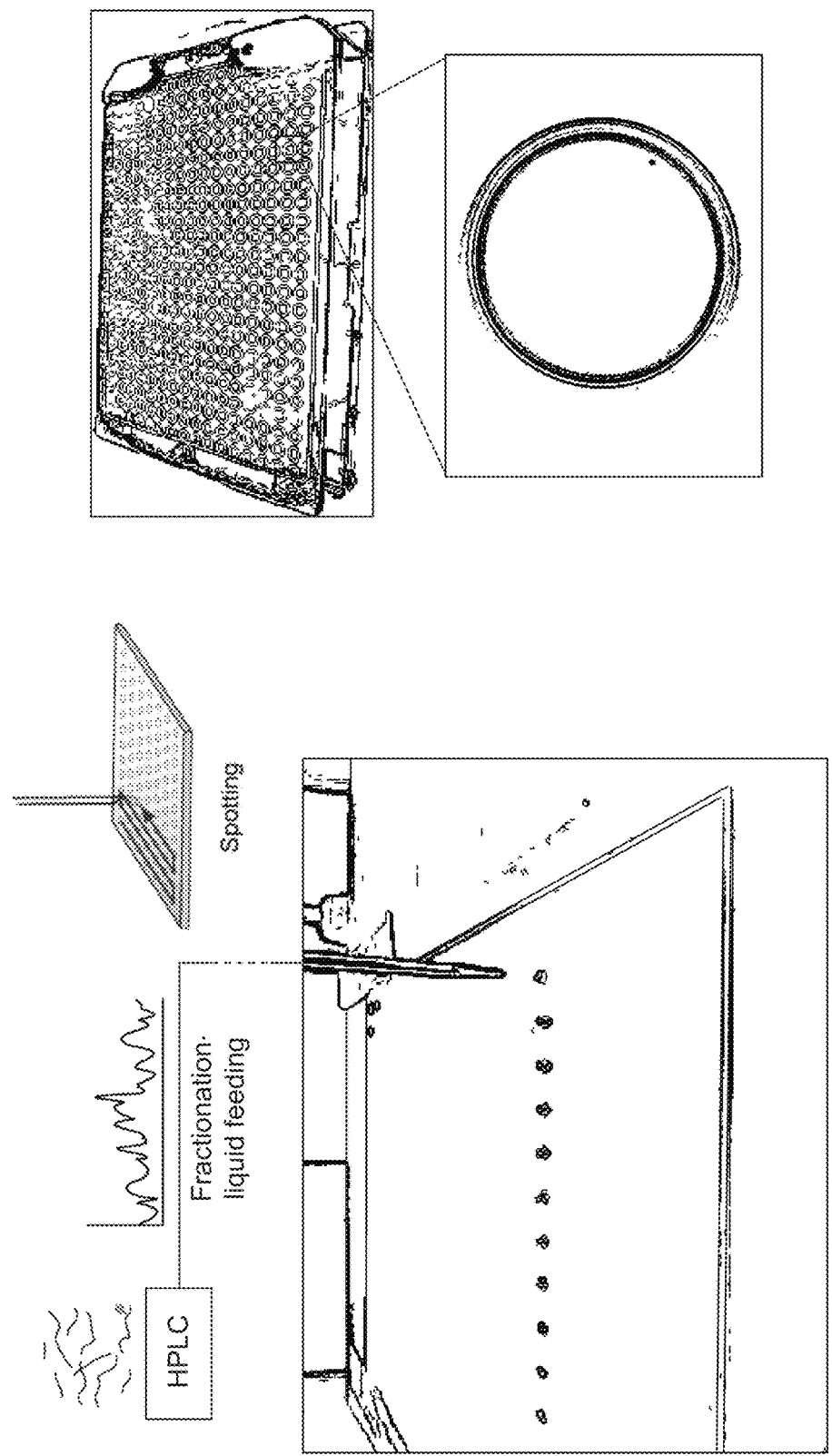
FIG. 13 shows a multi-spotted metal substrate and spotted samples. A fractionated sample is spotted as in a schematic diagram in the center on top. The upper right section shows a 384 multi-spotted metal substrate. The lower right section is a photograph showing how peptides in solution were aggregated as droplets on the substrate dried.

Regarding the method according to the present invention, spots to be subjected to Raman spectroscopy can be prepared by preparing fractions to be subjected to Raman spectroscopy directly in the form of droplets or droplets of the fraction mixed with a solvent, arranging the droplets onto an appropriate plate, and then vaporizing the solvent contained in the droplets. Since spots are prepared by vaporizing a solvent and Raman spectroscopy is performed with a Raman microscope, a plate to be used herein preferably has a cleaned surface. The term "cleaned surface of a plate" means that liquid, solid contaminants, inorganic and organic impurities, fingerprints, dust, cloudiness, and scratches, which can inhibit Raman spectroscopy, are not present on the surface. Cleaning can be performed by washing the plate surface with water, an aqueous cleaning agent containing a surfactant, or an organic solvent, and then drying the plate. In addition, the plate to use herein preferably has a water repellent surface. The water-repellent surface of the plate is further preferably cleaned in advance. The term "water repellent" refers to repelling water. The term "water-repellent surface of a plate" refers to a surface that repels water on the plate. Such water-repellent surface can be achieved by coating a plate with a water repellent having surface tension significantly lower than that of water, such as a fluorine-based water repellent or a silicone-based water repellent. A plate having a water-repellent surface may be a plate made of metal, glass, quartz, calcium fluoride, or magnesium fluoride, and preferably has no or almost no effects on the results of Raman spectroscopy and mass spectrometry. Droplets can be arranged on a plate using a micropipette. This operation can be performed manually or using an automated device. Examples of such plate include, but are not limited to, a 96-well plate and a 384-well plate that are broadly used in the technical field. An example of spotting a fractionated sample onto a plate is shown in FIG. 13. As shown on the left in FIG. 13, a solution fractionated by HPLC is fed, and then spotted onto a plate. The order of spotting is merely an example. As shown in the lower right section of FIG. 13, peptides in solution are aggregated in the form of rings, as droplets on the substrate are dried. The ring portions are analyzed using a Raman microscope, so that a Raman spectrum can be efficiently obtained with high sensitivity.

4.4.1 Plate for Raman Microscope

Figure 14:
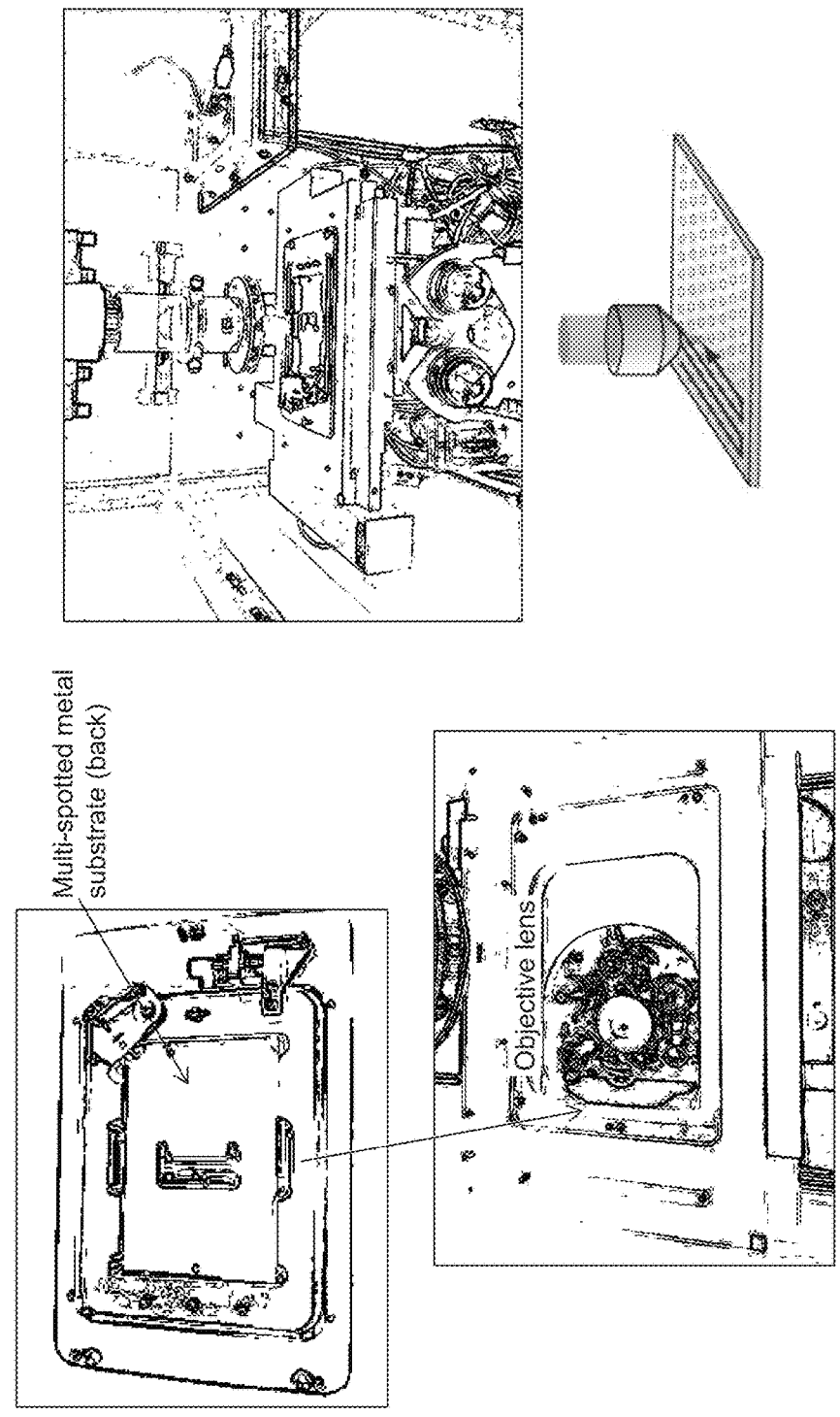
FIG. 14 shows examples of plates that can be used for the apparatus according to the present invention. The upper left section shows a plate for fixing a substrate for a microscope. The lower left section shows a stage for a Raman microscopic sample. Raman screening is performed as in the schematic diagram shown in the lower right section.
Figures 1, 15:
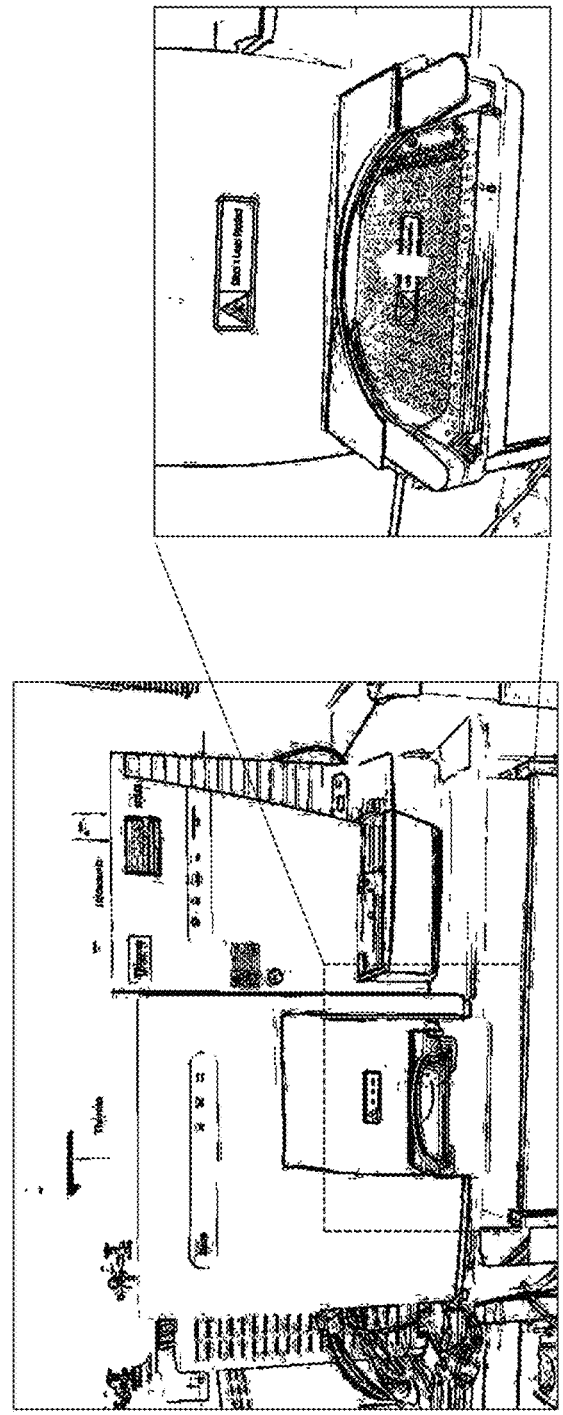
Figures 2, 15:
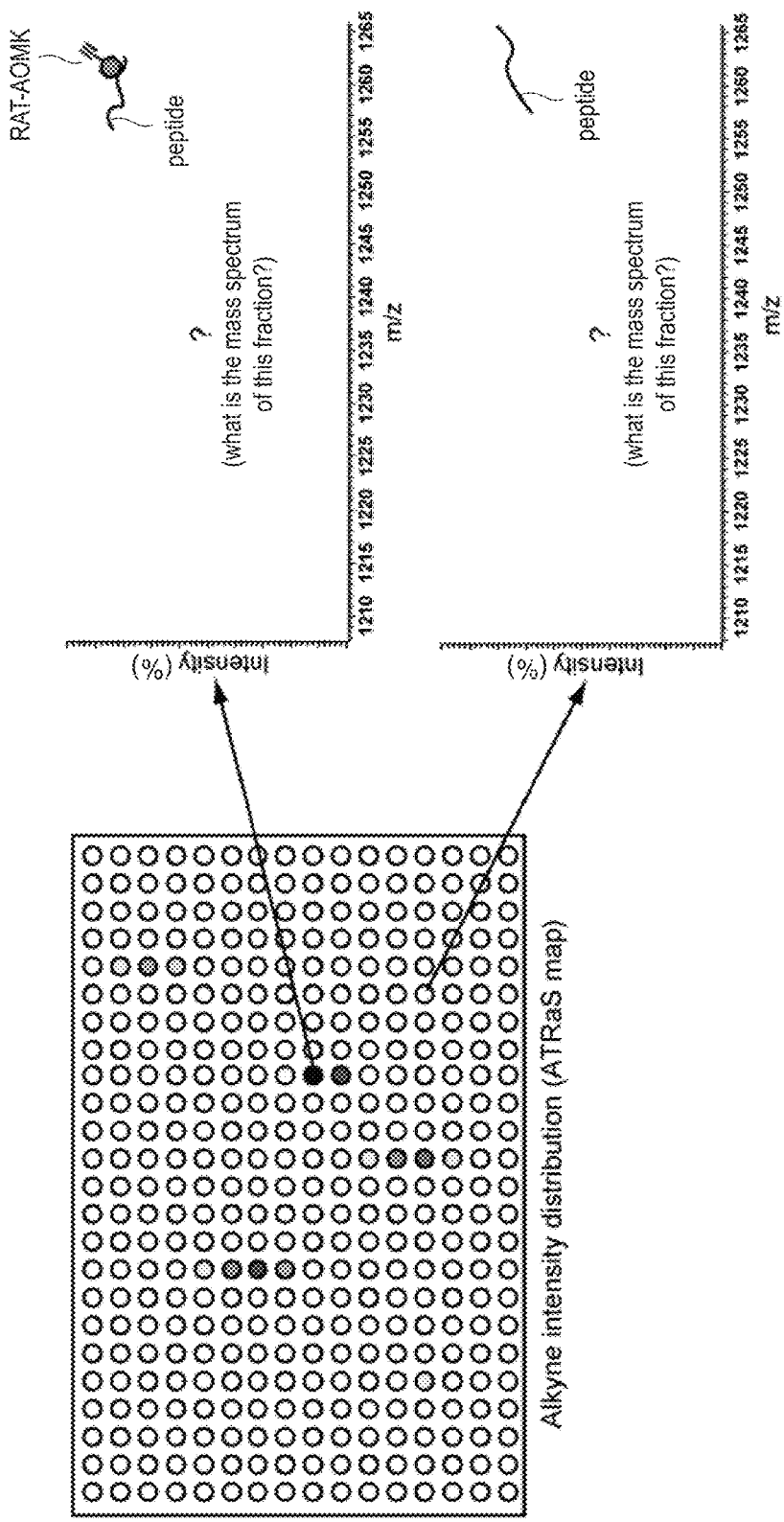

Raman spectroscopy and mass spectrometry can be performed using a commercially available plate. A plate for fixing a substrate for a microscope, which is suitable for a sample stage of a Raman microscope, may be prepared and can be used herein. FIG. 14 and FIG. 15-1 show examples of a plate that can be used for the apparatus according to the present invention. The upper left section of FIG. 14 shows a plate for fixing a substrate for a microscope. A photograph is a multi-spotted metal substrate viewed from the back. The lower left section of FIG. 14 shows a sample stand of the Raman microscope. The photograph on the right in FIG. 14 shows the plate for fixing a substrate for a microscope, which is placed on the sample stand. Raman spectroscopy is performed under the state. Detecting spots having a target Raman peak is also referred to as Raman screening.

Figure 17:
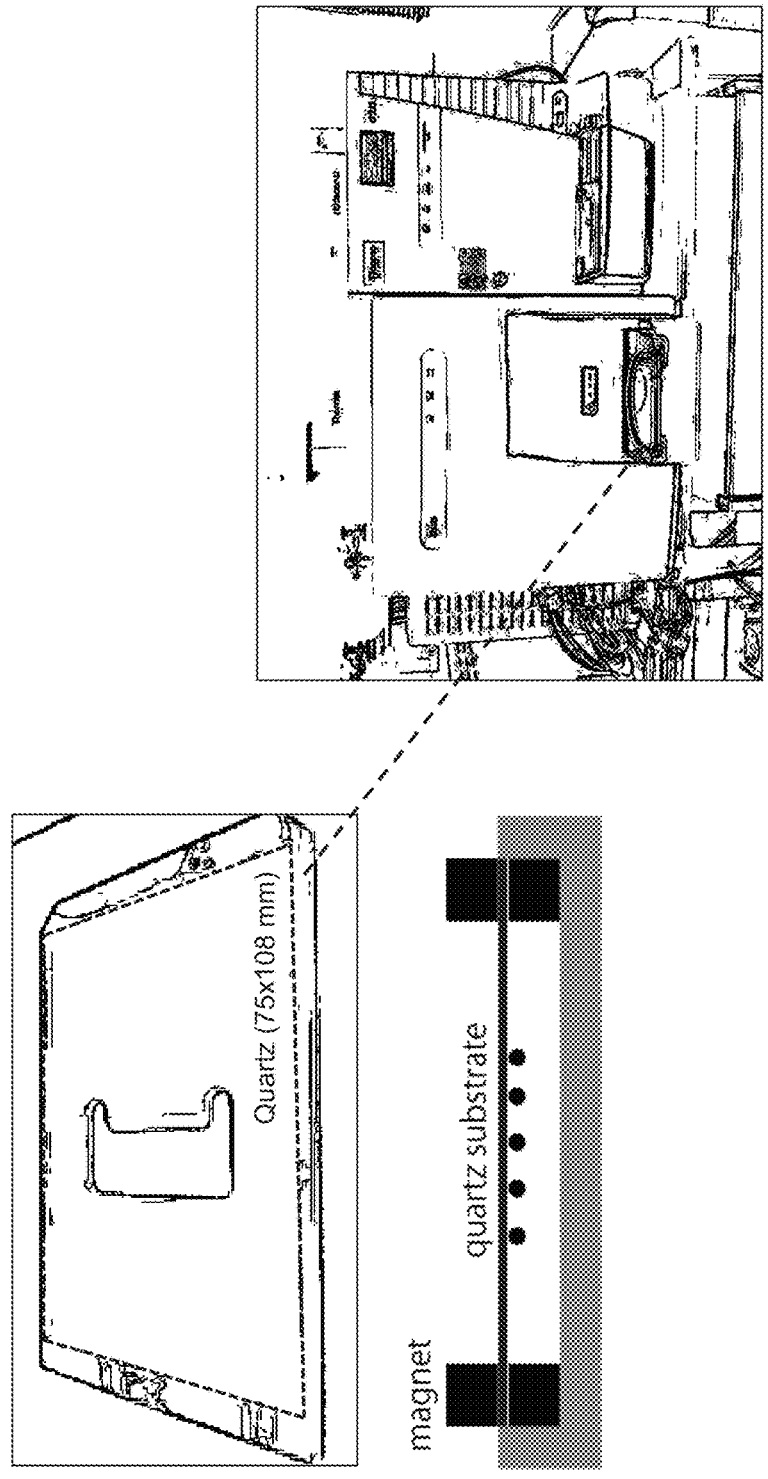
FIG. 17 shows a multi-spotted substrate with all surfaces made of quartz. This can enhance the sensitivity of Raman measurement and enables the direct use of a sample for MALDI-MSI measurement. Quartz is fixed using a magnet.

In the apparatus and the method according to the present invention, fractions of a sample subjected to Raman spectroscopy are then subjected to mass spectrometry. Therefore, the plate used for Raman spectroscopy can be preferably directly used for analysis with a mass spectrometer. Therefore, the present inventors have developed a plate with which Raman spectroscopy and mass spectrometry can be smoothly performed for a spotted sample. An example thereof is shown in FIG. 15-1 to FIG. 17. With the use of this plate, a sample screened by the Raman spectroscopy unit can be directly analyzed in the mass spectrometry unit. In FIG. 16, it was confirmed that a quartz substrate that is advantageous for Raman measurement can be directly used for MALDI-MS measurement. FIG. 16 shows on the left that the left spot is alkyne peptide 1 and the right spot is peptide 1. FIG. 16 shows in the lower left section that the left arrow indicates the spot of the alkyne peptide, and the right arrow indicates the spot of peptide 1. FIG. 16 shows in the upper right section the Raman spectra of alkyne peptide 1 and peptide 1. Both samples can be distinguished from each other on the basis of the presence or the absence of a Raman peak at 2123 cm$^{-1}$. Furthermore, FIG. 16 shows in the lower right section the results of MALDI-MS measurement, wherein a mass difference between alkyne peptide 1 and unlabeled peptide 1 can be confirmed based on the spectra, as being consistent well with a calculated value. The results correspond to FIG. 6 and FIG. 7. As in the mass spectra shown in FIG. 7 and in the lower right section of FIG. 16, it was confirmed that the same sample subjected to Raman spectroscopy can be directly analyzed by a MALDI method. FIG. 17 shows a multi-spotted substrate having all surfaces made of quartz. The substrate is treated with hydrochloric acid, sulfuric acid, nitric acid, or the like, washed with water to remove acid, washed with a low-boiling-point solvent such as acetone, and then dried. The substrate is required to have a clean surface, and is further preferably water-repellent, so that biological matter can be aggregated with high density. Therefore, the substrate can be produced by performing water repellent finishing using a silicone-based water repellent such as dimethyldichlorosilane and trimethylchlorosilane, a fluorine-based water repellent, or the like, for which no signals are observed in the silent region of the Raman spectra. The substrate is fixed on a base using a magnet, as shown in the lower left section of FIG. 17. This plate can also be used for the method and the apparatus according to the present invention.

5. Use of the Present Invention

The present invention is characterized by fractionating a sample using a liquid chromatographic or a capillary electrophoretic device in the sample separation unit, and then directly using the fractionated sample for the Raman spectroscopy unit, which has not been achieved by conventional techniques. Therefore, a specific biomolecule or fragment can readily be detected or separated and then specified. Furthermore, the Raman spectroscopy unit is connected to the mass spectrometry unit, and thus fractions specified by Raman spectroscopy can be directly analyzed by a mass spectrometer immediately following Raman spectroscopy. Therefore, sequencing of biomolecules and identifying the binding site with a low-molecular-weight compound can be conveniently performed. The term "sequencing" refers to the determination of an amino acid sequence when the biomolecule is a protein or a peptide, and the determination of the sequence of a sugar composting a polysaccharide, when the biomolecule is a polysaccharide, for example.

The apparatus and the method according to the present invention can also be used for analyzing the post-translational modification of a protein. For example, when a protein is modified at a specific site (for example, in the case of a palmitoyl group, a cysteine residue) with a lipid such as a farnesyl group or a palmitoyl group after protein translation, the lipid is Raman-labeled and used as the low-molecular-weight compound according to the present invention, and then the compound is used for the apparatus and the method according to the present invention. As a result, a protein that binds to the Raman-labeled lipid can be specified, and the binding site can also be identified. Such Raman-labeled lipid may be incorporated into cells for the lipid to bind to a target protein, or may be added to a cell disruption solution to bind to a target protein. Conventional methods are problematic in that when a lipid is modified with a fluorophore, the cellular mechanism of the post-translational modification of a protein cannot recognize the fluorescently modified lipid, and the subsequent analysis cannot be performed. An example of an improved method thereof, which involves causing cells to incorporate a lipid, modifying the lipid with a fluorophore using a click reaction, and specifying a protein that binds to the lipid by fluorescence analysis (Non-patent Document 4) and an example of an improved method thereof, which involves introducing a biotin tag into a lipid using a click reaction, and then detecting with streptavidin (Non-patent Document 5), have been reported. However, these methods are problematic in complicated handling, nonspecific reaction, and the loss of a target protein due to reaction operation. In contrast, with the use of the apparatus or the method according to the present invention, a biomolecule that binds to the Raman-labeled lipid having no or almost no effect on the cellular mechanism of the post-translational modification of a protein can be specified, and the binding site can be identified. This similarly applies to a case wherein the post-translational modification of a protein is performed with a sugar.

6. Advantageous Effects of the Present Invention

Taken together, the apparatus and the method according to the present invention make it possible to exhaustively searching biomolecules and specify a biomolecule that binds to a low-molecular-weight compound, or to identify the binding site of a biomolecule and a low-molecular-weight compound. According to the present invention, a low-molecular-weight compound can be selectively detected with high sensitivity using the Raman peak of the compound itself or a Raman label having a characteristic Raman peak, such as an alkynyl group.

In the case of the method according to the present invention, a low-molecular-weight compound can be directly used, or the molecular weight of the tag attached to an analyte compound can be kept low. Therefore, unlike conventional fluorescent labeling methods using large-molecular-weight fluorophores, the target biomolecule can be specifically distinguished from other substances, detected, and specified by the method of the present invention without altering the biochemical properties of a low-molecular-weight compound. Furthermore, molecular vibration information derived from not only the low-molecular-weight compound, but also the biomolecule can be obtained by the Raman spectroscopy according to the present invention. Thus, the present invention has an advantage that co-existence of a low-molecular-weight compound and a biomolecule can be confirmed, which has not been achieved by conventional techniques.

Furthermore, a conventional method that uses a combination of an alkyne tag and a click reaction (e.g., Non-patent Document 2) is problematic in that the target substance is lost due to operation(s) of click reaction, and that a nonspecific reaction may occur, for example. In contrast, in the case of the method according to the present invention, the alkyne tag itself can be analyzed by the Raman spectroscopy method. Therefore, problems including loss of the target substance, non-specific reaction, and the like of conventional methods are addressed by the present invention.

Furthermore, the SERS method using the aggregation-accelerating agent of the present invention is characterized in that measurement sensitivity is increased and the detection limit is improved. Moreover, in the case of the SERS method using the aggregation-accelerating agent of the present invention, the distribution of aggregates are homogenized. Therefore, correlation between the amount of a sample to be measured and SERS signals is improved, variation of measurement results is reduced, long-term measurement, which is a weak point of Raman measurement, can be shortened.

EXAMPLES

The following examples are only intend to illustrate the present invention, and do not limit the technical scope of the present invention.

Materials and methods are explained. Other materials and reagents are commercially available, or obtained or prepared according to common techniques in the technical field or procedures in known documents, unless otherwise specified.

Materials

Trifluoroacetic acid (TFA) for separation of samples by liquid chromatography was obtained from Wako Pure Chemical Industries, Ltd., and 0.1% formic acid-containing distilled water and 0.1% formic acid (FA)-containing acetonitrile (MeCN) were obtained from Kanto Chemical Co., Inc. In addition, acetonitrile and distilled water for semi-micro HPLC were obtained from NACALAI TESQUE, INC.

Experimental Techniques

<Liquid Chromatography>

An example of liquid chromatography is as follows. A sample was prepared, injected into HPLC (Ultimate3000, DIONEX) provided with a UV detector, and then fractionated using a fraction collector (Probot, DIONEX). The flow rate was 50 µl/minute. A 0.1% TFA-containing distilled water-acetonitrile mixed solvent was used as the separation solvent and an acetonitrile concentration gradient was applied, where necessary.

<Raman Spectroscopy>

An example of measurement conditions is as follows, wavelength: 532 nm, laser intensity: 30 mW, exposure time: 30 seconds, objective magnification: ×40, numerical aperture: 0.75, and irradiation in dry air: point irradiation. The laser was focused on ring regions (in a dry, aggregated, and powdery state) in which peptides were concentrated to a high degree. Spectra were obtained repeatedly 5 times for each spot and then averaged to obtain one spectrum.

<MALDI-Orbitrap>

MALDI mass spectra were obtained using a LTQ Orbitrap XL (Thermo Fisher Scientific) provided with a MALDI ion source. A sample was mixed with α-cyano-4-hydroxycinnamic acid (CHCA) or 2,5-dihydroxybenzoic acid (DHB) (Bruker). MALDI mass spectra were obtained using FT mode (resolution: 30,000 or 60,000). These spectra were obtained manually. Parameters used herein are as follows: scan range: m/z 800-4000, laser energy (µJ): 2-4 (for CHCA) or 6-8 (for DHB).

<Nano Flow HPLC-Electrospray-Ionization Mass Spectrometry (Nano LC-MS)>

LC-MS was performed with the following procedures for comparison with LC-R-MS according to the present invention. Nano LC-MS and MS/MS were obtained using LTQ Orbitrap XL (Thermo Fisher Scientific) provided with an ESI ion source. A nano HPLC system (Ultimate 3000, DIONEX), a trap column (ZORBAX 300SB C18 (inside diameter: 0.3×5 mm), Agilent) and a tip column (NTCC-360, inside diameter 0.075 mm, Nikkyo Technos Co., Ltd.) were used. Mobile phase A was distilled water containing 0.1% formic acid and 4% acetonitrile, mobile phase B was acetonitrile containing 0.1% formic acid. A sample was diluted with 0.1% TFA or n-decyl-β-D-glucopyranoside (DG) (MP Biomedicals) with an appropriate concentration, and then eluted by a gradient method at a flow rate of 200 nL/minutes using 0-80% mobile phase B/30 minutes. ESI mass spectra were obtained using FT mode (resolution 60,000) and MS/MS spectra were obtained using ion trap mode.

Database search for identifying proteins or modified peptides was performed using a peptide sequencing program (Protein Discoverer, Thermo Fisher Scientific) and a database MS/MS Ion Search (mascot search engine (Matrix-Science)).

Example 1

Raman Spectroscopy of Low-Molecular-Weight Compounds Having Raman Labels

Low-molecular-weight peptides having the amino acid sequence of EQWPQCPTXK (SEQ ID NO: 4), and specifically a peptide in which X is isoleucine and a peptide in which X is propargyl glycine, were synthesized. Hereinafter, the former is referred to as peptide 1, and the latter is referred to as alkyne peptide 1 in this example. Peptide 1 was synthesized by the solid phase synthesis (Fmoc) method. Similarly, alkyne peptide 1 was also synthesized by the solid phase synthesis method (all peptides were synthesized at the RIKEN Brain Science Institute). A commercially available product was used for propargyl glycine. These structures are shown in the upper section of FIG. 6.

Figures 2, 8:
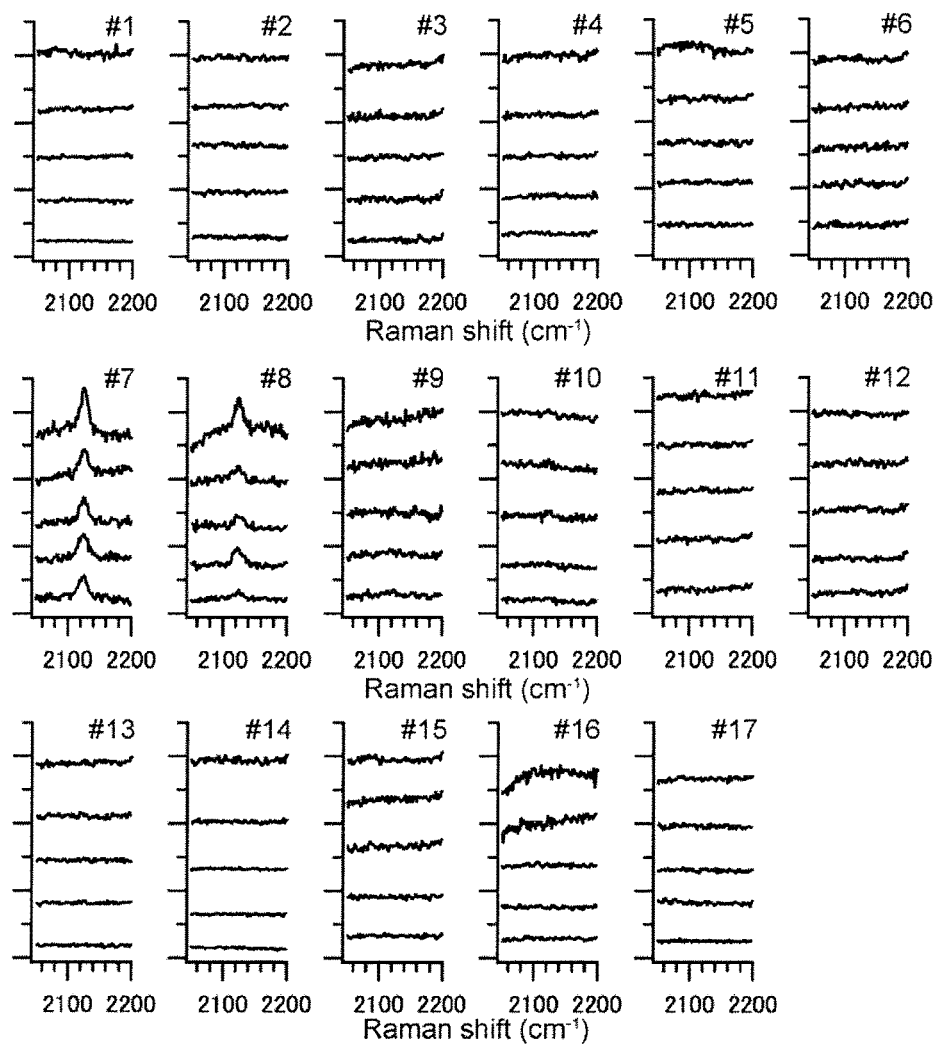

Alkyne peptide 1 was fractionated by liquid chromatography, and then subjected to Raman spectroscopy. The results are shown in FIG. 8-1 and FIG. 8-2. Liquid chromatography and Raman spectroscopy were performed by/under techniques and conditions described in "Experimental techniques" above. First, samples were fractionated by liquid chromatography depending on retention times. Fractions were measured using a UV detector and the results are shown in FIG. 8-1A. As shown in an enlarged view of the results, FIG. 8-1B, a UV peak was observed between 28 minutes and 29 minutes, and thus a peptide was detected. FIG. 8-2D shows the Raman spectra of fraction Nos. 1-17. The Raman peak characteristic of alkyne was observed for fraction Nos. 7 and 8. As described above, the results of UV spectral analysis were consistent with the same of Raman spectroscopy, demonstrating that an alkyne-labeled peptide can be detected by Raman spectroscopy.

Next, the results of performing Raman spectroscopy individually for peptide 1 and alkyne peptide 1, and superimposed spectra results are shown in the lower section of FIG. 6. Experimental conditions were as described in "Experimental techniques above. Samples were in the form of powders. As shown in the lower section of FIG. 6, while a Raman peak specific to alkyne was observed at 2123 $cm^{-1}$ in the case of the spectrum (1) of alkyne peptide 1, no Raman peak was observed in this region in the case of the spectrum (2) of unlabeled peptide 1. As described above, the Raman spectrum of peptide 1 could be clearly distinguished from that of alkyne peptide 1.

Figure 7:
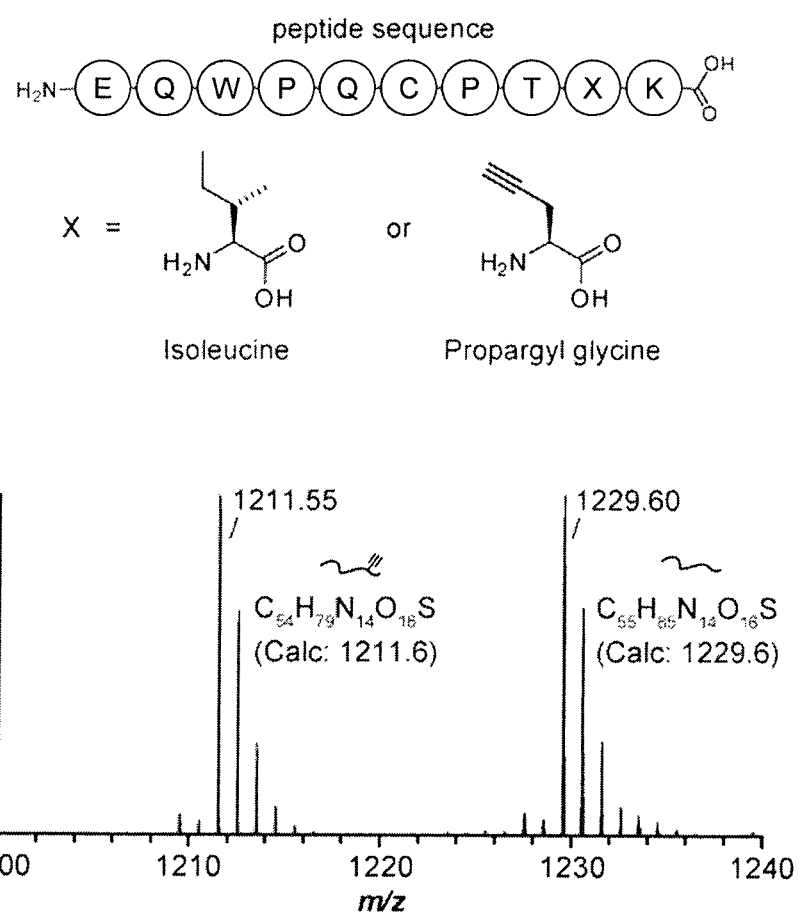
FIG. 7 shows the mass spectra of an alkyne-labeled peptide and a unlabeled peptide.

Next, it was confirmed that the samples of the above peptide 1 and alkyne peptide 1 subjected to Raman spectroscopy can be directly analyzed by mass spectrometry. Experimental conditions were as described in "Experimental techniques" above. Mass spectrometric results of samples subjected to Raman spectroscopy are shown in FIG. 7. The peak of alkyne peptide 1 was detected in the vicinity of m/z 1211, and the peak of peptide 1 was detected in the vicinity of m/z 1229.

Figures 1, 9:
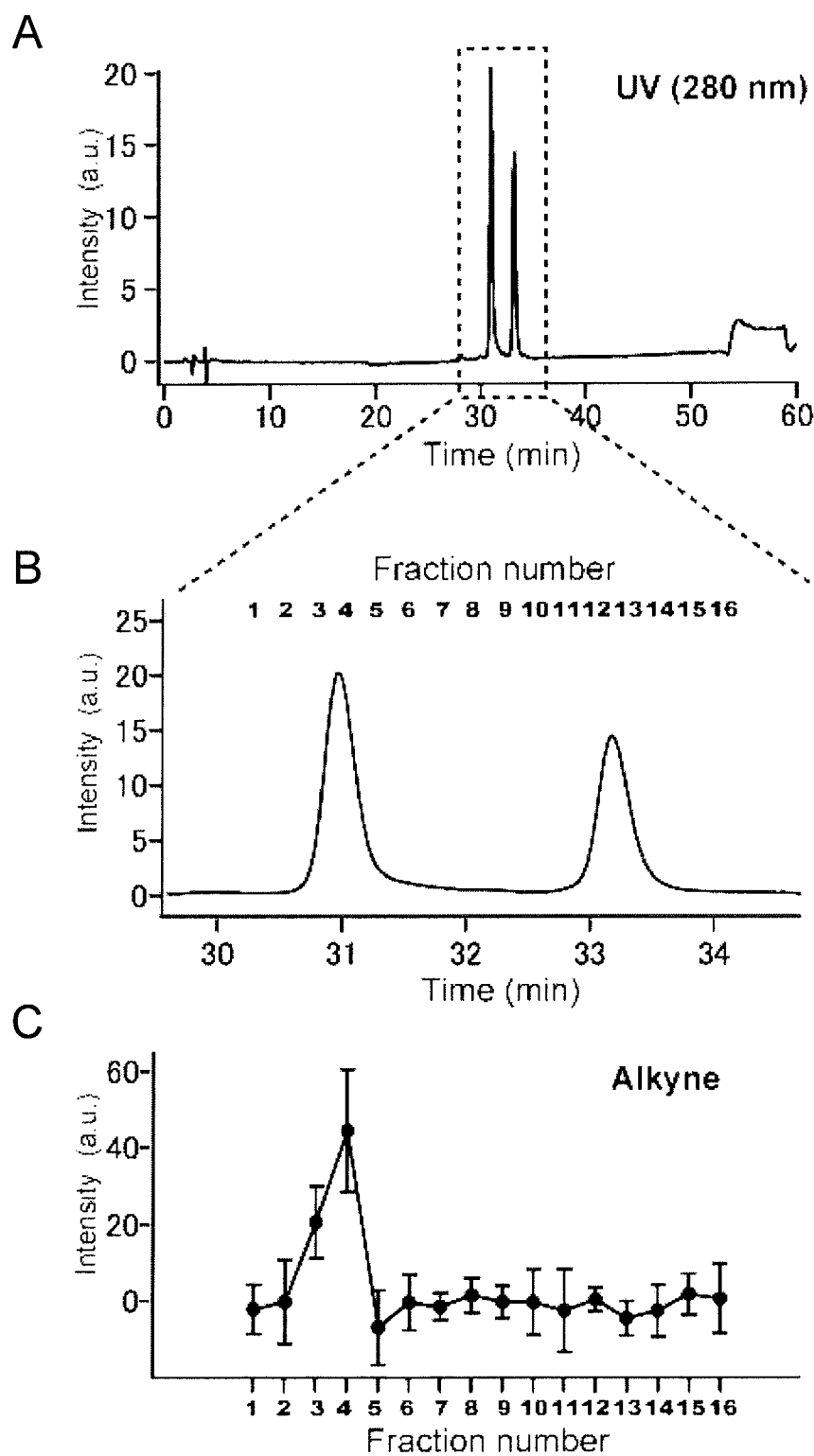
Figures 2, 9:
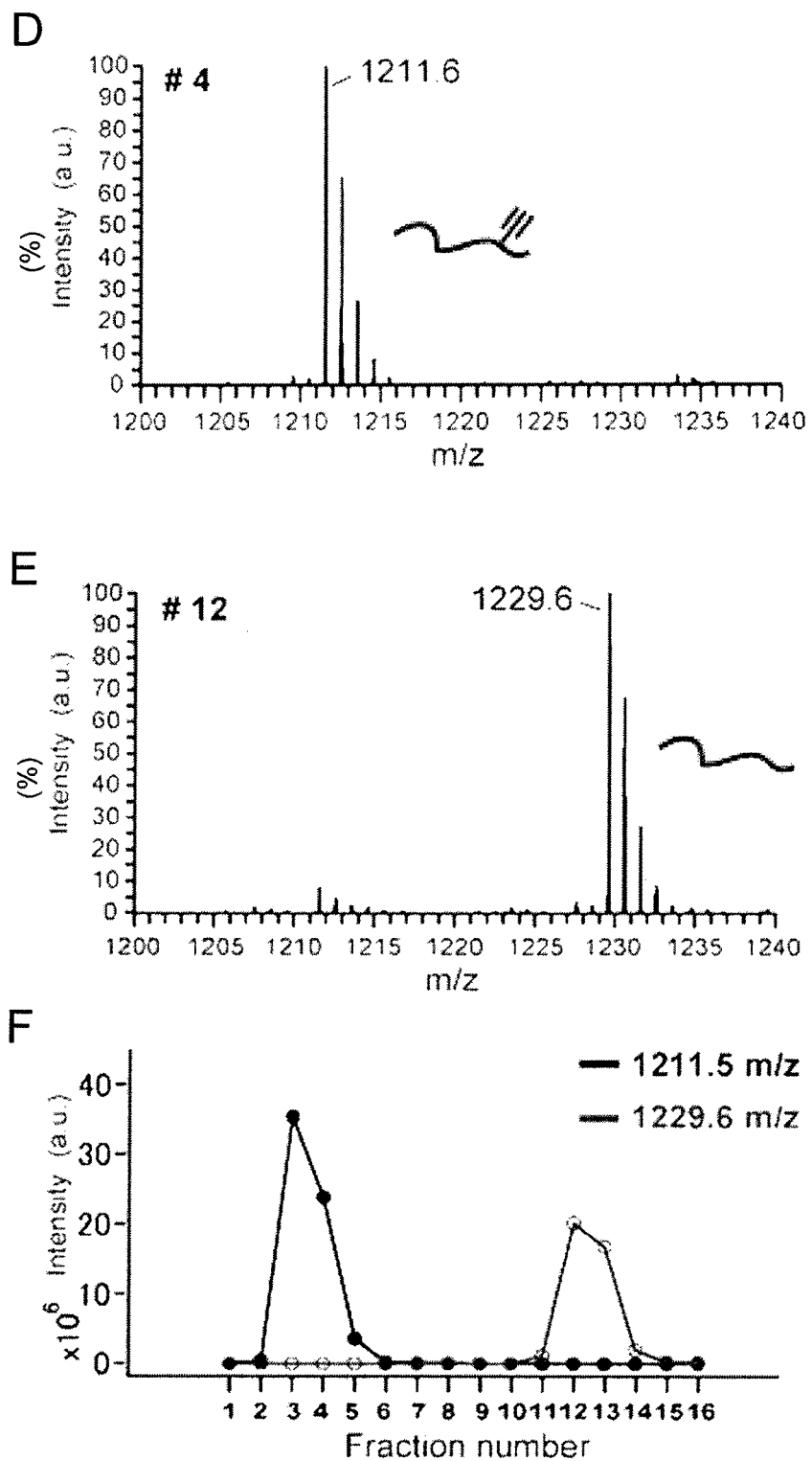
Figures 3, 9:
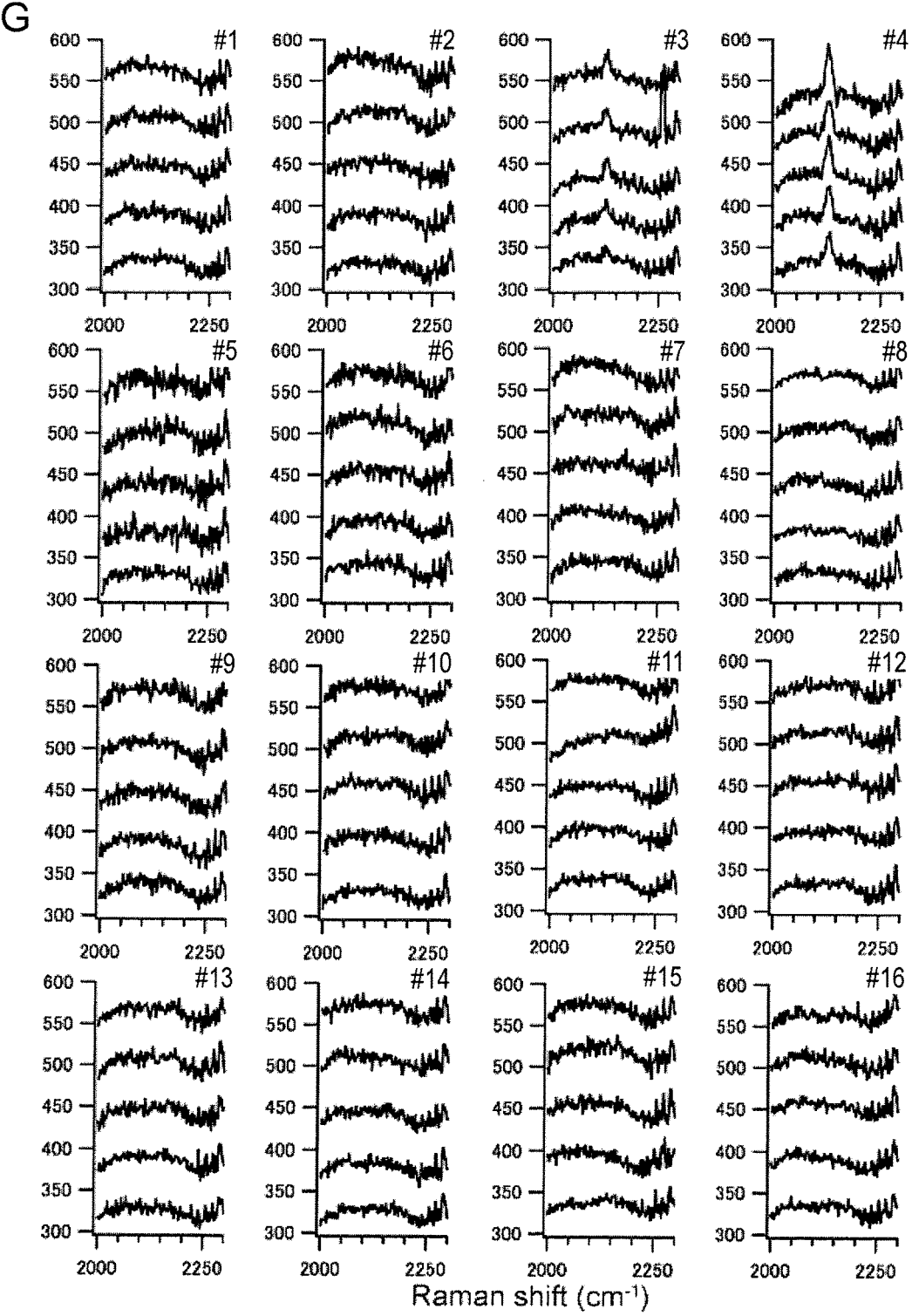

Next, it was confirmed that alkyne peptide 1 and unlabeled peptide 1 can be separated when contained in a mixture. FIG. 9 shows the results of separating the alkyne-labeled peptide and the unlabeled peptide from a mixture using the method according to the present invention. First, samples were fractionated by liquid chromatography depending on retention times. The results of measuring the fractions using a UV detector are shown in FIG. 9-1A. As shown in an enlarged view of the results, FIG. 9-1B, UV (280 nm) peaks were observed at 31 minutes and 33.2 minutes. The results of performing Raman spectroscopy for the fractions are shown in FIG. 9-3G. Raman peaks were observed for fractions 3 and 4, and no significant peak was observed for fractions 12 and 13. Therefore, peaks (fractions 3 and 4) at 31 minutes in FIG. 9-1B are attributed to the alkyne-labeled peptide, and peaks (fractions 12 and 13) at 33.2 minutes are attributed to the unlabeled peptide. These results are consistent with the mass spectrometric results (FIGS. 9-2D and E, respectively) for fractions 4 and 12. Experimental conditions were as described in "Experimental techniques" above.

Example 2 Preparation of a Low-Molecular-Weight Compound, RAT8-AOMK (S)-3-(2-((((4-ethynylbenzyl)oxy)carbonyl)amino)-3-phenyl propane amide)-2-oxopropyl 2,6-dimethylbenzoate) (hereinafter, referred to as RAT8-AOMK) was prepared by the following procedure.

NBoc-AOMK Synthesis 19 ml of 10% sodium hydroxide was added to a solution of THF (29 ml) of methylethyl 2-(2-((tert-butoxycarbonyl)amino)-3-phenyl propane amide) acetate (2.0 g, 5.7 mmol) and methanol (29 ml), and then the mixture was stirred at 10° C. for 10 minutes. After reaction, the solution was neutralized with 7.5% hydrochloric acid, followed by 6 times of extraction with dichloromethane. The solvent was removed under reduced pressure to prepare a THF (27 ml) solution. N-methylmorpholine (970 µl, 8.8 mmol) and isobutyl chloroformate (1.05 ml, 8.1 mmol) were added. After stirring at 10° C. for 30 minutes, diazomethane/diethylether was added. The mixture was stirred for at least 3 hours at room temperature, 33% HBr in acetic acid (10.5 ml) and an aqueous solution (10.5 ml) were added dropwise, followed by minutes of stirring at 0° C. The reaction was stopped with water-saturated $NaHCO_3$ and ethyl acetate, extraction was performed twice with ethyl acetate, and then the resultant was dried with magnesium sulfate. An organic layer was concentrated under reduced pressure, and then the resultant was purified using an ethyl acetate/hexane (2/1) solvent and a silica gel column, thereby obtaining colorless, non-crystalline bromomethylketone (1.55 g, 57%).

KF (874 mg, 15.0 mmol) and 2,6-dimethylbenzoic acid (733 mg, 4.89 mmol) were added to a bromomethylketone (1.5 g, 3.76 mmol)/DMF (9.4 ml) solution, followed by stirring at room temperature for 24 hours for reaction. DMF was evaporated to dryness under reduced pressure, and then dichloromethane and water were added. After separation, an aqueous layer was extracted twice with dichloromethane. The organic layer was concentrated under reduced pressure, and then the resultant was purified using an ethyl acetate/hexane (2/1) solvent and a silica gel column, thereby obtaining colorless and amorphous NBoc-AOMK (952 mg, 54%).

$[\alpha]_D^{26}$ −3.03 (c (0.760, $CHCl_3$)

$^1$H-NMR (400 MHz, $CDCl_3$) δ: 7.31-7.19 (6H, m), 7.04 (2H, d, J=7.7 Hz), 6.83 (1H, brs), 5.11 (1H, d, J=7.8 Hz), 4.88 (2H, s), 4.47 (1H, brs), 4.21 (2H, m), 3.10 (2H, m), 2.37 (6H, s), 1.39 (9H, s)

$^{13}$C-NMR (100 MHz, $CDCl_3$) δ: 198.6, 171.8, 168.9, 155.4, 136.4, 135.5, 132.1, 129.8, 129.2, 128.6, 127.7, 127.0, 80.3, 66.6, 55.6, 46.6, 38.2, 28.2, 19.8

MS (ESI) m/z value: 491 [(M+Na)$^+$]

HRMS (ESI) calculated value $C_{26}H_{32}N_2O_6Na$: 491.2153 (actual measured value: 491.2165).

RAT8-AOMK Synthesis

Trifluoroacetic acid was added to a dichloromethane (0.75 ml) solution of N-Boc-AOMK (83 mg, 177 μmol), followed by 30 minutes of stirring. The solvent was removed under reduced pressure, 4-nitrophenyl-4-ethynylbenzyl carbonate (35 mg, 118 μmol), N,N-diisopropylethylamine (160 μl, 1.6 mmol), and 4-dimethylaminopyridine (14 mg, 0.12 mmol) were added as a THF (0.74 ml) solution, followed by 2 hours of stirring at room temperature. After reaction, water and ethyl acetate were added, an aqueous layer and an organic layer were separated. The aqueous layer was extracted twice with ethyl acetate, and then dried with magnesium sulfate. The organic layer was concentrated under reduced pressure, and then purified with a silica gel column. Subsequently, gel filtration was performed, thereby obtaining colorless and amorphous RAT8-AOMK (34.7 mg, 56%).

$[\alpha]_D^{23}$ +0.66 (c 0.915, $CHCl_3$)

$^1$H-NMR (400 MHz, $CDCl_3$) δ: 7.43 (2H, d, J=8.3 Hz), 7.28-7.16 (8H, m), 7.04 (2H, d, J=7.8 Hz), 6.75 (1H, brs), 5.50 (1H, brd, J=7.2 Hz), 5.06 (1H, d, J=12.7 Hz), 5.00 (1H, d, J=12.7 Hz), 4.86 (2H, s), 4.53 (1H, m), 4.17 (2H, m), 3.09 (2H, m), 3.09 (1H, s), 2.36 (6H, s)

$^{13}$C-NMR (100 MHz, $CDCl_3$) δ: 198.6, 171.3, 169.0, 155.8, 136.8, 136.1, 135.6, 132.2, 132.1, 129.9, 129.2, 128.7, 127.7, 127.7, 127.1, 121.9, 83.2, 77.6, 66.6, 66.5, 56.0, 46.5, 38.4, 19.9

MS (ESI) m/z value: 549 [(M+Na)$^+$]

HRMS (ESI) calculated value $C_{31}H_{30}N_2O_6Na$: 549.1996 (actual measured value: 549.2012).

Example 3 Labeling of Cathepsin B with RAT8-AOMK

A sample lot, namely, FL-S10, containing cathepsin B labeled with RAT8-AOMK was prepared by the following procedure. Cathepsin B (6 μg, about 200 pmol, CALBIOCHEM Catalog No. 219362) was dissolved in 300 μl of a labeling buffer (50 mM acetic acid (pH 5.6), 5 mM $MgCl_2$, and 2 mM dithiothreitol (DTT)). The solution was left to stand at room temperature for 15 minutes, and then 3 μl of 2 mM RAT8-AOMK dissolved in 3.0 μl dimethyl sulfoxide (DMSO) was added to the solution. The mixture was incubated at 37° C. for 3 hours, and then the protein (cathepsin B) was precipitated by TCA precipitation. The thus obtained precipitate was dissolved in 20 μl of a denaturation buffer (7 M guanidinium hydrochloride (GuHCl)), 1M Tris-HCl (pH 8.5)), followed by 1 hour of incubation at 37° C. After reduction and alkylation with DTT and iodoacetamide (IAA), 1.5 μl of trypsin (100 ng/μl) was added to the sample, followed by several hours of incubation at 37° C. Hereinafter, the lot designated FL-S10 may also be referred to as the final sample. 9/10 of the final sample was used for a spotting experiment.

Example 4 Measurement of Raman Spectra of RAT8-AOMK and RAT8-AOMK-Labeled Cathepsin B The Raman spectra of the thus prepared RAT8-AOMK sample itself, and a sample itself containing RAT8-AOMK-labeled cathepsin B were measured.

Raman spectroscopy was performed using a laser Raman microscope (Nanophoton Corporation, Raman-11). The laser beam source was a laser with a wavelength of 532 nm. Laser intensity on the surface of a sample was 30 mW after the laser had passed through an objective lens and the exposure time was 30 seconds. The objective lens with a magnification of ×40 and a numerical aperture of 0.75 was used. Point illumination was selected as the illumination pattern for the laser. Raman spectra with wavenumbers of 710-3100 cm$^{-1}$ were obtained.

40-nm silver nanoparticles (Silver: 25 μl of silver colloids (40 nm, EMSC40, British BioCell International)) were used for SERS.

Figure 25:
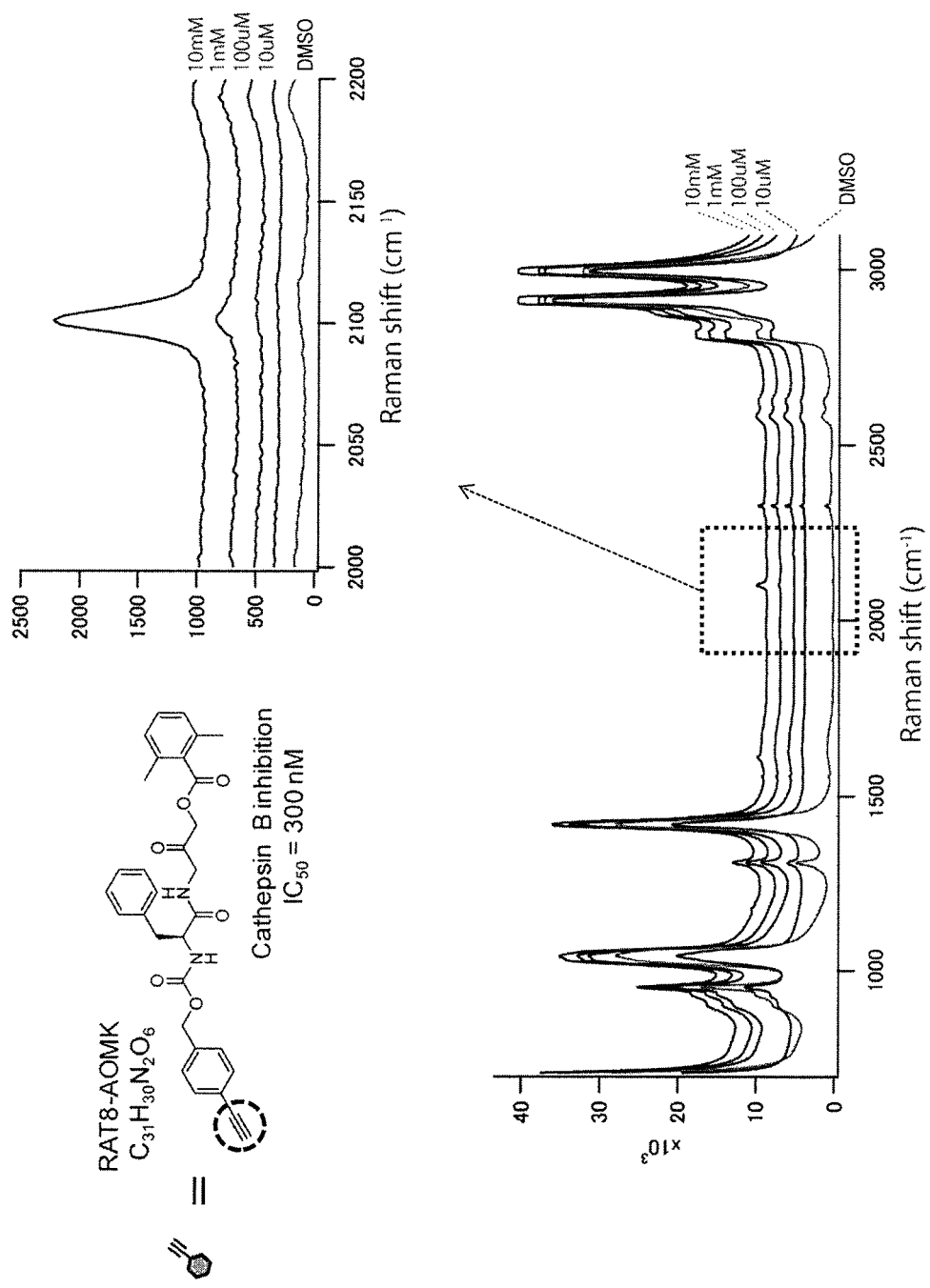
FIG. 25 shows the Raman spectrum of RAT8-AOMK. An alkyne-derived Raman peak was observed in the vicinity of 2100 (cm$^{-1}$).
Figure 26:
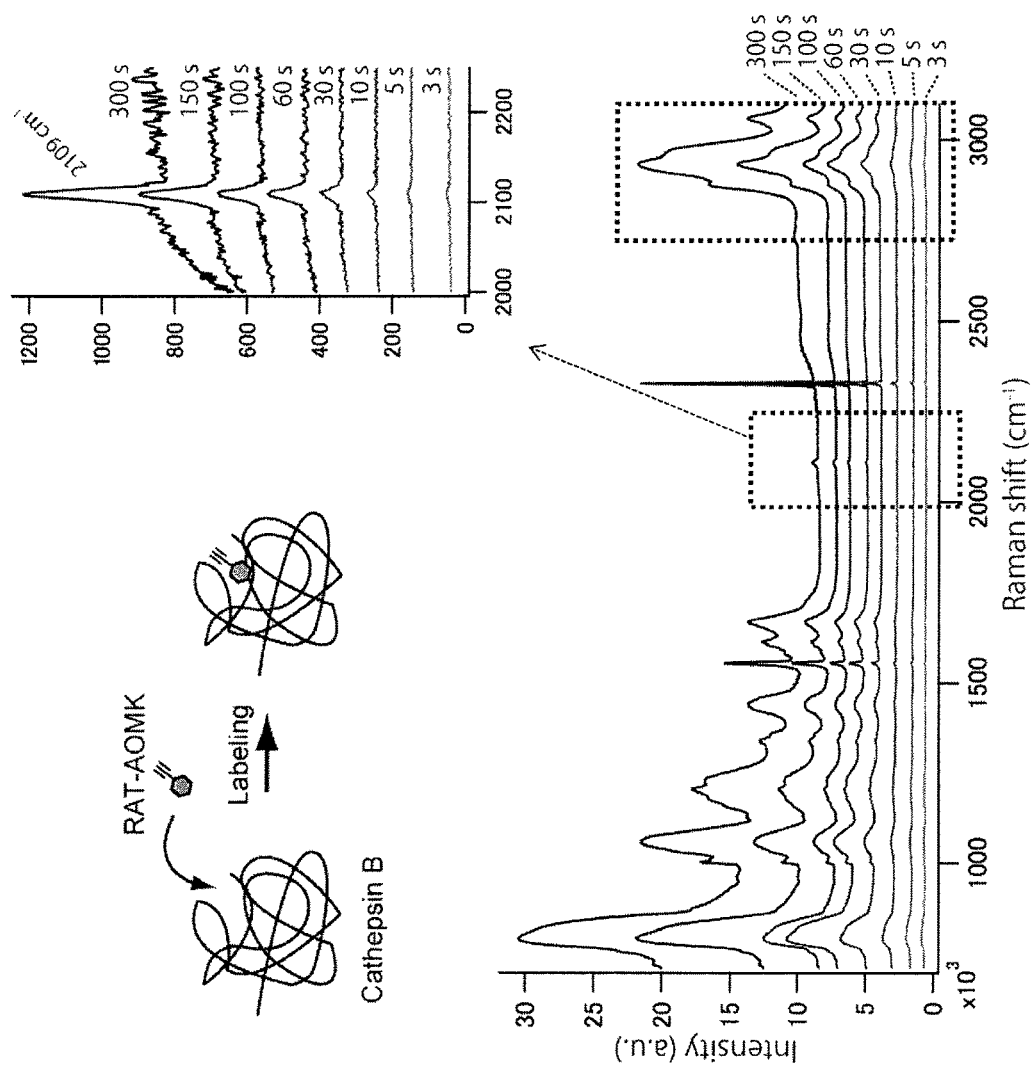
FIG. 26 shows the Raman spectrum of RAT8-AOMK-bound cathepsin B. Raman peaks from proteins were observed at 2800-3100 (cm$^{-1}$) in the spectrum in the lower section. In the vicinity of 2100 (cm$^{-1}$), an alkyne-derived Raman peak was observed. The upper right section shows an enlarged view of the alkyne-derived Raman peak.

Raman spectroscopic results are shown in FIG. 25 and FIG. 26. When the Raman spectrum of RAT8-AOMK itself was analyzed, as shown in the upper right section of FIG. 25, an alkyne-derived Raman peak was observed in the vicinity of 2100 cm$^{-1}$. FIG. 25 shows in the lower section the Raman spectra obtained with various concentrations of the samples. Furthermore, the Raman spectrum of RAT8-AOMK-labeled cathepsin B was analyzed. As shown in the upper right section of FIG. 26, the alkyne-derived Raman peak was observed in the vicinity of 2109 cm$^{-1}$. Moreover, the lower section of FIG. 26 shows the Raman spectra obtained with various concentrations of the samples. In addition to the alkyne-derived peak, a protein-derived Raman peak was confirmed at the same time.

The results of SERS using silver nanoparticles are shown in FIG. 12. When silver nanoparticles having a diameter of 40 nm were used, the Raman peak intensity of RAT8-AOMK was increased by 10$^3$ or more. The exposure time was 10 seconds. FIG. 12 shows on the left a low-intensity spectrum obtained when no silver particles were used and a high-intensity spectrum obtained when silver particles were used. This similarly applies to the central spectra in FIG. 12. EMSC40 (British BioCell International) was used as silver nanoparticles. A mixture (0.5 μl) prepared by mixing the silver nanoparticles with ethanol having the same weight as that of the silver nanoparticles was added dropwise onto a glass substrate. After drying, a RAT8-AOMK (dissolved in DMSO) solution (0.5 μl) was added dropwise onto the glass substrate, and then SERS measurement was performed.

Example 5 Liquid Chromatography

<Nano LC-Probot>

Figure 20:
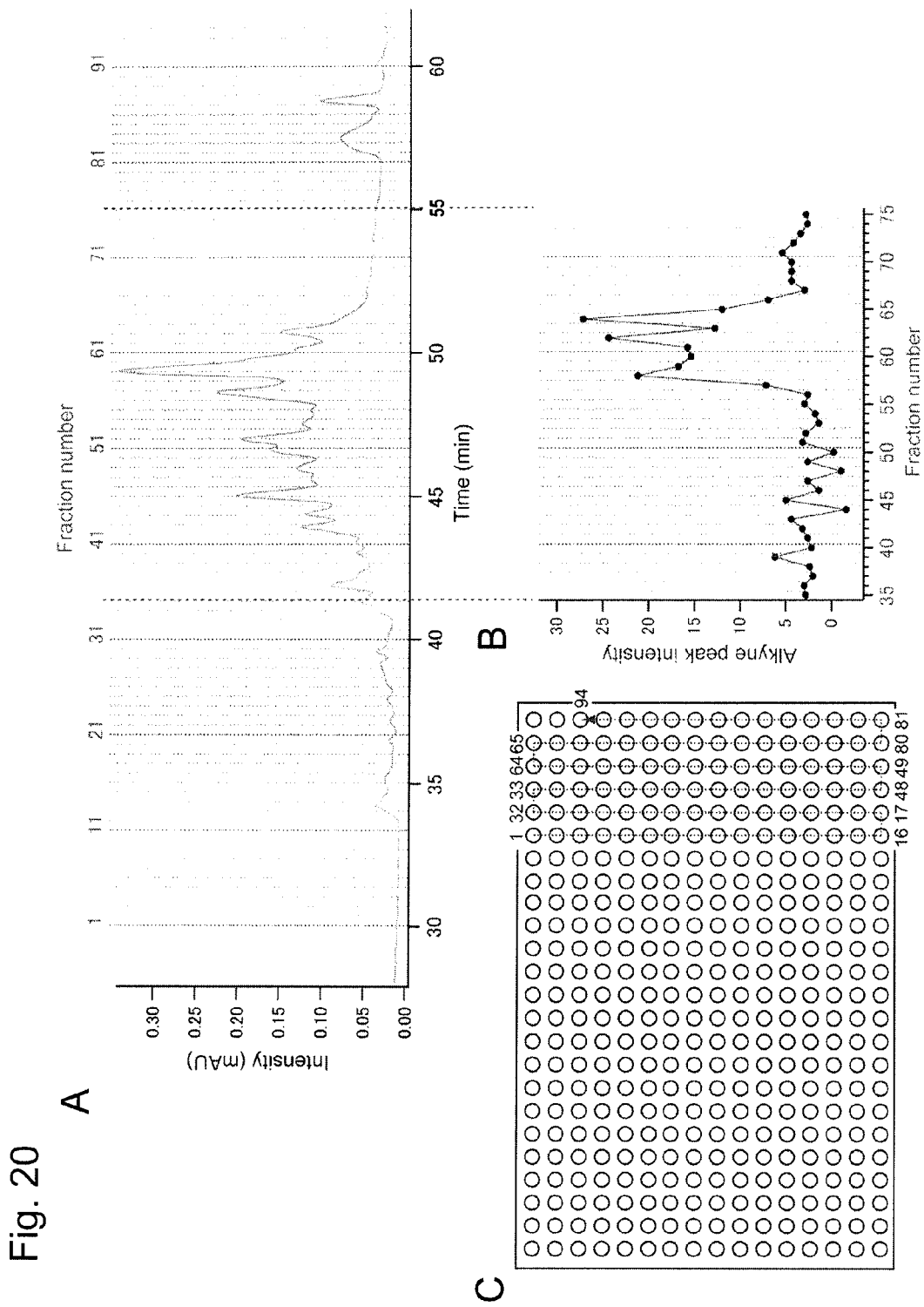
FIG. 20 shows the correspondence between a UV chromatogram and a Raman chromatogram.

The sample lot, FL-S10, prepared by the above method was lyophilized, and then dissolved in 26 μl of water. 25 μl out of 26 μl of the sample was injected into nano LC (NanoFrontier nLC, Hitachi) provided with a UV detector (MU701, GL science) for fractionation. The flow rate was 250 nL/minutes. Fractions were spotted at a spotting rate of 20 seconds/spot onto a MALDI plate (ITOP plate, Thermo)

using a fraction collector (Probot, Dionnex). A UV chromatogram is shown in FIG. 20A. FIG. 20C shows the order of spotting fractions. As shown in FIG. 20A, UV absorption was observed for fractions Nos. 35-75. Next, Raman spectroscopy and mass spectrometry were performed for this range by the following procedure.

Figure 27:
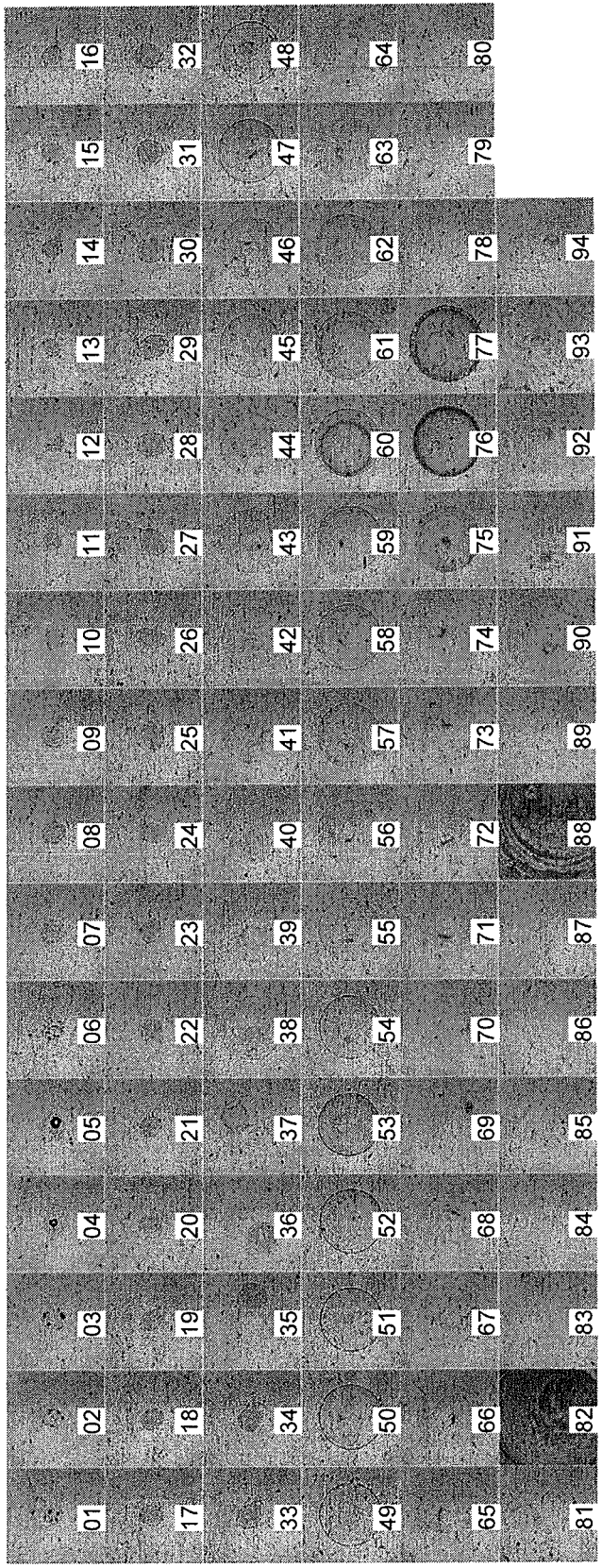
FIG. 27 shows a light-field image of 94 sample spots.

Example 6 MALDI Mass Spectral Analysis of Concentrated RAT8-AOMK-Labeled Cathepsin B Spotted A solution containing concentrated RAT8-AOMK-labeled cathepsin B (lot FL-S10) was spotted onto a MALDI plate using nano LC-UV-probot (250 nl/minute, 20 seconds/well, about 200 pmol). FIG. 27 shows a light-field image of fraction Nos. 1-94 spotted onto the MALDI plate. Solvents in spots were vaporized by a drying step, and thus samples were concentrated. The sample lot, FL-S10, containing the concentrated RAT8-AOMK-labeled cathepsin B was measured by the Raman spectroscopy method. Alkyne signals were detected from multiple spots. Therefore, mass spectra were manually obtained from the same target plate using MALDI-Orbitrap spectrometer.

<Raman Spectroscopy>

Figure 21:
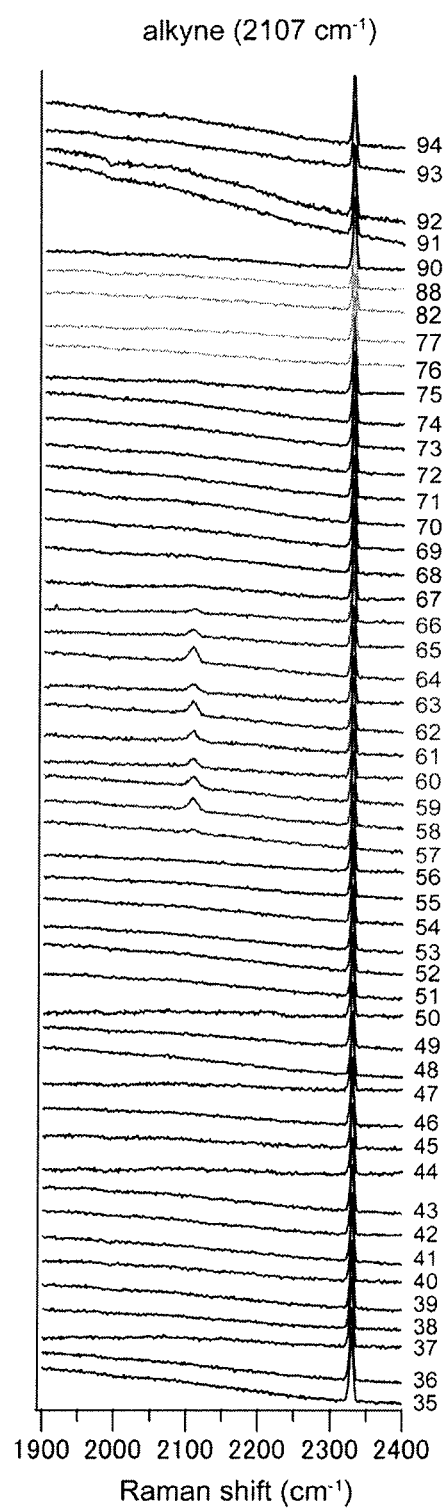
FIG. 21 shows the Raman spectra of fraction Nos. 35-94. In the case of fraction Nos. 57-66, characteristic Raman peaks were observed in the vicinity of 2106 cm$^{-1}$.
Figure 23:
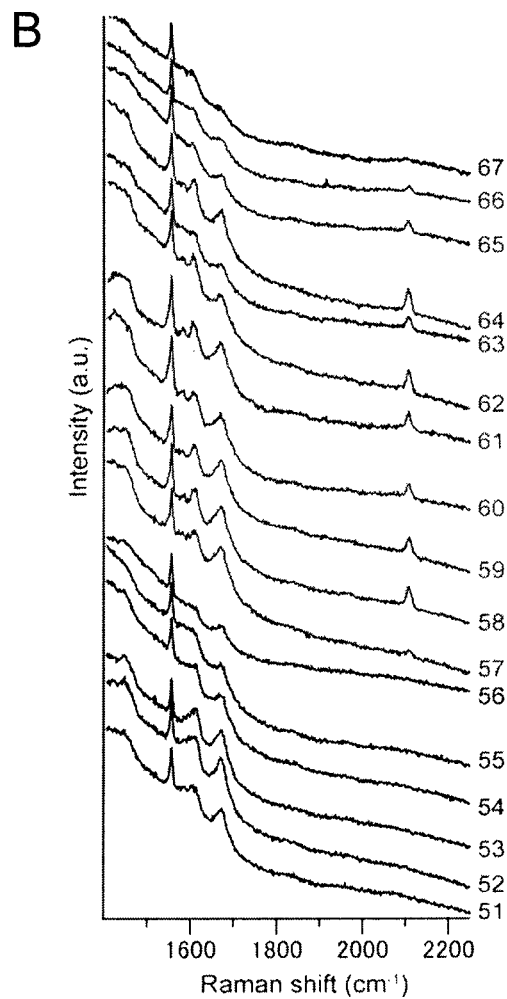
Figure 2:
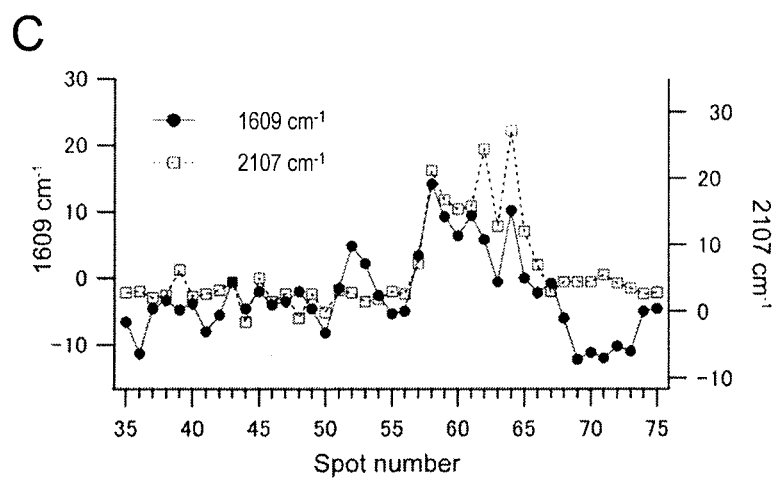

Raman spectroscopy was performed as described in Example 5. The results are shown in FIG. 21 and FIG. 23.

<MALDI MS Analysis>

Matrix: DHB
Mass range: m/z 800-4,000
Mode used to obtain mass spectra: Fourier transform (FT), resolution of 30,000, and laser energy of 5-8 µJ <Separation of Samples with LC and Detection with UV>

The sample containing the RAT8-AOMK-labeled cathepsin B fragment was fractionated using nano LC-UV-probot. The UV chromatogram of the sample injected into nano LC is shown in FIG. 20A. For the sake of convenience, the region of the retention time of 30-60 minutes is enlarged and shown. UV detection was performed at 214 nm. The solvent used was water-acetonitrile. In this experiment, acetonitrile concentration (gradient) was increased linearly for 60 minutes from 5% to 80%. The starting concentration of cathepsin B was 200 pmol (3 µg). 9/10 of the final sample (lot FL-S10) was injected into nano LC. These fractions were spotted onto a MALDI plate. Starting from this time point, after 30 minutes of the total time for elution with LC, fractions were collected at intervals of 20 seconds, and then spotted. The total number of fractions was 94. FIG. 20A shows the relationship between the retention time and fraction Nos. in the UV chromatogram. FIG. 20B (below FIG. 20A) shows the Raman spectrum in which alkyne (2107 $cm^{-1}$) peak intensities were plotted to correspond to FIG. 20A. Alkyne signals were obtained for fraction Nos. 57-66, demonstrating the existence of the RAT8-AOMK-labeled peptide.

<Techniques and Results of Raman Spectroscopy>

Raman spectroscopy was performed using a laser Raman microscope (Nanophoton Corporation, Raman-11). The laser beam source was a laser with a wavelength of 532 nm. Laser intensity on the surface of a sample was 30 mW after the laser had passed through an objective lens and the exposure time was 30 seconds. The objective lens with a magnification of ×40 and a numerical aperture of 0.75 was used. Point illumination was selected as the illumination pattern for the laser. Raman spectra with wavenumbers of 710-3100 $cm^{-1}$ were obtained. Silver nanoparticles were not used.

Raman spectra obtained from fraction Nos. 35-94 are shown in FIG. 21. Raman spectra were obtained repeatedly 5 times for each spot, averaged, and then shown. The alkyne peak intensities for fraction Nos. 35-75 are shown in FIG. 20C.

FIG. 27 shows a light-field image of 94 sample spots on the MALDI plate. Raman measurement was performed by focusing the Raman microscope onto an aggregation portion. Fraction No. 35 is consistent (agrees) with the starting point at which the UV peak intensity began to increase. After Raman measurement, MALDI mass spectrometry was performed for each spot by the following procedure.

Figure 28:
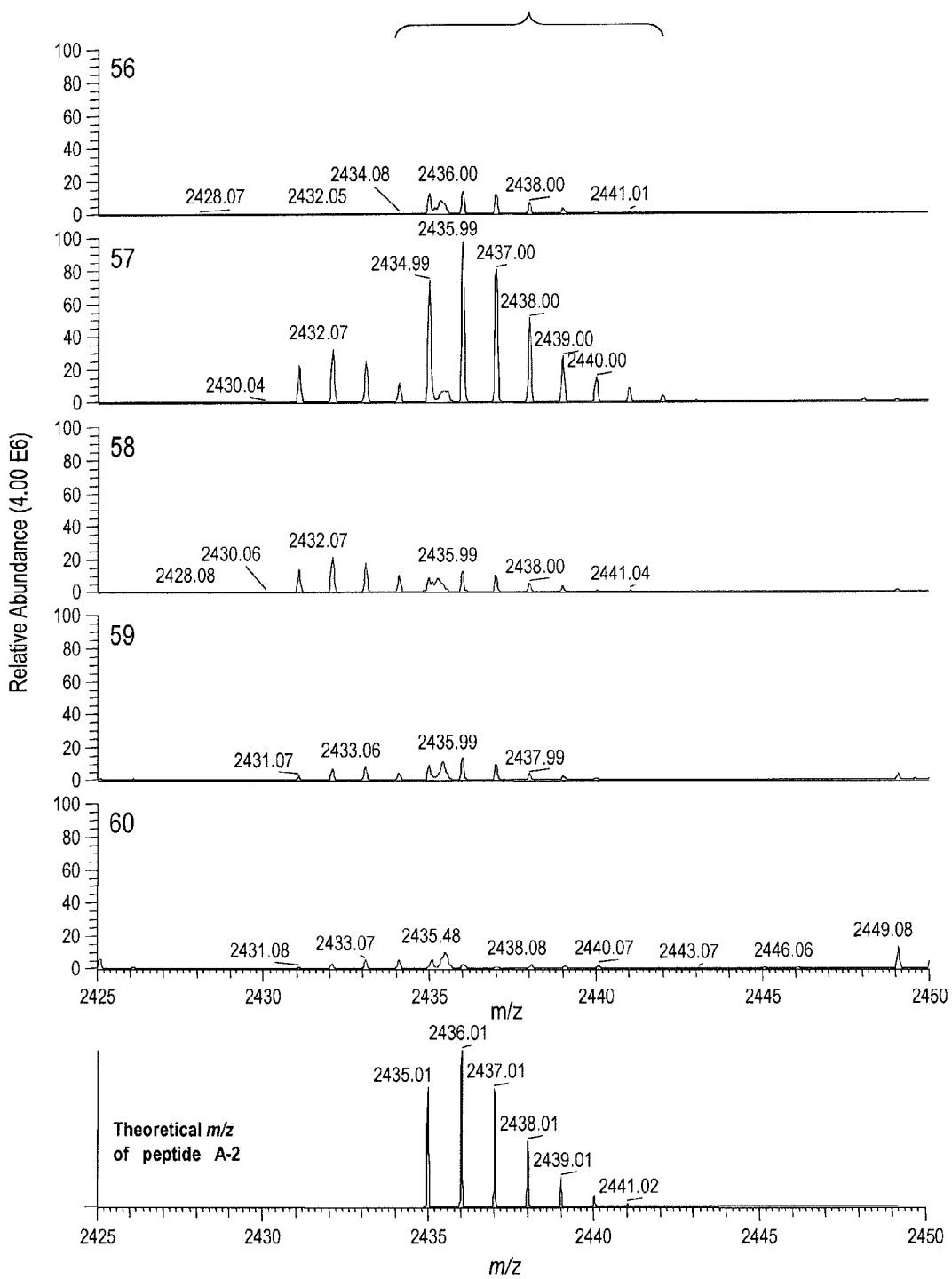
FIG. 28 shows the MALDI mass spectra of fraction Nos. 56-60 (peptide A-2). The scale was fixed at 4E$^6$. Peptide A-2 (no cleavage error, +RAT8-AOMK), m/z 2435.0067.
Figure 29:
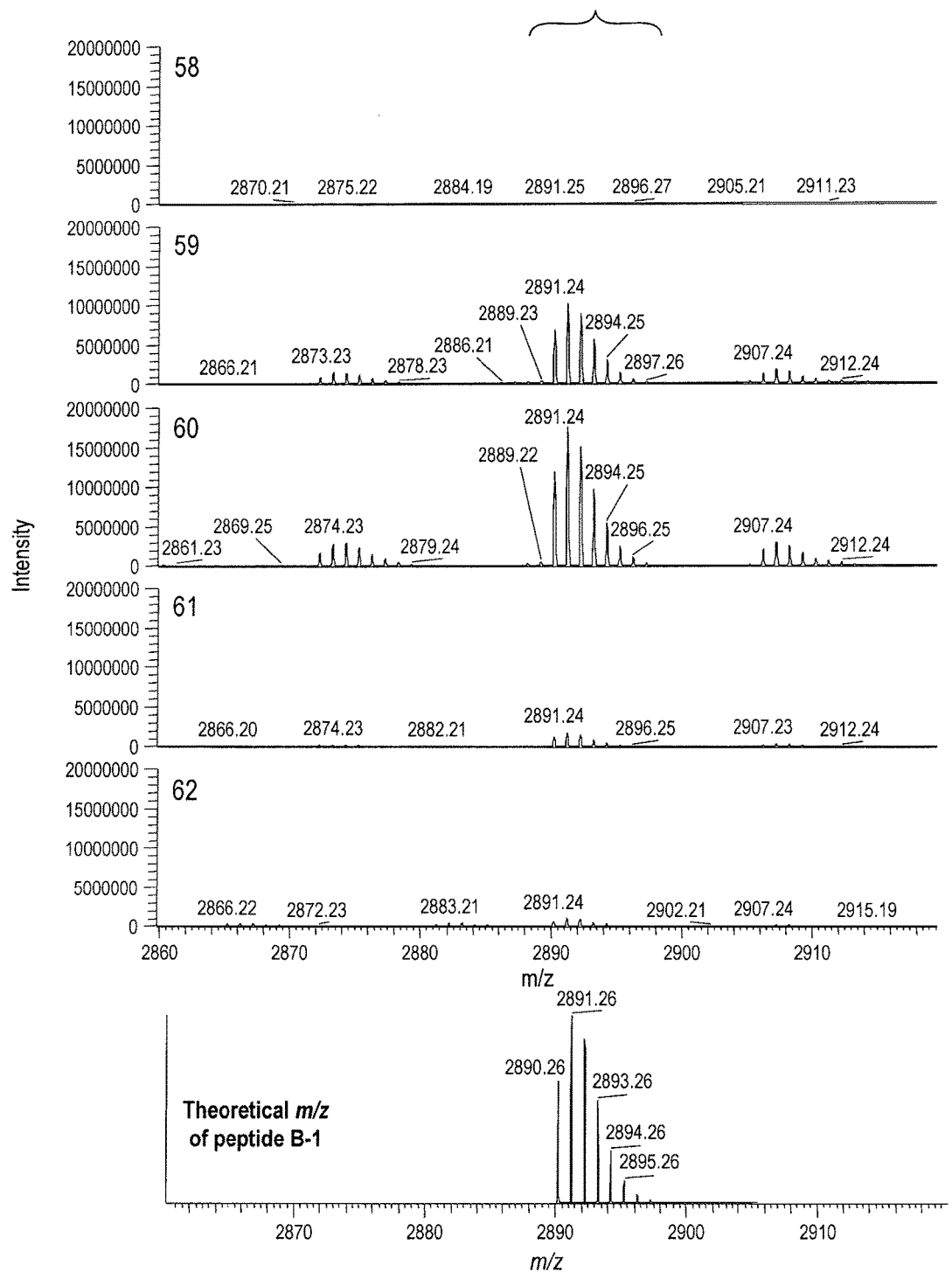
FIG. 29 shows the MALDI mass spectra of fraction Nos. 58-62 (peptide B-1). The scale was fixed at 2E$^7$. Peptide B-1 (1 cleavage error, +RAT8-AOMK+CAM), m/z 2890.2559.
Figure 30:
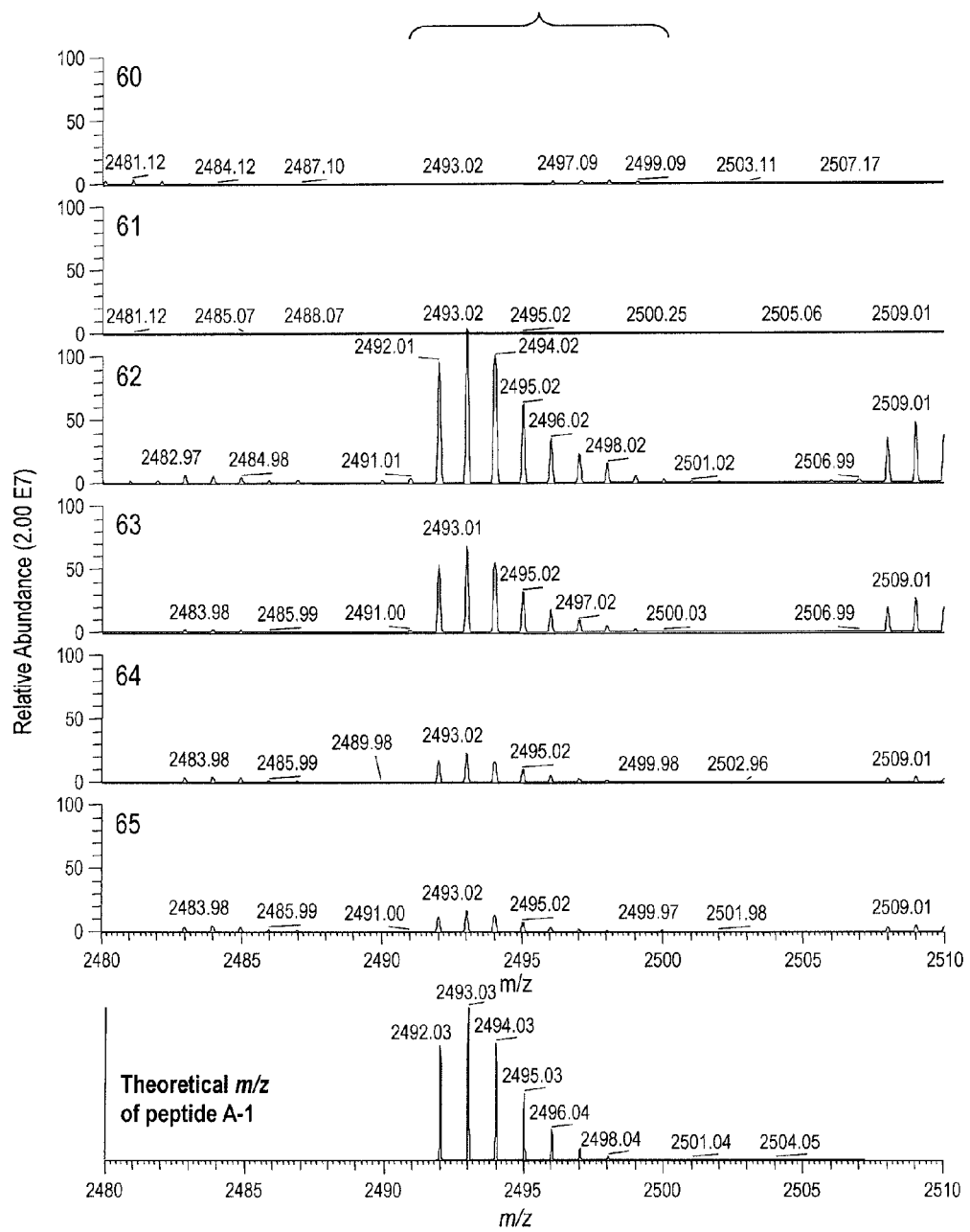
FIG. 30 shows the MALDI mass spectra of fraction Nos. 60-65 (peptide A-1). The scale was fixed at 2E$^7$. Peptide A-1 (no cleavage error, +RAT8-AOMK+CAM), m/z 2492.0282.
Figure 31:
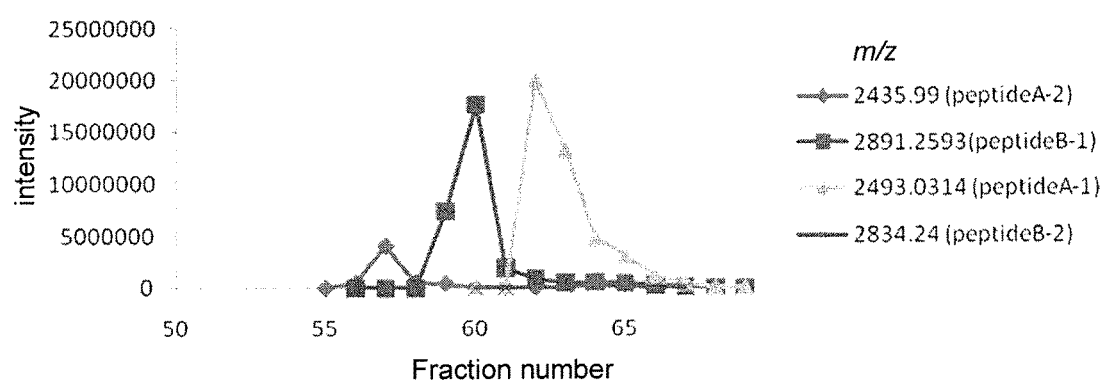
FIG. 31 shows a summary of the results of FIGS. 27-29 and specifically shows the ion count numbers of target peptides of fraction Nos. 50-69. The horizontal axis indicates fraction Nos., and the vertical axis indicates ion count numbers.

The results of performing mass spectrometry for each spot subjected to Raman measurement as described above are shown in FIG. 28 to FIG. 31. FIG. 28 shows the mass spectra of fraction Nos. 56-60. The theoretical m/z values of peptide A-2 (DQGSCGSCWAFGAVEAISDR+RAT8-AOMK) are shown in the lowermost section of FIG. 28. The region corresponding to the theoretical spectrum of peptide A-2 shown in the lowermost section is indicated with uppermost parentheses. The most intensive peak was detected for fraction No. 57. FIG. 29 shows the mass spectra of fraction Nos. 58-62. Theoretical m/z values of peptide B-1 (EIRDQGSCGSCWAFGAVEAISD+carbamide methyl+RAT8-AOMK) are shown in the lowermost section of FIG. 29. FIG. 30 shows the mass spectra of fraction Nos. 60-65. The theoretical m/z values of peptide A-1 (DQGSCGSCWAFGAVEAISDR+carbamide methyl+RAT8-AOMK) are shown in the lowermost section of FIG. 30. These results were superimposed, as shown in FIG. 31. Peptide A-2 was observed for fraction No. 57 at the highest level, peptide B-1 was observed for fraction No. 60 at the highest level, and peptide A-1 was observed for fraction No. 62 at the highest level (fraction No. is the number of each well on the MALDI plate).

Mainly 3 types of AOMK-labeled peptide were detected, as described above. These peptides exhibited retention times differing from each other. The alkyne peak was observed in a relatively wide range. Three types of peptide are as summarized follows.

Fraction Nos. 56-60 [57]: peptide A-2, DQGSCGSCWAFGAVEAISDR (+RAT8-AOMK)

Fraction Nos. 59-67 [60]: peptide B-1, EIRDQGSCGSCWAFGAVEAISDR (+RAT8-AOMK, +carbamide methyl)

Fraction Nos. 61-69 [62]: peptide A-1, DQGSCGSCWAFGAVEAISDR (+RAT8-AOMK, +carbamide methyl)

(Numbers within parentheses indicate fraction No(s)., for which the most intense ion peak was observed).

Figures 1, 22:
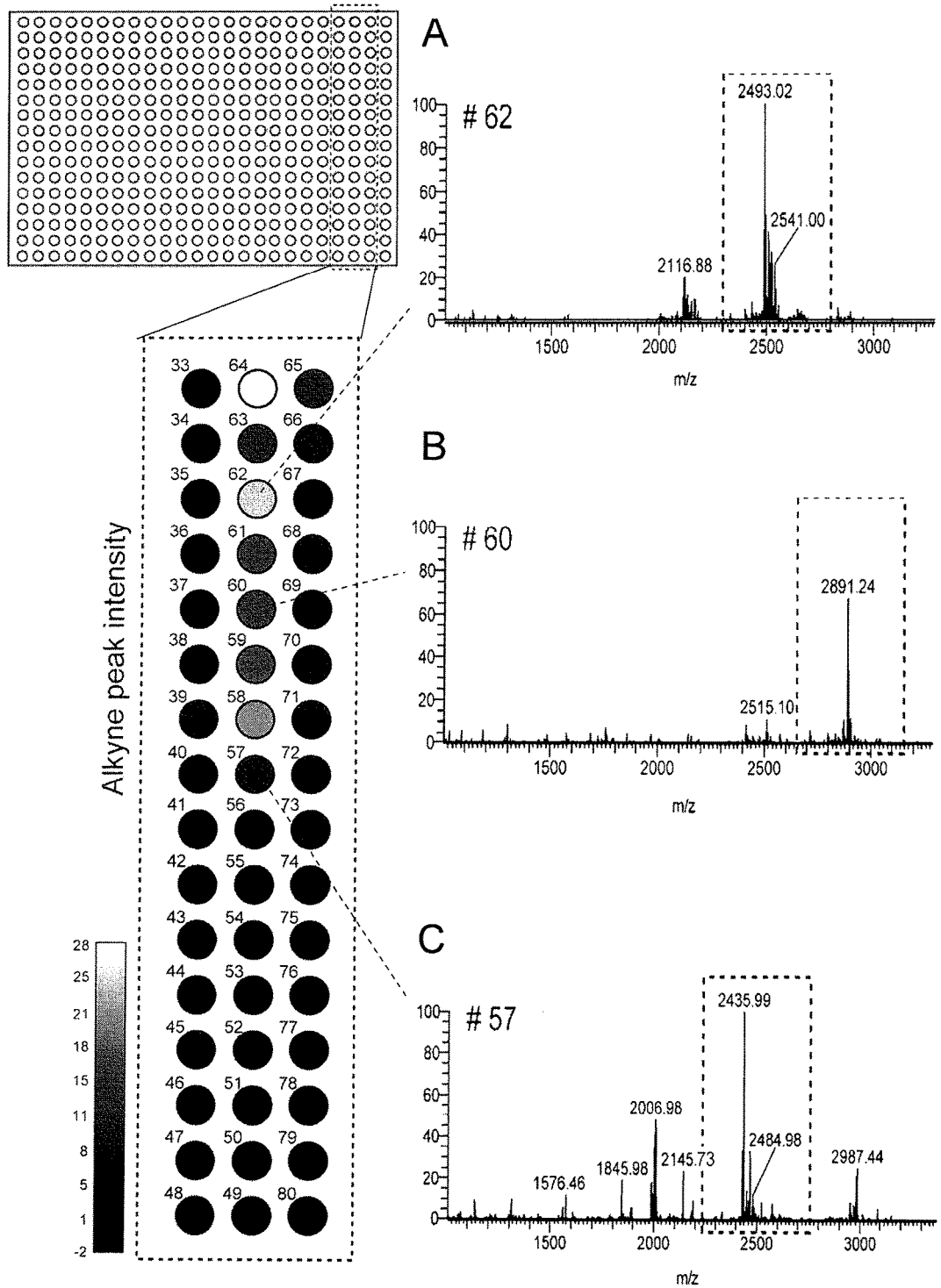

FIG. 22 shows the MALDI mass spectra obtained for spots detected by Raman screening. The alkyne peak intensity map on the left in FIG. 22-1 corresponds to the peak intensity profile in FIG. 20. In the mass spectra of fractions for which Alkyne signals were obtained, AOMK-labeled peptide peaks were observed (FIGS. 22-1A, B, and C). FIG. 22-2 shows each experimental result compared with the relevant calculated value. Mass spectra that were consistent well with the calculated mass of a peptide fragment bound to the low-molecular-weight compound, RAT8-AOMK, were obtained from fraction Nos. observed to exhibit Raman peaks. For example, the mass spectrum of fraction No. 62 exhibited a spectrum having a peak at m/z 2492, for example, and was attributed to peptide A-1 (DQGSCGSCWAFGAVEAISDR+carbamide methyl+RAT8-AOMK). The calculated mass-charge ratio (m/z) of $C_{109}H_{150}N_{28}O_{36}S_2$ is 2492.0282 Da. The mass spectrum of fraction No. 60 was attributed to peptide B-1 (EIRDQG- SCGSCWAFGAVEAISDR+carbamide methyl+RAT8-AOMK). The calculated m/z of $C_{126}H_{180}N_{34}O_{41}S_2$ was 2890.2559 Da. The mass spectrum of fraction No. 57 was attributed to peptide A-2 (DQGSCGSCWAFGAVEAISDR+RAT8-AOMK). The calculated m/z of $C_{107}H_{147}N_{27}O_{35}S_2$ was 2435.0067.

When mass spectrometry was performed for a spot (fraction No. 50), for which no alkyne signals were observed, an unlabeled peptide fragment was confirmed (peptide NGPVEGAFSVYSDFLLYK, SEQ ID NO: 5, 2004.98 Da). This demonstrates that MALDI mass spectral analysis can be performed not only for labeled peptides, but also for unlabeled peptides. Spots, for which AOMK-labeled peptides and an unlabeled peptide were observed by MALDI mass spectrometry, are shown roughly in FIG. 24. Only a peptide was detected for fraction No. 50. AOMK-labeled peptides were detected for around fraction Nos. 57-66.

Furthermore, whether or not different Raman peaks can be used for screening for an AOMK-labeled peptide was examined. Intact RAT8-AOMK (neat) has two unique Raman peaks (shown in the lower section of FIG. 23A). One peak was found at 2106 cm$^{-1}$ and is attributed to the alkyne vibration. Another peak at 1610 cm$^{-1}$ is attributed to the phenyl ring vibration. The upper and the middle sections of FIG. 23A show the Raman spectrum of intact RAT8-AOMK (neat) and the same of fraction Nos. 35-75 corresponding with one another. Peaks were observed at 1609 cm$^{-1}$ for fraction Nos. 57-66. FIG. 23C shows the peak intensity profile when Raman spectra were measured at 2107 cm$^{-1}$ and 1609 cm$^{-1}$. Raman peaks of both alkyne and a phenyl ring appeared overlapping with each other for around fractions Nos. 57-66. The Raman peak intensity of a phenyl ring was relatively low, but exhibited a profile similar to that of alkyne. This demonstrates that not only the Raman peak of alkyne, but also the Raman peak derived from a phenyl ring of the original compound not labeled with alkyne can also be used for Raman screening. However, one type of amino acid, namely, phenylalanine, is known to exhibit a Raman peak at 1602 cm$^{-1}$, and thus Raman signals derived from such protein/peptide within the finger print region appear in the background and, therefore, attention should be paid to the presence thereof.

In MALDI-Orbitrap analysis, CHCA or DHB was used as the matrix. In general, CHCA can readily form homogenous co-crystals and enables obtaining spectra with high density, and therefore CHCA is suitable for automatic analysis. On the other hand, the co-crystal of DHB is not homogenous but acicular (needle like), and increases peptide coverage (encompassing range) of the protein in many cases. Therefore, it is important to select the matrix depending on the properties of the sample being analyzed and the purpose of the measurement. The theoretical mass of each peptide is as described below. The above experimental results are well consistent with these theoretical values.

<Trypsin-Degraded Peptide of Theoretical Cathepsin B: Amino Acid Sequence and Element Composition/Mass>
Peptide A, cleavage error: none
DQGSCGSCWAFGAVEAISDR; $C_{85}H_{127}N_{25}O_{31}S_2$
*monoisotopic mass of 2057.857 Da, average mass of 2059.197 Da (*the term "monoisotopic mass" refers to the mass based only on the principal isotope of each element composting a target molecule.)
Peptide B, cleavage error: 1
EIRDQGSCGSCWAFGAVEAISDR; $C_{102}H_{157}N_{31}O_{36}S_2$
Monoisotopic mass of 2456.085 Da, average mass of 2457.654 Da <Increase by Each Modification>
Carbamide methyl (Cys)
Monoisotopic mass of 57.021464 Da, average mass of 57.0513 Da Composition $H_3C_2N\,O$
RAT8-AOMK (Cys)
Monoisotopic mass of 376.142307 Da, average mass of 376.4052 Da Composition $C_{22}H_{20}N_2O_4$
<Calculated m/z>
Peptide A Series
 Peptide A-1
 DQGSCGSCWAFGAVEAISDR; $C_{109}H_{150}N_{28}O_{36}S_2$
 Carbamide methyl (Cys); RAT8-AOMK (Cys)
 Monoisotopic m/z: 2492.0282
 Peptide A-2
 DQGSCGSCWAFGAVEAISDR; $C_{107}H_{147}N_{27}O_{35}S_2$
 RAT8-AOMK (Cys)
 Monoisotopic m/z 2435.0067
Peptide B Series
 Peptide B-1
 EIRDQGSCGSCWAFGAVEAISDR; $C_{126}H_{180}N_{34}O_{41}S_2$
 Carbamide methyl (Cys); RAT8-AOMK (Cys)
 Monoisotopic m/z: 2890.2559.

Figure 33:
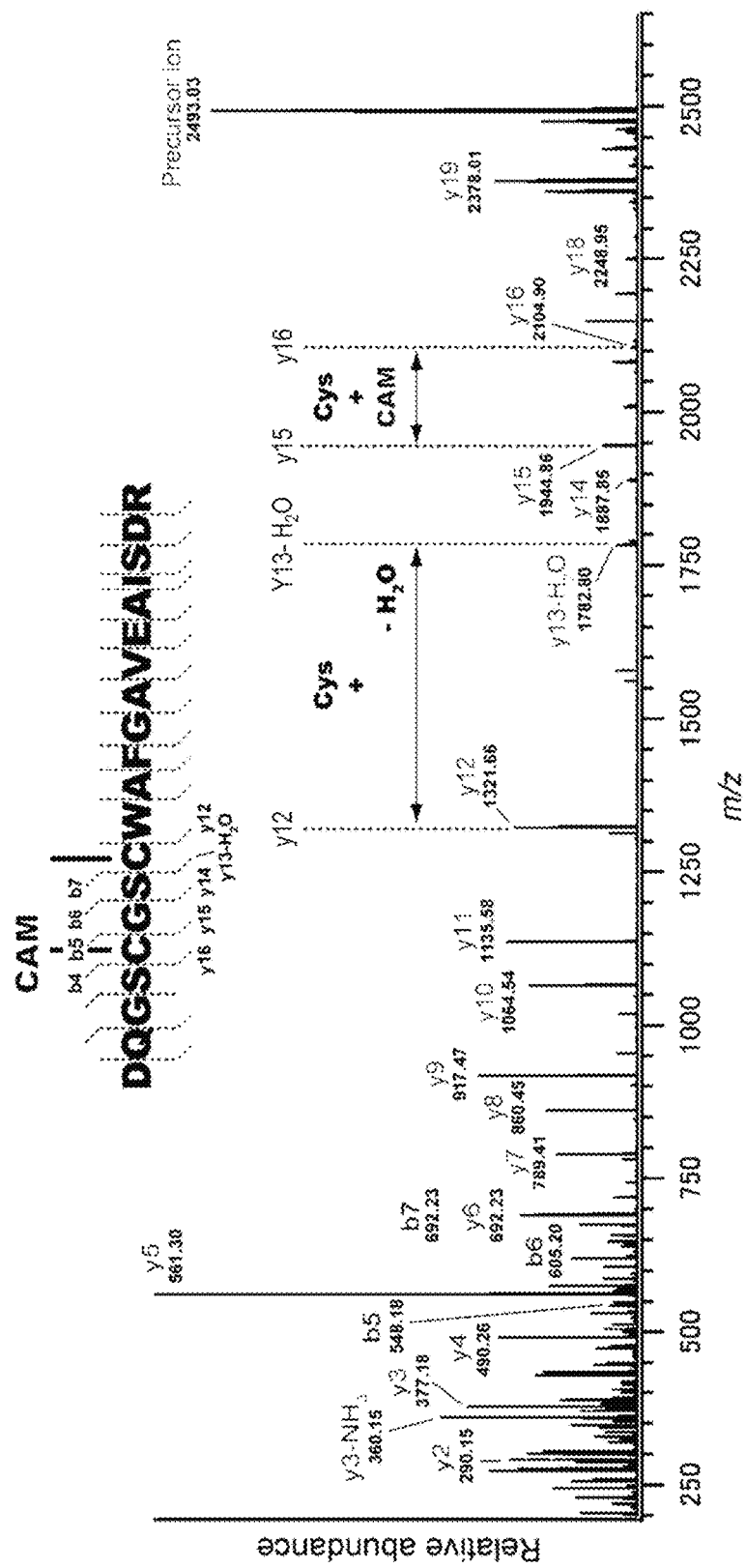
FIG. 33 shows the MS/MS spectrum of RAT8-AOMK-bound peptide A-1.

Example 7 MALDI-MS/MS Spectral Analysis of Concentrated RAT8-AOMK-Labeled Cathepsin B Spotted A sample spotted onto a MALDI plate under experimental conditions similar to those for concentrated RAT8-AOMK-labeled cathepsin B described in Example 6 was measured by the Raman spectroscopy method. MS/MS analysis was performed using a MALDI-Orbitrap spectrometer for fractions for which alkyne signals had been detected. FIG. 33 shows MS/MS spectra obtained from fractions for which peptide A-1 (DQGSCGSCWAFGAVEAISDR+carbamide methyl+RAT8-AOMK) had been detected. The thus obtained fragment ions were analyzed. As a result, a difference in mass number (the mass number was found by subtracting 18.0 Da due to dehydration from the sum of 376.1 Da corresponding to the mass of RAT8-AOMK and 103.0 Da corresponding to cysteine residue) was observed between a C-terminal fragment ion (y12) that had been cleaved on the N-terminus of the 12$^{th}$ tryptophan residue (counted from the C-terminus of the peptide) and a C-terminal fragment ion (y13) that had been cleaved on the N-terminus of the 13$^{th}$ cysteine residue. On the other hand, a difference in mass number corresponding to the sum of 57.0 Da corresponding to the mass of carbamide methyl and 103.0 Da corresponding to cysteine was observed between a C-terminal fragment ion (y15) that had been cleaved on the N-terminus of the 15$^{th}$ glycine residue (counted from the C-terminus) and a C-terminal fragment ion (y16) that had been cleaved on the N-terminus of the 16$^{th}$ cysteine residue. It was determined from the above results that, of two cysteine residues contained in the peptide DQGSCG-SCWAFGAVEAISDR, the 13$^{th}$ cysteine residue (counted from the C-terminus) was modified by RAT8-AOMK.

<MALDI MS/MS Analysis>
Matrix: CHCA
Mass range: m/z 200-3,000
Mode to obtain mass spectrum: Fourier transform (FT), resolution 15,000, and laser energy 5-8 μJ
MS/MS method: HCD (higher energy collision dissociation)
<Peptide to be Subjected to MS/MS Analysis>
Peptide A-1

Example 8 Metal Substrate and Quartz Substrate

The present inventors have developed a plate for smoothly performing Raman spectroscopy and mass spectrometry for spotted samples. FIG. 14 shows a plate for smoothly performing Raman spectroscopy and mass spectrometry for spotted samples. FIG. 14 shows in the upper left section a plate for fixing a substrate for a microscope. A photograph shows a multi-spotted metal substrate viewed from the back. FIG. 14 shows in the lower left section a sample stand for a Raman microscope. FIG. 14 shows on the right the plate for fixing the substrate for a microscope, which is mounted on the sample stand. Raman screening (Raman spectroscopy) is performed under the state. The multi-spotted metal substrate was used after confirmation of the cleaned surface of a MALDI metal plate (Thermo).

In Raman measurement, a quartz substrate is advantageous. As a quartz substrate, synthetic quartz (Starbar Japan, φ25 mm×0.17 mm) was used after confirmation of the cleanliness of the surface. This can be directly used for MALDI-MS measurement. FIG. 16 shows on the left a quartz substrate that is advantageous for Raman measurement. The results of spotting a peptide and an alkyne peptide onto the substrate, and then performing Raman spectroscopy are shown in the upper right section of FIG. 16. While a Raman peak unique to alkyne was observed at 2123 $cm^{-1}$ for the alkyne peptide, no Raman peak was observed in the region for the peptide. Moreover, FIG. 16 shows in the lower right section the results of directly using the quartz substrate for MALDI-MS measurement. A peak of the alkyne peptide was detected in the vicinity of m/z 1211, and a peak of the peptide was detected in the vicinity of m/z 1229. As described above, with the use of the quartz substrate according to the present invention, a sample subjected to Raman spectroscopy can be directly subjected to mass spectrometry, and both peptides can be clearly distinguished from each other. The materials used herein are as follows: peptides having the amino acid sequence of EQWPQCPTXK (SEQ ID NO: 4), specifically a peptide wherein X is isoleucine, and an alkyne peptide wherein X is propargyl glycine. The Raman spectra in FIG. 6 correspond to the upper right section of FIG. 16, and the mass spectra in FIG. 7 correspond to the lower right section of FIG. 16.

FIG. 17 shows a multi-spotted substrate with all surfaces made of quartz. This quartz substrate was fixed to the base using a magnet, as shown in the lower section of FIG. 17.

Example 9 SERS Measurement Using Gold Nanoparticles

A dispersion (EMGC50, BBI) of gold nanoparticles having a diameter of 50 nm was added dropwise to a glass substrate, and then dried. 1 µl of 6 mM RAT8-AOMK dissolved in DMSO was added dropwise onto dried aggregates of gold nanoparticles. For comparison, 1 µl of 6 mM RAT8-AOMK dissolved in DMSO was similarly added dropwise onto a glass substrate with no gold nanoparticles. Raman measurement was performed for each droplet. Raman spectroscopy was performed using a laser Raman microscope (Nanophoton Corporation, Raman-11). A laser with a wavelength of 660 nm was used for a laser beam source. Line illumination was selected as the laser illumination pattern. Laser intensity was 3.5 mW on the surface of a sample after the laser had passed through an objective lens, and the exposure time was 10 seconds. The objective lens with a numerical aperture of 0.75 and a magnification of ×40 was used. Raman spectra obtained for 400 spots along the line were averaged, so as to find the spectrum for each droplet. Raman spectra with wavenumbers ranging from 1250 to 2400 $cm^{-1}$ were obtained. The results are shown in FIG. 34. Enhanced Raman signals were confirmed using gold nanoparticles.

Figure 35:
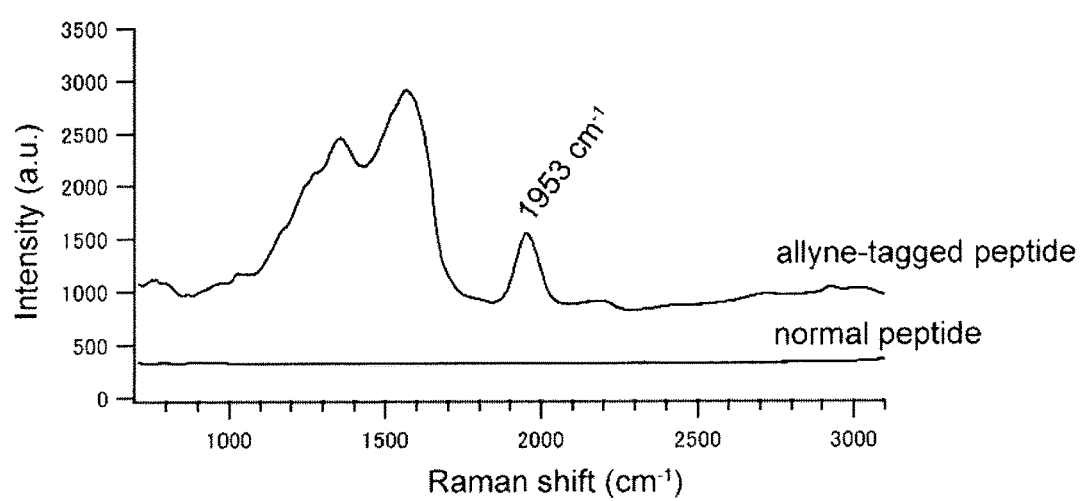
FIG. 35 shows the result of performing SERS measurement by mixing a dispersion of silver nanoparticles with an aqueous solution of an alkyne-labeled and unlabeled peptides. The upper spectrum indicates the result for the alkyne-labeled peptide, and the lower spectrum indicates the result for the normal peptide.

Example 10 SERS Measurement Using a Mixture with a Dispersion of Silver Nanoparticles 15 µl of a dispersion (EMSC50, BBI) of silver nanoparticles having a diameter of 40 nm was mixed with 15 µl of water containing 10 pmol alkyne peptide 1 dissolved therein. The mixture was injected into 1 section of a glass bottom well (EzView 384-well glass bottom assay plate, AGC Technoglass). Similarly, a solution containing silver nanoparticles and 10 pmol unlabeled peptide 1 dissolved therein was injected into a different section of the same well plate. The well plate was covered with a tape, and then kept in a refrigerator (4° C.) for 1 day. Then Raman measurement was performed. Raman spectroscopy was performed using a laser Raman microscope (Nanophoton Corporation, Raman-11). A laser with a wavelength of 532 nm was used for a laser beam source. Line illumination was selected as the laser illumination pattern. Laser intensity was 240 mW on the surface of a sample after the laser had passed through an objective lens. The exposure time was 1 second/line. Measurement was performed for 25 lines per sample. The objective lens with a numerical aperture of 0.75 and a magnification of ×40 was used. 10,000 Raman spectra (400 spots (per line)×25 lines) obtained along the lines were averaged, thereby obtaining a Raman spectrum with wavenumbers ranging from 710 to 3100 $cm^{-1}$ for each solution. The results are shown in FIG. 35.

Example 11 and Comparative Example

Comparison of a case in which the Raman spectroscopy method of the present invention was used, with a case in which a fluorophore was introduced via a click reaction according to a conventional method
Preparation of Samples
Cathepsin B (10 µg, CALBIOCHEM, catalog No. 219362) was dissolved in 100 µl of Bogyo buffer (50 mM acetic acid (pH5.6), 5 mM MgCl2, 2 mM DTT). The solution was left to stand at room temperature for 15 minutes, and then mixed with 20 mM RAT8-AOMK in 1.0 µl of DMSO. The mixture was incubated at 37° C. for 3 hours, the protein was incubated on ice for 3 hours, and then TCA sedimentation was performed. Centrifugation was performed at 20000 G for 20 minutes to obtain the precipitate. After removal of the supernatant, 1 ml of acetone was added, and then centrifugation was performed at 20000 G for 15 minutes. Centrifugation and acetone treatment were repeated 3 times. After 30 seconds of the removal of acetone under vacuum, the precipitate was dissolved in 10 µl of a denaturation buffer (7 M GuHCl, 1 M Tris-HCl (pH 8.5)).

A Click-iT protein reaction buffer kit (C10276, Invitrogen) was used for click reaction. 100 µl of 40 µM Alexa Fluor 488 azide was added. 50 µl of water was added, and then the solution was vortex-stirred for 5 seconds. 10 µl of $CuSO_4$ (component B) was added, and then the solution was vortex-stirred for 5 seconds. 10 µl of a Click-iT reaction buffer additive 1 solution was added, and then the solution was vortex-stirred for 5 seconds. The solution was left to stand for 3 minutes. 20 µl of a Click-iT reaction buffer additive 2 solution was added, and then the solution was vortex-stirred for 5 seconds.

Next, the solution was rotated end-over-end using a rotary machine for 20 minutes. 600 µl of methanol was added, and then vortex stirring was performed for a short period of time. 150 µl of chloroform was added, and then vortex stirring was performed for a short period of time. 400 µl of purified water was added, and then vortex stirring was performed for a short period of time. Centrifugation was performed at 18000 G for 5 minutes, to remove the supernatant. 450 µl of methanol was added and then vortex stirring was performed for a short period of time. Centrifugation was performed at 18000 G for 5 minutes, and then the supernatant was discarded. 450 µl of methanol was added, and then vortex stirring was performed for a short period of time. Centrifugation was performed at 18000 G for 5 minutes, and then the supernatant was discarded. The pellet was air-dried for 15 minutes, and then 10 µl of a denaturation buffer (7M GuHCl, 1 M Tris-HCl (pH 8.5)) was added. 10 µl of a denaturation buffer (7 M GuHCl, 1M Tris-HCl (pH 8.5)) was added to each sample, so that the total volume of the solution was 20 µl. For both the case with a click reaction and the case without a click reaction, 19 µl out of 20 µl of the solution was incubated at 37° C. for 1 hour. After reduction and alkylation with DTT and IAA, each sample was incubated at 37° C. for 6 hours. Next, water and 27 µl of 0.1% DG were added to prepare 266 µl of a sample solution. 3.0 µl of trypsin (100 ng/µl) was added to the sample, and then the sample was left to stand at 37° C. overnight.

Obtaining the UV Chromatogram

Figure 36:
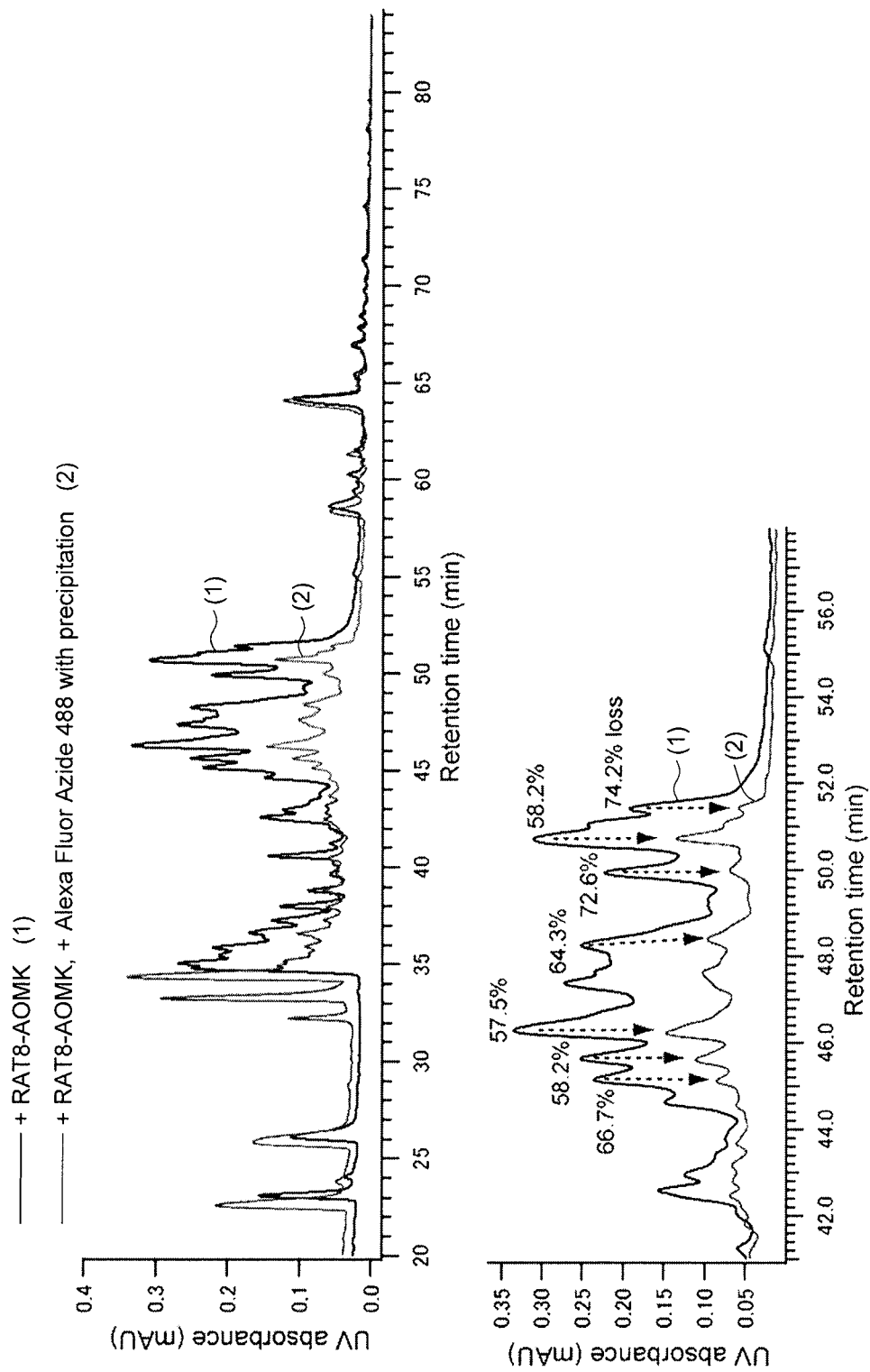
FIG. 36 shows the results of comparing a case in which a fluorophore was introduced via a click reaction with a case in which Raman spectroscopy was performed. UV chromatogram (1) in the lower section shows the case of Raman spectroscopy of the present invention, and UV chromatogram (2) shows the case in which the fluorophore was introduced via a click reaction. In the case of click reaction, the loss of 57.5% to 74.2% of the samples was observed.

100 µl of a peptide mixture prepared as described above was lyophilized, and then dissolved in 50 µl of water. 50 µl of the solution was injected into a nano-LC system (nano-Frontier, Hitachi). Experimental conditions employed herein are as follows. Raman spectroscopy without any click reaction was performed at a flow rate of 250 nl/minute and 20 s/spot (Probot, Dionnex) using a 384-well glass bottom plate (EzView 384-well glass bottom assay plate, AGC Technoglass). Fluorescence analysis with a click reaction was performed at a flow rate of 250 nl/minute and 20 s/spot (Probot, Dionnex) using a 384-well water-repellent MALDI plate (ITOP, Thermo). 1.5 µl of water was added per fraction from the side port of the probot, so as to help the stable distribution of drops of water onto the glass well plate. The UV chromatogram was obtained using a UV detector (MU701, GL science) at 215 nm. The gradient employed herein was: 0 minute 5%, 60 minutes 80%, 60.01 minutes 95%, 75 minutes 95%, 75.01 minutes 0%, and 90 minutes 0%. The total number of fractions was 192. FIG. 36 shows the retention times ranging from 20 to 85 minutes. For comparison of peak heights in the UV chromatogram shown in the upper section of FIG. 36, the chart of the retention times ranging from 41 to 57.5 minutes was enlarged as shown in the lower section of FIG. 36. As shown in the lower section of FIG. 36, the loss of 57.5% to 74.2% of the samples was observed for the case (2) (as a comparative example) of using a click reaction, unlike the case (1) of the present invention using no click reaction.

Obtaining the Raman Chromatogram

After droplets on the 384-well glass bottom plate were dried, Raman measurement was performed. Raman spectroscopy was performed using a laser Raman microscope (Nanophoton Corporation, Raman-11). A laser with a wavelength of 532 nm was used for a laser beam source. Point illumination was selected as the laser illumination pattern. Laser intensity was 180 mW on the surface of a sample after the laser had passed through an objective lens. The exposure time was 30 seconds. The objective lens with a numerical aperture of 0.75 and a magnification of ×40 was used. Spectra were obtained 5 times per sample at different positions on peptide aggregates, and then averaged. Similar measurement was performed for all 192 wells. Raman spectra with wavenumbers ranging from 710 to 3100 $cm^{-1}$ were obtained. Smoothing was applied to the thus obtained spectra by the method of moving averages. The value of the alkyne-derived Raman peak bottom at 2091 $cm^{-1}$ was subtracted from the value of the alkyne-derived Raman peak top at 2108 $cm^{-1}$ to calculate the Raman intensity of alkyne in each well, thereby preparing an intensity profile as an Raman chromatogram.

Obtaining the Fluorescence Chromatogram

After droplets on a 384-well water-repellent MALDI plate were dried, fluorescence measurement was performed. Fluorescence measurement was performed using a fluorescence imager (Pharos FX, Biorad). The excitation wavelength selected herein was 488 nm. The resolution selected herein was 50 µm. The highest fluorescence intensity was calculated for each spot, so as to find the fluorescence intensities of a total of 192 spots on the basis of the thus obtained fluorescence image, thereby preparing an intensity profile as a fluorescence chromatogram.

Figure 37:
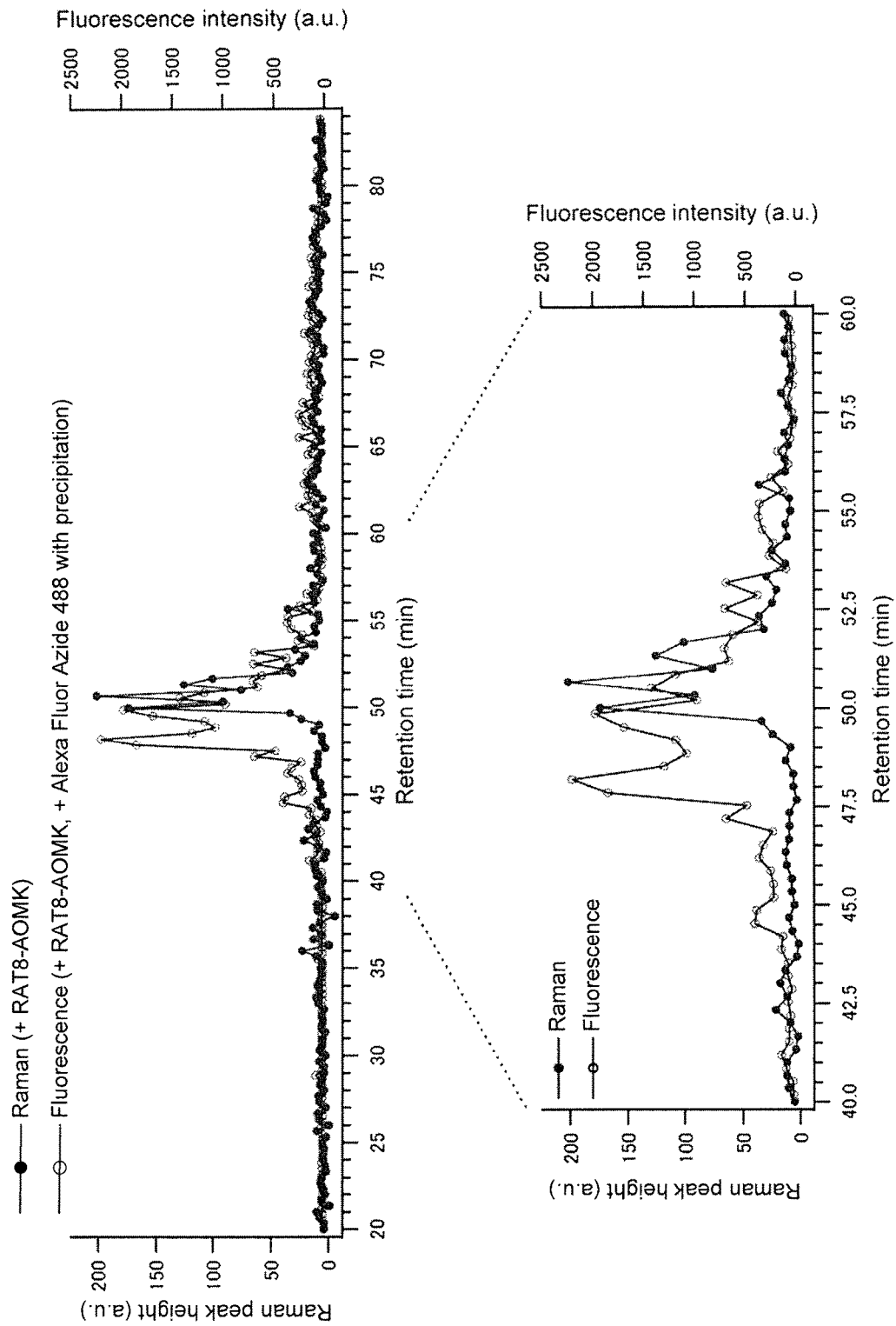
FIG. 37 shows the results of comparing a case in which a fluorophore was introduced via a click reaction with a case of Raman. Black circles indicate the Raman chromatogram, and white circles indicate the UV chromatogram for which a fluorophore was introduced via a click reaction.

Differences between the Raman chromatogram and the fluorescence chromatogram are shown in FIG. 37. FIG. 37 shows in the lower section an enlarged view corresponding to the retention times ranging from 40 to 60 minutes. Regarding characteristic three peaks, fluorescence signals were observed between 47.5 and 51.0 minutes in the case of the fluorescence chromatogram. On the other hand, in the case of the Raman chromatogram, Raman signals were observed within a narrower range between 49.5 and 52.0 minutes. Moreover, in the case of the fluorescence chromatogram, many nonspecific signals (noise) were observed before and after these three peaks. These results demonstrate that separation by the Raman chromatography of the present invention using no fluorophore has higher specificity for separation of a target sample, compared with the comparative example involving performing a click reaction with a large molecular weight of a fluorophore and then separating a sample by UV chromatography.

Example 12 SERS Measurement of Alkyne-Labeled Peptides of a TFA Added System and a Non TFA Added System 15 µl of 40-nm silver nanoparticles (EMSC40, British BioCell International) was added to 15 µl of an alkyne-labeled peptide (alkyne peptide 1; EQWPQCPTXK; X=propargyl glycine)/0.3% TFA aqueous solution with a predetermined concentration, and then the mixture was left to stand at 4° C. for 1 day. SERS measurement was performed using the sample.

SERS measurement was automatically performed using a laser Raman microscope (Nanophoton Corporation, Raman-11) with a 532 nm excitation laser. The laser output after passing through the objective lens was 240 mW, and the exposure time ranged from 1 to 3 seconds. The objective lens with a magnification of ×40 and a numerical aperture of 0.75 was used. Line illumination was selected for the laser illumination pattern. Alkyne intensity was obtained from the wavenumber of 1958 $cm^{-1}$. As a result, the alkyne detection sensitivity of SERS in the TFA added system was 100 fmol (femtomole) based on peptide.

Regarding the non TFA added system (in which no TFA was added), a sample was prepared by procedures similar to the above TFA added system except for not adding TFA, and then SERS measurement was performed. As a result, SERS detection sensitivity was 3 pmol (picomole) based on peptide. However, in the case of the non TFA added system, the injected volume of alkyne peptide 1 did not always correlate with SERS intensity.

The TFA added system had detection sensitivity for alkyne about 30 times higher than that of the non TFA added system. The TFA added system also had SERS intensity about 4 to 5 times higher than that of the non TFA added system, confirming significant improvement in SERS measurement operability. Furthermore, in the case of the TFA added system, the injection volume of alkyne peptide 1 was in good correlation with SERS intensity in a dynamic range of 100 fmol-100 pmol, and thus the measurement system was stabilized. This may be because aggregates were homogeneously distributed by the aggregation-accelerating agent of the present invention (organic acid).

Example 13 SERS Measurement of RAT8-AOMK-Labeled Cathepsin B of TFA Added System RAT8-AOMK-labeled cathepsin B sample was prepared by procedures basically similar to those in Example 3, and then digested with trypsin. According to the following procedures, a sample containing the RAT8-AOMK-labeled cathepsin B fragment was fractionated by nano LC-UV-probot into wells to which TFA had been added. Fractions were mixed with silver nanoparticles. After aggregation, SERS measurement was performed.

The sample was fractionated as follows. The thus prepared 100 μl of a peptide mixture was lyophilized and then dissolved in 50 μl of a solution. The whole sample was injected into nano LC-UV-Probot and then fractionation was performed.
Peptide Separation by Nano LC-UV-Probot was Performed Under the Following Conditions:
Flow rate: 250 nl/min
Fractionation: 384-well glass bottom plate (EzView 384 well glass bottom assay plate, AGC Technoglass), 20 seconds per spot.
UV chromatogram: 215 nm
Concentration gradient: 0 minute 5%, 60 minutes 80%/60.01 minutes 95%, 75 minutes 95%/75.01 minutes 0%, and 90 minutes 0%
Fractionation: 20 seconds per well A sample was fractionated into a glass bottom well plate containing in advance 25 μl of 0.1% TFA aqueous solution. The fractionated sample was separated into 15 μl for SERS and 10 μl for mass spectrometry. 15 μl of 40-nm silver nanoparticles was added to the sample for SERS, the resultant was left to stand at 4° C. for 1 day, and then SERS measurement was performed.

SERS measurement was automatically performed using a laser Raman microscope (Nanophoton Corporation, Raman-11) with line illumination, a 532-nm excitation laser, and HTS software. The laser output after passing through the objective lens was 130 mW, and the exposure time ranged from 1 to 3 seconds. The objective lens with a magnification of ×40 and a numerical aperture of 0.75 was used. Line illumination was selected for the laser illumination pattern. Alkyne intensity was obtained from wavenumbers ranging from 1981 to 1900 cm$^{-1}$.

The time required for SERS measurement was significantly shortened, 38 minutes/192 wells, since TFA addition resulted in the homogeneous distribution of aggregates of peptides and silver nanoparticles and facilitated operation for setting a laser focus.

Subsequently, from among the fractionated samples, those samples, for which alkyne signals had been observed by SERS measurement, were subjected to mass spectrometry and, the RAT8-AOMK-labeled cathepsin B fragment was confirmed.

INDUSTRIAL APPLICABILITY

According to the apparatus and the method of the present invention, a biomolecule that binds to a low-molecular-weight compound can be specified, and, further, the binding site of the low-molecular-weight compound and the biomolecule can be identified. Therefore, with the apparatus and the method according to the present invention, proteins to be targeted by drugs can be searched for in the field of drug discovery, and the drug binding sites in the proteins can be identified. Furthermore, the present invention enables analysis of the post-translational modification of a protein in the biological field. Furthermore, the whole or a portion of the amino acid sequence of a protein or a peptide specified using the apparatus and the method according to the present invention can be determined by MS/MS analysis. Furthermore, the present invention enables SERS measurement with high sensitivity.

EXPLANATION OF SYMBOLS

1: Sample injection unit
2: Liquid-feeding line
3: Fractionation unit
4: Liquid-feeding line
5: Detection unit
6: Laser unit
7: Mirror
8: Objective lens
9: Sample
10: Sample stand
11: Chromator
12: Detection unit
13: Sample stage
14: Sample
15: Laser unit
16: Acceleration electrode
17: Detection unit
18: Signal processing unit

SEQUENCE LISTING FREE TEXT

SEQ ID NO: 1: Human cathepsin B
SEQ ID NO: 2: Peptide A-2
SEQ ID NO: 3: Peptide B-1
SEQ ID NO: 4: Peptide 1
SEQ ID NO: 5: Unlabeled peptide fragment All publications, patents, and patent applications cited herein are incorporated herein by reference in their entirety.

We claim:

1. A method for identifying the binding site of a protein bound to a low-molecular-weight compound, comprising the following steps of:
   (i) preparing fractionated fragments comprising the steps of:
      mixing the low-molecular-weight compound with the protein and obtaining the protein bound to the low-molecular-weight compound,
      fragmenting the protein bound to the low-molecular-weight compound by chemical degradation or an enzyme selected from the group consisting of protease and peptidase, and
      fractionating the fragmented protein bound to a low-molecular weight compound by liquid chromatography or capillary electrophoresis,
   (ii) subjecting fractionated fragments of the protein bound to the low-molecular-weight compound to Raman spectroscopy,
   (iii) detecting a fraction having a Raman peak derived from the low-molecular-weight compound bound to a fragment of the protein via Raman spectroscopy, wherein the low-molecular-weight compound comprises at least one type of substituent selected from the group consisting of an alkynyl group, a nitrile group, a diazonio group, an isocyanate ester group, an isonitrile group, a ketene group, a carbodiimide group, a thiocyanate ester group, an azide group, an alkynediyl group, and deuterium having a scattering spectrum in a silent region of the Raman spectrum and exhibits a Raman peak distinguishable from that of the protein, wherein said low-molecular-weight compound comprises said at least one type of substituent during said detection via Raman spectroscopy, (iv) subjecting the fraction subjected to Raman spectroscopy to mass spectrometry and tandem mass spectrometry, wherein said low-molecular-weight compound comprises said at least one type of substituent during said mass spectrometry and tandem mass spectrometry, (v) obtaining the mass and tandem mass spectrometric results for a fraction having a Raman peak derived from the low-molecular-weight compound, (vi) comparing the results with the mass information of the protein, (vii) identifying the fractionated fragment binding to the low-molecular-weight compound by searching for a fractionated fragment, whose mass is shifted by the low-molecular-weight compound, and (viii) identifying the amino acid residue within the protein which binds to the low-molecular-weight compound by searching for an amino acid residue, whose mass is shifted by the low-molecular-weight compound, thereby identifying the binding site of a protein, said method further comprising the steps of:

adding a solution containing a metal nanoparticle or a metal nanostructure to the fractionated fraction prior to the Raman spectroscopy, and adding an organic acid to the fractionated fraction prior to the Raman spectroscopy.

2. The method according to claim 1, wherein said mixing the low-molecular-weight compound with the protein is carried out under acellular conditions.

3. The method according to claim 1, wherein the fractionated fraction is a droplet, the method further comprising (a-1) arranging the droplet on a plate having a cleaned surface, wherein the plate comprises a metal nanoparticle or a metal nanostructure selected from the group consisting of gold, silver, platinum, palladium, aluminum, titanium and copper, and (a-2) adding an organic acid to the spot containing the fractionated fraction to accelerate the formation of homogeneous aggregates between the metal nanoparticle or metal nanostructure, and the protein bound to the low-molecular-weight compound, thereby preparing the spot to be subjected to Raman spectroscopy, or the method further comprising (b-1) adding an organic acid to a plate having a cleaned surface, wherein the plate comprises a metal nanoparticle or a metal nanostructure selected from the group consisting of gold, silver, platinum, palladium, aluminum, titanium and copper, thereby forming aggregates of the metal nanoparticle or metal nanostructure, and (b-2) arranging the droplet on the plate in order to accelerate the formation of homogeneous aggregates between the metal nanoparticle or metal nanostructure, and the protein bound to the low-molecular-weight compound, thereby preparing the spot to be subjected to Raman spectroscopy.

4. The method according to claim 1, wherein the organic acid is selected from the group consisting of trifluoroacetic acid, difluoroacetic acid, monofluoroacetic acid, trifluoromethanesulfonic acid, difluoromethanesulfonic acid, 3,3,3-trifluoropropionic acid, trichloroacetic acid, dichloroacetic acid, monochloroacetic acid, trichloromethanesulfonic acid, dichloromethanesulfonic acid, 3,3,3-trichloropropionic acid, formic acid, acetic acid, propionic acid, methanesulfonic acid, and a combination thereof.

5. The method according to claim 1, wherein the low-molecular-weight compound comprises an alkynyl group having a scattering spectrum in a silent region of the Raman spectrum.

6. The method according to claim 1, further comprising (a-1) mixing the fractionated fraction with a solvent to prepare a droplet, (a-2) arranging the droplet on a plate having a cleaned surface, (a-3) adding a solution containing a metal nanoparticle or a metal nanostructure to the spot containing the fractionated fraction, and (a-4) adding an organic acid to the spot containing the fractionated fraction to accelerate the formation of homogeneous aggregates between the metal nanoparticle or metal nanostructure, and the protein bound to the low-molecular-weight compound, or further comprising (b-1) mixing the fractionated fraction with a solvent to prepare a droplet, (b-2) arranging the droplet on a plate having a cleaned surface, (b-3) adding an organic acid to the droplet containing the fractionated fraction, and (b-4) adding a solution containing a metal nanoparticle or a metal nanostructure to the droplet containing the fractionated fraction and organic acid in order to accelerate the formation of homogeneous aggregates between the metal nanoparticle or metal nanostructure, and the protein bound to the low-molecular-weight compound thereby preparing the droplet to be subjected to Raman spectroscopy, or further comprising (c-1) mixing the fractionated fraction with a solution containing a metal nanoparticle or a metal nanostructure, (c-2) adding an organic acid to the mixed solution to accelerate the formation of homogeneous aggregates between the metal nanoparticle or metal nanostructure, and the protein bound to the low-molecular-weight compound, and (c-3) arranging the mixed solution containing the aggregates on a plate having a cleaned surface, thereby preparing solutions to be subjected to Raman spectroscopy, or further comprising (d-1) mixing the fractionated fraction with a solution containing a metal nanoparticle or a metal nanostructure, (d-2) arranging the mixed solution on a plate having a cleaned surface, and (d-3) adding an organic acid to the mixed solution to accelerate the formation of homogeneous aggregates between the metal nanoparticle or metal nanostructure, and the protein bound to the low-molecular-weight compound, thereby preparing solutions to be subjected to Raman spectroscopy, or further comprising (e-1) adding an organic acid to the fractionated fraction, (e-2) adding a solution containing a metal nanoparticle or a metal nanostructure to the fractionated fraction containing the organic acid in order to accelerate the formation of homogeneous aggregates between the metal nanoparticle or metal nanostructure, and the protein bound to the low-molecular-weight compound, and (e-3) arranging the mixed solution containing the aggregates on a plate having a cleaned surface, thereby preparing solutions to be subjected to Raman spectroscopy, or further comprising (f-1) adding an organic acid to the fractionated fraction, (f-2) arranging the fractionated fraction containing the organic acid on a plate having a cleaned surface, and (f-3) adding a solution containing a metal nanoparticle or a metal nanostructure to the fractionated fraction in order to accelerate the formation of homogeneous aggregates between the metal nanoparticle or metal nanostructure, and the protein bound to the low-molecular-weight compound, thereby preparing solutions to be subjected to Raman spectroscopy.

7. The method according to claim 6, wherein the organic acid is selected from the group consisting of trifluoroacetic acid, difluoroacetic acid, monofluoroacetic acid, trifluoromethanesulfonic acid, difluoromethanesulfonic acid, 3,3,3-trifluoropropionic acid, trichloroacetic acid, dichloroacetic acid, monochloroacetic acid, trichloromethanesulfonic acid, dichloromethanesulfonic acid, 3,3,3-trichloropropionic acid, formic acid, acetic acid, propionic acid, methanesulfonic acid, and a combination thereof.

8. The method according to claim 3, the method further comprising
vaporizing the solvent contained in the droplet to form a spot on the plate containing the fractionated fraction to be subjected to Raman spectroscopy, wherein said vaporizing is carried out after arranging the droplet on the plate and before adding the organic acid to the spot.

9. The method according to claim 6, further comprising
vaporizing the solvent contained in the droplet, to form a spot on the plate containing the fractionated fraction, wherein said vaporizing is carried out after arranging the droplet on the plate and before adding the organic acid to the spot.

10. The method according to claim 1, further comprising
mixing the fractionated fraction with a solvent to prepare a droplet, and
arranging the droplet on a plate having a cleaned surface, thereby preparing the droplet to be subjected to Raman spectroscopy, or the method according to claim 1, further comprising
arranging the fractionated fraction on a plate having a cleaned surface, thereby preparing the fractionated fraction to be subjected to Raman spectroscopy.

11. The method according to claim 10, further comprising
vaporizing the solvent contained in the droplet to form a spot on the plate containing the fractionated fraction, wherein said vaporizing is carried out after arranging the droplet on the plate.

12. The method according to claim 1, further comprising
mixing the fractionated fraction with a solvent to prepare a droplet,
arranging the droplet on a plate having a cleaned surface, wherein the plate comprises a metal nanoparticle or a metal nanostructure selected from the group consisting of gold, silver, platinum, palladium, aluminum, titanium and copper and thereby preparing the droplet to be subjected to Raman spectroscopy, or the method according to claim 1, further comprising
arranging the fractionated fraction on a plate having a cleaned surface, wherein the plate comprises a metal nanoparticle or a metal nanostructure selected from the group consisting of gold, silver, platinum, palladium, aluminum, titanium and copper thereby preparing the fractionated fraction to be subjected to Raman spectroscopy.

13. The method according to claim 12, further comprising
vaporizing the solvent contained in the droplet to form a spot on the plate containing the fractionated fraction, wherein said vaporizing is carried out after arranging the droplets on the plate.

14. The method according to claim 6, wherein the low-molecular-weight compound comprises an alkynyl group having a scattering spectrum in a silent region of the Raman spectrum.

* * * * *

SEQUENCE LISTING

<160> NUMBER OF SEQ ID NOS: 5

<210> SEQ ID NO 1
<211> LENGTH: 339
<212> TYPE: PRT
<213> ORGANISM: Homo sapiens
<220> FEATURE:
<223> OTHER INFORMATION: Homo sapiens cathepsin B

<400> SEQUENCE: 1

```
Met Trp Gln Leu Trp Ala Ser Leu Cys Cys Leu Leu Val Leu Ala Asn
 1               5                  10                  15

Ala Arg Ser Arg Pro Ser Phe His Pro Leu Ser Asp Glu Leu Val Asn
             20                  25                  30

Tyr Val Asn Lys Arg Asn Thr Thr Trp Gln Ala Gly His Asn Phe Tyr
         35                  40                  45

Asn Val Asp Met Ser Tyr Leu Lys Arg Leu Cys Gly Thr Phe Leu Gly
     50                  55                  60

Gly Pro Lys Pro Pro Gln Arg Val Met Phe Thr Glu Asp Leu Lys Leu
 65                  70                  75                  80

Pro Ala Ser Phe Asp Ala Arg Glu Gln Trp Pro Gln Cys Pro Thr Ile
                 85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile
```

<210> SEQ ID NO 2

```
<211> LENGTH: 20
<212> TYPE: PRT
<213> ORGANISM: Homo sapiens
<220> FEATURE:
<223> OTHER INFORMATION: peptide from Homo sapiens cathepsin B

<400> SEQUENCE: 2

Asp Gln Gly Ser Cys Gly Ser Cys Trp Ala Phe Gly Ala Val Glu Ala
1               5                   10                  15

Ile Ser Asp Arg
            20

<210> SEQ ID NO 3
<211> LENGTH: 23
<212> TYPE: PRT
<213> ORGANISM: Homo sapiens
<220> FEATURE:
<223> OTHER INFORMATION: peptide from Homo sapiens cathepsin B

<400> SEQUENCE: 3

Glu Ile Arg Asp Gln Gly Ser Cys Gly Ser Cys Trp Ala Phe Gly Ala
1               5                   10                  15

Val Glu Ala Ile Ser Asp Arg
            20

<210> SEQ ID NO 4
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa is Ile or propargyl glycine

<400> SEQUENCE: 4

Glu Gln Trp Pro Gln Cys Pro Thr Xaa Lys
1               5                   10

<210> SEQ ID NO 5
<211> LENGTH: 18
<212> TYPE: PRT
<213> ORGANISM: Homo sapiens
<220> FEATURE:
<223> OTHER INFORMATION: peptide from Homo sapiens cathepsin B

<400> SEQUENCE: 5

Asn Gly Pro Val Glu Gly Ala Phe Ser Val Tyr Ser Asp Phe Leu Leu
1               5                   10                  15

Tyr Lys
```